United States Patent
LaVoie et al.

(10) Patent No.: US 9,227,966 B2
(45) Date of Patent: Jan. 5, 2016

(54) ANTIMICROBIAL AGENTS

(71) Applicant: Rutgers, The State University of New Jersey, New Brunswick, NJ (US)

(72) Inventors: Edmond J. LaVoie, New Brunswick, NJ (US); Daniel S. Pilch, New Brunswick, NJ (US); Ajit Parhi, New Brunswick, NJ (US); Malvika Kaul, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/186,516

(22) Filed: Feb. 21, 2014

(65) Prior Publication Data

US 2014/0315939 A1 Oct. 23, 2014

Related U.S. Application Data

(63) Continuation of application No. 13/266,740, filed as application No. PCT/US2010/033278 on Apr. 30, 2010, now abandoned.

(51) Int. Cl.
| | | |
|---|---|---|
| C07D 455/03 | (2006.01) |
| C07D 405/04 | (2006.01) |
| C07D 217/02 | (2006.01) |
| C07D 217/10 | (2006.01) |
| C07D 217/12 | (2006.01) |

(52) U.S. Cl.
CPC ............ C07D 455/03 (2013.01); C07D 217/02 (2013.01); C07D 217/10 (2013.01); C07D 217/12 (2013.01); C07D 405/04 (2013.01)

(58) Field of Classification Search
None
See application file for complete search history.

(56) References Cited

U.S. PATENT DOCUMENTS

| | | | |
|---|---|---|---|
| 4,098,887 A * | 7/1978 | Hill ................................ 514/188 |
| 4,309,539 A | 1/1982 | Boller et al. |
| 4,782,058 A | 11/1988 | Griffith |
| 5,077,142 A | 12/1991 | Sakon et al. |
| 5,177,067 A | 1/1993 | Guerry et al. |
| 5,177,075 A | 1/1993 | Suto et al. |
| 8,741,917 B2 | 6/2014 | LaVoie et al. |
| 2002/0035090 A1 | 3/2002 | Zeldis et al. |
| 2002/0077333 A1 | 6/2002 | Dey et al. |
| 2003/0181519 A1 | 9/2003 | Mewshaw et al. |
| 2006/0183943 A1 | 8/2006 | Hu |
| 2008/0027028 A1 | 1/2008 | Chichak |
| 2008/0300239 A1 | 12/2008 | Adams et al. |
| 2009/0076074 A1 | 3/2009 | Jung et al. |
| 2009/0312319 A1 | 12/2009 | Ren et al. |
| 2010/0120810 A1 | 5/2010 | Leblond et al. |
| 2012/0022061 A1 | 1/2012 | LaVoie et al. |
| 2012/0059026 A1 | 3/2012 | LaVoie |
| 2013/0109713 A1 | 5/2013 | LaVoie et al. |
| 2013/0116278 A1 | 5/2013 | LaVoie et al. |

FOREIGN PATENT DOCUMENTS

| | | |
|---|---|---|
| DE | 4327748 A1 | 2/1995 |
| EP | 0719764 A1 | 7/1996 |
| EP | 1078920 A1 | 2/2001 |
| EP | 1724262 A1 | 11/2006 |
| WO | WO 92/19242 A1 | 11/1992 |
| WO | WO 03/018017 A1 | 3/2003 |
| WO | WO 03/078397 A1 | 9/2003 |
| WO | WO 03/099274 A1 | 12/2003 |
| WO | WO 04/000814 A1 | 12/2003 |
| WO | WO 2004/005472 A2 | 1/2004 |
| WO | WO 2004/041210 A2 | 5/2004 |
| WO | WO 2004/087145 A2 | 10/2004 |
| WO | WO 2005/075428 A1 | 8/2005 |
| WO | WO 2006/067048 A1 | 6/2006 |
| WO | WO 2006/105289 A1 | 10/2006 |
| WO | WO 2008/016596 A2 | 2/2008 |
| WO | WO 2010/127307 A1 | 11/2010 |
| WO | WO 2011/156626 A1 | 12/2011 |

OTHER PUBLICATIONS

Chemical Abstract Registry No. 783291-11-2, indexed in the Registry File on STN CAS Online Nov. 18, 2004.*
Chemical Abstract Registry No. 199783-67-0, indexed in the Registry File on STN CAS Online Jan. 15, 1998.*

(Continued)

*Primary Examiner* — Michael Barker
*Assistant Examiner* — Po-Chih Chen
(74) *Attorney, Agent, or Firm* — Viksnins Harris & Padys PLLP

(57) ABSTRACT

The invention provides a compound of formula I:

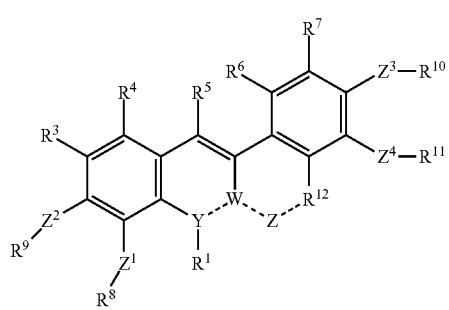

or a salt or prodrug thereof, wherein Y, W, Z, $Z^1$, $Z^2$, $Z^3$, $Z^4$, and $R^1$-$R^{12}$ have any of the values described in the specification, as well as compositions comprising a compound of formula I. The compounds are useful as antibacterial agents.

12 Claims, No Drawings

(56) References Cited

OTHER PUBLICATIONS

Ito et al. A medium-term rat liver bioassay for rapid in vivo detection of carcinogenic potential of chemicals. Cancer Science 2003, 94, 3-8.*

Bradsher et al. Aromatic Cyclodehydration. XLI. Meso-substituted Acridizinium Benzologs. Journal of Organic Chemistry 1959, 24, 589-591.*

Akiba et al., "Preparation of 13-Substituted 8H-Dibenzo[a,g]quinolizin-8-onces by Intramolecular Wittig-Horner Reaction of Dialkyl 2-(o-Acyl-benzoyl)-1,2-dihydro-1-isoquinolylphosphonates", *Bull. Chem. Soc. Japan*, 57 (8), 2188-2192 (1984).

Augstein et al., "Synthesis of 11-Hydroxy-2,3,9,10-tetramethoxy-5,6,13,13a-tetrahydro-8H-dibenzo[a,g]quinolizine. A Contribution to the Structure of Stepharotine", *Stepharotine*, vol. 34, No. 5, 1349-1352 (1969).

Bayer et al., "Pyridyl-substituierte Tetralonderivate: Eine neue Klasse nichtsteroidaler Aromatase-Inhibitoren", *Arch. Pharm.*, 324, 815-820 (1991).

Bedi et al., "Synthesis and biological activity of novel antibacterial quinazolines", *Bioorganic & Medicinal Chemistry Letters*, vol. 14 (20), 5211-5213 (2004).

Beilstein, Database Beilstein Institute for Organic Chemistry, XP002591901, Database Accession No. 3834367 (BRN) abstract (1918).

Beilstein, Database Beilstein Institute for Organic Chemistry, XP002591900, Database Accession No. 3837583(BNR) abstract (1930).

Beuria, T.K. et al., "Sanguinarine Blocks Cytokinesis in Bacteria by Inhibiting FtsZ Assembly and Bundling", *Biochemistry*, 44, 16584-16593 (2005).

Bild et al., "Discovery of Inhibitors of MCF-7 Tumor Cell Adhesion to Endothelial Cells and Investigation on their Mode of Action", *Archiv Der Pharmazie*, vol. 337 (12), 687-694 (2004).

Chen et al., "Synthesis and Antibacterial Evaluation of Certain Quinolone Derivatives", *J. Med. Chem.*, 44, 2374-2377 (2001).

Cole et al., "Potential Tumor-Selective Nitroimidazolylmethyluracil Prodrug Derivatives: Inhibitors of the Angiogenic Enzyme Thymidine Phosphorylase", J. Med. Chem., 46, 207-209 (2003).

Database Registry [Online], Chemical Abstracts Service, XP002570845, Database accession No. 1043562-34-0/RN, abstract (2008).

Denes et al., "The chemistry of sanguinarine", XP002570844, Chemical Abstracts Service, Database accession No. 1960:91836, abstract, *Magyar Kemiai Folyoirat*, 64,125-130 (1958).

Dyke et al., "The Chemistry of Cryptopine—I The Epicryptopines", *Tetrahedr0n*, vol. 24, No. 3, 1455-1465 (1968).

Dyke et al., "The Chemistry of Cryptopine—II Pseudocryptopine Chloride", *Tetrahedron*, vol. 25, 5375-5381 (1969).

Dykhuizen, "Santa Rosalia revisited: Why are there so many species of bacteria?", *Antonie van Leeuwenhock*, 73, 25-33 (1998).

Foroumadi et al., "Synthesis and in vitro antibacterial evaluation of N-[5-(5-nitro-2-thienyl)-1,3,4-thiadiazole-2-yl] piperazinyl quinolones", *European Journal of Medicinal Chemistry*, 38, 851-854 (2003).

Gopinath et al., "Dehydrogenation cyclization of 2-aryl-l-tetralone oxime acetates", XP002570843, Chemical Abstracts Service, Database accession No. 1960:23123, abstract, *Current Science*, 28, 241-242 (1959).

Huecas et al., "Protein Structure and Folding: The Interactions of Cell Division Protein FtsZ with Guanine Nucleotides", *J. Biol. Chem.*,282, 37515-37528 (2007).

Ishii et al., "Studies on the Chemical Constituents of Rutaceous Plants. LV.1 The Development of a Versatile Mehtod for the Synthesis of Antitumor-Active Benzo[c]phenanthridine Alkaloids. (5).1 A New Method for Quaternization of the Benzo[c]phenanthridine Nucleus", *Chem. Pharm. Bull.*, 32(8), 2984-2994 (1984).

Jackson et al., "Non-Steroidal Aromatase Inhibitors Based on a Biphenyl Scaffold: Synthesis, in vitro SAR, and Molecular Modelling", *Chem. Med. Chem.*, vol. 3, (4), 603-618 (2008).

Kaul et al., "A Bactericidal Guanidinomethyl Biaryl That Alters the Dynamics of Bacterial FtsZ Polymerization", *Journal of Medicinal Chemistry*, 55(22), 10160-10176 (2012).

Leroux et al., "N-(4-Biphenylmethyl)imidazoles as Potential Therapeutics for the Treatment of Prostate Cancer: Metabolic Robustness Due to Fluorine Substituion?", *Helvetica Chimica Acta, Verlag Helvetica*, vol. 86, 2671-2686 (2003).

Okudaira et al., "A Study of the Intestinal Absorption of an Ester-Type Prodrug, ME3229, in Rats: Active Efflux Transport as a Cause of Poor Bioavailability of the Active Drug", *Journal of Pharmacology and Experimental Therapeutics*, vol. 294 (2), 580-587 (2000).

Patent Cooperation Treaty, International Searching Authority, Search Report and Written Opinion for PCT/US2010/033278, 15 pages, dated Aug. 17, 2010.

Roesch et al., "Synthesis of isoquinolines and pyridines by the palladium-catalyzed iminoannulation of internal alkynes", *J. Org. Chem*. 66, 8042-8051 (2001).

Sanders et al., "Selective Cytotoxicity of Topoisomerase-Directed Protoberberines against Glioblastoma Cells", *Biochemical Pharmacology*, vol. 56, 1157-1166 (1998).

Sethi, "Enzyme Inhibition VIII: Mode of Inhibition of Reverse Transcriptase Activity by Analogues, Isomers, and Related Alkaloids of Coralyne", *Journal of Pharmaceutical Sciences*, vol. 74 (8), 889-891 (1985).

Wachall et al., "Imidazole Substitued Biphenyls: A new Class o Highly Potent and in Vivo Active Inhibitors of P450 17 as Potential Therapeutics for Treatment of Prostate Cancer", *Bioorganic &Medicinal Chemistry*, vol. 7 (9), 1913-1924 (1999).

Wu et al., "Regulatory perspectives of Type II prodrug development and time-dependent toxicity management: Nonclinical Pharm/Tox analysis and the role of comparative toxicology", *Toxicology* 236, 1-6 (2007).

Yaeko et al., "Studies on the constituents of Bocconia Cordata. IV. Transformation of sanguinarine into bocconine", XP002570841, Chemical Abstracts Service, Database accession No. 1992:129332, abstract, *Journal of Heterocyclic Chemistry*, 28(8), 1841-1843 (1991).

Yamaguchi et al., "Utilization of Protopine and Related Alkaloids. XIV. Oxidation of the Photo-adduct of 1-Oxoanhydromethylberberine with Nitrosobenzene, and Synthesis of Ring C-Substituted Benzo[c]phenanthridines", *Chem. Pharm. Bull.*, 31(5), 1601-1611 (1983).

* cited by examiner

ANTIMICROBIAL AGENTS

PRIORITY OF INVENTION

This application claims priority from U.S. application Ser. No. 13/266,740, filed 30 Apr. 2010, which claims priority from International Application Number PCT/US2010/033278, filed 30 Apr. 2010, which claims priority from U.S. Provisional Application No. 61/174,337 filed 30 Apr. 2009, which applications are herein incorporated by reference.

BACKGROUND OF THE INVENTION

The emergence of Multidrug Resistant (MDR) bacterial pathogens (e.g. methicillin-resistant *Staphylococcus aureus* (MRSA), *Acinetobacter baumannii-calcoaceticus* complex (ABC), etc.) has increased concerns as to the adequacy of current antimicrobials and pathogen treatment methods. The lethality of such pathogens, particularly MRSA, has often led to treatment methods that are experimental or would otherwise normally be avoided in standard clinical practice. For example, the antibiotic colistin was traditionally considered too nephrotoxic and neurotoxic for clinical use, but is nevertheless used to treat many MDR bacterial infections due to a paucity of available active drugs. The growing threat from MDR pathogens highlights a critical need to expand currently available antimicrobials. In this connection, there is a pressing need for new antibiotics that exhibit novel mechanisms of action or that are able to circumvent known resistance pathways.

Elements of the bacterial cell division machinery present appealing targets for antimicrobial compounds because (i) they are essential for bacterial viability, (ii) they are widely conserved among bacterial pathogens, and (iii) they often have markedly different structures than their eukaryotic homologs. One such protein that has been identified as a potential target is the FtsZ protein. During the division process, FtsZ, along with approximately 15 other proteins, assemble at mid-cell into a large cell division complex (termed the divisome), ultimately facilitating cell cytokinesis. More importantly, FtsZ is widely conserved among many bacterial strains.

SUMMARY OF THE INVENTION

In one embodiment the invention provides compounds that display antimicrobial activity. Accordingly, the invention provides a compound of formula I:

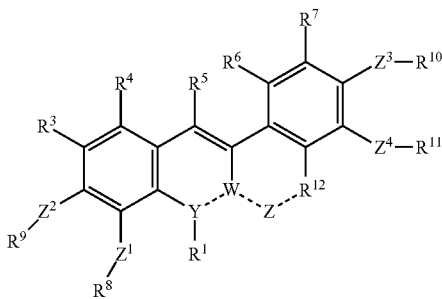

wherein:

the dashed line between Y and W represents a single or double bond;

when Y is —$CR^2$—, Z is —$(CR^{13}{}_2)_2$— or —$CR^{14}$=$CR^{14}$— and $R^{12}$ is a bond; W is N or $(NR^a)^+X^-$;

when Y is —$CR^2$— and Z is absent; W is $NR^b$ or $(NR^cR^d)^+X^-$;

when Y is —C=, Z is —$(CR^{13}{}_2)_2$— or —$CR^{14}$=$CR^{14}$— and $R^{12}$ is a bond; W is $N^+X^-$; or when Y is —C= and Z is absent; W is N or $(NR^a)^+X^-$;

$X^-$ is a pharmaceutically suitable counterion;

$Z^1$, $Z^2$, $Z^3$ and $Z^4$ are each independently O, S or $NR^e$; or $R^8$—$Z^1$—, $R^9$—$Z^2$—, $R^{10}$—$Z^3$—, and $R^{11}$—$Z^4$— can each independently be H, optionally substituted aryl or optionally substituted heteroaryl;

$R^1$ is H, $(C_1\text{-}C_6)$alkyl, $(C_1\text{-}C_6)$alkoxy, $(C_1\text{-}C_6)$alkylthio, aryloxy or arylthio; and $R^2$ is H or $(C_1\text{-}C_6)$alkyl, wherein any $(C_1\text{-}C_6)$alkyl, $(C_1\text{-}C_6)$alkoxy, and $(C_1\text{-}C_6)$alkylthio of $R^1$ and $R^2$ is optionally substituted with one or more groups selected from halo, cyano, oxo (=O), $(C_1\text{-}C_6)$alkyl, $(C_3\text{-}C_6)$cycloalkyl, carboxy, $NO_2$, hydroxy, $(C_1\text{-}C_6)$alkoxy, $(C_1\text{-}C_6)$alkoxycarbonyl, $(C_1\text{-}C_6)$alkanoyloxy, aryl, heteroaryl, aryloxy, heteroaryloxy, and —$NR^hR^i$, and wherein any aryloxy, or arylthio of $R^1$ and $R^2$ is optionally substituted with one or more groups selected from halo, cyano, $(C_1\text{-}C_6)$alkyl, $(C_3\text{-}C_6)$cycloalkyl, carboxy, $NO_2$, hydroxy, $(C_1\text{-}C_6)$alkoxy, $(C_1\text{-}C_6)$alkoxycarbonyl, $(C_1\text{-}C_6)$alkanoyloxy, aryl, heteroaryl, aryloxy, heteroaryloxy, and —$NR^hR^i$; or $R^1$ and $R^2$ together with the carbon to which they are attached form a carbonyl group;

at least one of $R^3$, $R^4$, $R^5$, $R^6$ and $R^7$ is hydroxyl, carboxy, cyano, alkoxy, $CF_3SO_3$—, alkyl, substituted alkyl, optionally substituted alkenyl, optionally substituted alkynyl, optionally substituted cycloalkyl, optionally substituted arylalkyl, optionally substituted heteroarylalkyl, optionally substituted aryl, optionally substituted arylalkanoyl, $R^k$, or optionally substituted heteroaryl, wherein substituted alkyl is an alkyl group with 1 to 5 substituent groups independently selected from cycloalkyl, substituted cycloalkyl, alkoxycarbonyl, cyano, halo, hydroxyl, oxo, carboxy, aryloxy, heteroaryloxy, heterocyclooxy, nitro, sulfo, —$S(O)_2NR''R^p$, —$N(R'')S(O)_2R^p$, and —$NR''R^p$, wherein $R''$ and $R^p$ may be the same or different and are chosen from hydrogen, alkyl, arylalkyl, heteroarylalkyl, cycloalkyl, substituted cycloalkyl, aryl, heteroaryl and heterocyclic; and the remainder of $R^3$, $R^4$, $R^5$, $R^6$ and $R^7$ are independently H, halo, nitro, sulfo, —$S(O)_2NR''R^p$, —$N(R'')S(O)_2R^p$, —$NR^hR^i$ optionally substituted alkyl, optionally substituted arylalkyl, optionally substituted heteroarylalkyl, optionally substituted aryl, or optionally substituted heteroaryl; or $R^3$ is —$Z^{13}$—$R^{13}$ wherein $Z^{13}$ is O, S or $NR^e$ and $R^{13}$ is $(C_1\text{-}C_6)$alkyl, substituted $(C_1\text{-}C_6)$alkyl, $(C_1\text{-}C_6)$alkanoyl or —C(=O)$NR^fR^g$ or $R^{13}$ and $R^9$ together with the atoms to which they are attached form a 5 to 7 membered ring; or $R^6$ and $R^7$ together with the atoms to which they are attached form a 5 to 6 membered heterocycle wherein the heterocycle is optionally fused with an optionally substituted aryl.

when Z is absent $R^{12}$ is H, alkyl, halo, —$NR^hR^i$, $NO_2$, aryl, heteroaryl, aryl$(C_1\text{-}C_6)$alkyl, heteroaryl$(C_1\text{-}C_6)$alkyl, aryl $(C_1\text{-}C_6)$alkanoyl or heteroaryl$(C_1\text{-}C_6)$alkanoyl wherein alkyl, aryl, heteroaryl, aryl$(C_1\text{-}C_6)$alkyl, heteroaryl$(C_1\text{-}C_6)$ alkyl, aryl$(C_1\text{-}C_6)$alkanoyl or heteroaryl$(C_1\text{-}C_6)$alkanoyl are optionally substituted with one or more groups selected from halo, cyano, $(C_1\text{-}C_6)$alkyl, $(C_3\text{-}C_6)$cycloalkyl, carboxy, $NO_2$, hydroxy, $(C_1\text{-}C_6)$alkoxy, $(C_1\text{-}C_6)$alkoxycarbonyl, $(C_1\text{-}C_6)$alkanoyloxy, aryl, heteroaryl, aryloxy, heteroaryloxy, and —$NR^hR^i$;

$R^8$ and $R^9$ are each independently, $(C_1\text{-}C_6)$alkyl, $(C_1\text{-}C_6)$ alkanoyl or —C(=O)$NR^fR^g$ or $R^8$ and $R^9$ together with the atoms to which they are attached form a 5 to 7 membered ring; or $R^8-Z^1-$ and $R^9-Z^2-$ can each independently be H;

$R^{10}$ and $R^{11}$ are each independently, $(C_1-C_6)$alkyl, $(C_1-C_6)$alkanoyl or $-C(=O)NR^fR^g$ or $R^{10}$ and $R^{11}$ together with the atoms to which they are attached form a 5 to 7 membered ring; or $R^{10}-Z^3-$, and $R^{11}-Z^4-$ can each independently be H;

each $R^{13}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{13}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^hR^i$, and wherein any aryloxy, or arylthio of $R^{13}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^hR^i$;

each $R^{14}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{14}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^hR^i$, and wherein any aryloxy, or arylthio of $R^{14}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^hR^i$;

$R^a$ is $(C_1-C_6)$alkyl wherein $(C_1-C_6)$alkyl is optionally substituted with one or more groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^hR^i$;

$R^b$ is H or $(C_1-C_6)$alkyl wherein $(C_1-C_6)$alkyl is optionally substituted with one or more groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^hR^i$;

$R^c$ and $R^d$ are each independently selected from $(C_1-C_6)$alkyl wherein $(C_1-C_6)$alkyl is optionally substituted with one or more groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^hR^i$;

each $R^e$ is independently H or $(C_1-C_6)$alkyl wherein $(C_1-C_6)$alkyl is optionally substituted with one or more halo;

$R^f$ and $R^g$ are each independently H, $(C_1-C_6)$alkyl, aryl, heteroaryl, aryl($C_1-C_6$) alkyl or heteroaryl($C_1-C_6$) alkyl; or $R^f$ and $R^g$ together with the nitrogen to which they are attached form a morpholino, piperazino, pyrrolidino or piperidino;

$R^h$ and $R^i$ are each independently H, $(C_1-C_6)$alkyl, aryl, heteroaryl, aryl($C_1-C_6$) alkyl or heteroaryl($C_1-C_6$) alkyl; or $R^h$ and $R^i$ together with the nitrogen to which they are attached form a morpholino, piperazino, pyrrolidino or piperidino;

each $R^k$ is independently selected from an aryl optionally substituted with one or more $R^m$, an alkyl substituted with one or more heterocycle, and an alkyl substituted with one or more substituted heterocycle;

each $R^m$ is independently, alkoxy, substituted alkoxy, heteroaryl, heterocycle, or $-S(O)_2NR^uR^v$; and each $R^u$ and $R^v$ is independently H, $(C_1-C_6)$alkyl, aryl, heteroaryl, aryl($C_1-C_6$)alkyl, or heteroaryl($C_1-C_6$)alkyl; or $R^m$ and $R^n$ together with the nitrogen to which they are attached form a morpholino, piperazino, pyrrolidino or piperidino;

or a salt or prodrug thereof.

The invention also provides a pharmaceutical composition comprising a compound of formula I, or a pharmaceutically acceptable salt or prodrug thereof, and a pharmaceutically acceptable excipient, diluent or carrier.

The invention also provides a method for treating a bacterial infection caused by, e.g. a Gram-negative bacterial strain, a Gram-positive bacterial strain or a multiple drug-resistant bacterial strain, in a mammal (e.g. a human) comprising administering to the mammal an effective amount of a compound of formula I, or a pharmaceutically acceptable salt or prodrug thereof.

The invention also provides a compound of formula I, or a pharmaceutically acceptable salt or prodrug thereof, for use in medical therapy.

The invention also provides the use of a compound of formula I or a pharmaceutically acceptable salt or prodrug thereof for the manufacture of a medicament useful for treating a bacterial infection (e.g. a Gram-negative bacterial strain, a Gram-positive bacterial strain or a multiple drug-resistant bacterial strain) in a mammal (e.g. a human).

The invention also provides a compound of formula I or a pharmaceutically acceptable salt or prodrug thereof for use in the prophylactic or therapeutic treatment of a bacterial infection (e.g. a Gram-negative bacterial strain, a Gram-positive bacterial strain or a multiple drug-resistant bacterial strain) in a mammal (e.g. a human).

The invention also provides a method for inhibiting FtsZ polymerization in a mammal (e.g. a human) in need of such treatment comprising administering to the mammal, an amount of a compound of formula I, or a pharmaceutically acceptable salt or prodrug thereof, effective to inhibit FtsZ polymerization.

The invention also provides a method for inhibiting FtsZ Z-ring formation in a mammal (e.g. a human) in need of such treatment comprising administering to the mammal, an amount of a compound of formula I, or a pharmaceutically acceptable salt or prodrug thereof, effective to inhibit FtsZ Z-ring formation.

The invention also provides a method for inhibiting the recruitment of divisome proteins in a mammal (e.g. a human) in need of such treatment comprising administering to the mammal, an amount of a compound of formula I, or a pharmaceutically acceptable salt or prodrug thereof, effective to inhibit the recruitment of divisome proteins.

The invention also provides a method for inhibiting FtsZ polymerization in a bacterium in a mammal (e.g. a human) in need of such treatment comprising administering to the mammal, an amount of a compound of formula I, or a pharmaceutically acceptable salt or prodrug thereof, effective to inhibit FtsZ polymerization.

The invention also provides a method for inhibiting FtsZ Z-ring formation in a bacterium in a mammal (e.g. a human) in need of such treatment comprising administering to the mammal, an amount of a compound of formula I, or a pharmaceutically acceptable salt or prodrug thereof, effective to inhibit FtsZ Z-ring formation.

The invention also provides a method for inhibiting the recruitment of divisome proteins in a bacterium in a mammal (e.g. a human) in need of such treatment comprising administering to the mammal, an amount of a compound of formula I, or a pharmaceutically acceptable salt or prodrug thereof, effective to inhibit the recruitment of divisome proteins.

The invention also provides a method for inhibiting FtsZ polymerization in a bacterium comprising contacting the bacterium with an amount of a compound of formula I, or a pharmaceutically acceptable salt or prodrug thereof, effective to inhibit FtsZ polymerization.

The invention also provides a method for inhibiting FtsZ Z-ring formation in a bacterium comprising contacting the bacterium with an amount of a compound of formula I, or a pharmaceutically acceptable salt or prodrug thereof, effective to inhibit FtsZ Z-ring formation.

The invention also provides a method for inhibiting the recruitment of divisome proteins in a bacterium comprising contacting the bacterium with an amount of a compound of formula, or a pharmaceutically acceptable salt or prodrug thereof, effective to inhibit the recruitment of divisome proteins.

The invention also provides the use of a compound of formula I or a pharmaceutically acceptable salt or prodrug thereof for the manufacture of a medicament useful for inhibiting FtsZ polymerization in a bacterium in a mammal (e.g. a human).

The invention also provides the use of a compound of formula I or a pharmaceutically acceptable salt or prodrug thereof for the manufacture of a medicament useful for inhibiting FtsZ polymerization in a mammal (e.g. a human).

The invention also provides the use of a compound of formula I or a pharmaceutically acceptable salt or prodrug thereof for the manufacture of a medicament useful for inhibiting FtsZ Z-ring formation in a bacterium in a mammal (e.g. a human).

The invention also provides the use of a compound of formula I or a pharmaceutically acceptable salt or prodrug thereof for the manufacture of a medicament useful for inhibiting FtsZ Z-ring formation in a mammal (e.g. a human).

The invention also provides the use of a compound of formula I or a pharmaceutically acceptable salt or prodrug thereof for the manufacture of a medicament useful for inhibiting the recruitment of divisome proteins in a bacterium in a mammal (e.g. a human).

The invention also provides the use of a compound of formula I or a pharmaceutically acceptable salt or prodrug thereof for the manufacture of a medicament useful for inhibiting the recruitment of divisome proteins in a mammal (e.g. a human).

The invention also provides a compound of formula I or a pharmaceutically acceptable salt or prodrug thereof for use in the prophylactic or therapeutic treatment of a condition or symptom in a mammal (e.g. a human) wherein the inhibition of FtsZ polymerization is desired.

The invention also provides a compound of formula I or a pharmaceutically acceptable salt or prodrug thereof for use in the prophylactic or therapeutic treatment of a condition or symptom in a mammal (e.g. a human) wherein the inhibition of FtsZ Z-ring formation is desired.

The invention also provides a compound of formula I or a pharmaceutically acceptable salt or prodrug thereof for use in the prophylactic or therapeutic treatment of a condition or symptom in a mammal (e.g. a human) wherein the inhibition of the recruitment of divisome proteins is desired.

The invention also provides processes and intermediates disclosed herein that are useful for preparing compounds of formula I or salts thereof.

DETAILED DESCRIPTION

The following definitions are used, unless otherwise described: halo is fluoro, chloro, bromo, or iodo. Alkyl, alkenyl, alkynyl and alkoxy, etc. denote both straight and branched groups but reference to an individual radical such as propyl embraces only the straight chain radical (a branched chain isomer such as isopropyl being specifically referred to). In one embodiment alkyl is a $(C_1-C_6)$alkyl, alkenyl is a $(C_2-C_6)$alkenyl, alkynyl is a $(C_2-C_6)$alkynyl and alkoxy is a $(C_1-C_6)$alkoxy. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(Q) wherein Q is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(Q).

The term "heterocycle" as used herein refers to a single saturated or partially unsaturated ring (e.g. 3, 4, 5, 6, 7 or 8-membered ring) from about 1 to 7 carbon atoms and from about 1 to 3 heteroatoms selected from the group consisting of oxygen, nitrogen and sulfur in the rings. The sulfur and nitrogen atoms may also be present in their oxidized forms. Such rings include but are not limited to azetidinyl, tetrahydrofuranyl or piperidinyl.

As used herein "cycloalkyl" refers to a saturated or partially unsaturated cyclic hydrocarbon ring system. In one embodiment "cycloalkyl" includes $(C_3-C_6)$cycloalkyl which can be cyclopropyl, cyclobutyl, cyclopentyl, or cyclohexyl.

As used herein, "optionally substituted alkyl" is an alkyl group, as defined above that is optionally substituted with 1 to 5 groups independently selected from: optionally substituted cycloalkyl, alkoxycarbonyl (e.g. —$CO_2Me$), cyano, halo, hydroxyl, oxo (=O), carboxy (COOH), aryloxy, heteroaryloxy, heterocyclooxy, nitro, and —$NR^aR^b$, wherein $R^a$ and $R^b$ may be the same or different and are chosen from hydrogen, alkyl, arylalkyl, heteroarylalkyl, optionally substituted cycloalkyl, aryl, heteroaryl and heterocyclic; or where $R^a$ and $R^b$ taken together with the nitrogen to which they are attached form a piperazino, pyrrolidino, piperidino, morpholino, or thiomorpholino ring.

As used herein, "optionally substituted alkenyl" is an alkenyl group that is optionally substituted with 1 to 5 groups independently selected from: optionally substituted cycloalkyl, alkoxycarbonyl (e.g. —$CO_2Me$), cyano, halo, hydroxyl, oxo (=O), carboxy (COOH), aryloxy, heteroaryloxy, heterocyclooxy, nitro, and —$NR^aR^b$, wherein $R^a$ and $R^b$ may be the same or different and are chosen from hydrogen, alkyl, arylalkyl, heteroarylalkyl, optionally substituted cycloalkyl, aryl, heteroaryl and heterocyclic; or where $R^a$ and $R^b$ taken together with the nitrogen to which they are attached form a piperazino, pyrrolidino, piperidino, morpholino, or thiomorpholino ring.

As used herein, "optionally substituted alkynyl" is an alkynyl group that is optionally substituted with 1 to 5 groups independently selected from: optionally substituted cycloalkyl, alkoxycarbonyl (e.g. —$CO_2Me$), cyano, halo, hydroxyl, oxo (=O), carboxy (COOH), aryloxy, heteroaryloxy, heterocyclooxy, nitro, and —$NR^aR^b$, wherein $R^a$ and $R^b$ may be the same or different and are chosen from hydrogen, alkyl, arylalkyl, heteroarylalkyl, optionally substituted cycloalkyl, aryl, heteroaryl and heterocyclic; or where $R^a$ and $R^b$ taken together with the nitrogen to which they are attached form a piperazino, pyrrolidino, piperidino, morpholino, or thiomorpholino ring.

As used herein, "optionally substituted cycloalkyl" is a cycloalkyl group that is optionally substituted with 1 to 5 groups independently selected from: optionally substituted cycloalkyl, alkoxycarbonyl (e.g. —CO$_2$Me), cyano, halo, hydroxyl, oxo (═O), carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, optionally substituted cycloalkyl, aryl, heteroaryl and heterocyclic; or where R$^a$ and R$^b$ taken together with the nitrogen to which they are attached form a piperazino, pyrrolidino, piperidino, morpholino, or thiomorpholino ring.

As used herein, "an optionally substituted aryl group" denotes an aryl group that is optionally substituted with 1 to 5 substituent groups independently selected from: optionally substituted alkyl, optionally substituted cycloalkyl, alkoxycarbonyl (e.g. —CO$_2$Me), cyano, halo, hydroxyl, carboxy (COOH), aryl, aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, cycloalkyl, substituted cycloalkyl, aryl, heteroaryl and heterocyclic; or where R$^a$ and R$^b$ taken together with the nitrogen to which they are attached form a piperazino, pyrrolidino, piperidino, morpholino, or thiomorpholino ring. In one specific embodiment of the invention "an optionally substituted aryl group" denotes an aryl group that is substituted with 1 to 5 substituent groups independently selected from: cycloalkyl, substituted cycloalkyl, alkoxycarbonyl (e.g. —CO$_2$Me), cyano, halo, hydroxyl, carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, optionally substituted cycloalkyl, aryl, heteroaryl and heterocyclic; or where R$^a$ and R$^b$ taken together with the nitrogen to which they are attached form a piperazino, pyrrolidino, piperidino, morpholino, or thiomorpholino ring.

As used herein, "an optionally substituted heteroaryl group" denotes a heteroaryl group that is optionally substituted with 1 to 5 substituent groups independently selected from: optionally substituted alkyl, optionally substituted cycloalkyl, alkoxycarbonyl (e.g. —CO$_2$Me), cyano, halo, hydroxyl, carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl optionally substituted cycloalkyl, aryl, heteroaryl and heterocyclic; or where R$^a$ and R$^b$ taken together with the nitrogen to which they are attached form a piperazino, pyrrolidino, piperidino, morpholino, or thiomorpholino ring.

As used herein, "an optionally substituted arylalkyl" denotes an aryl-alkyl- group wherein the aryl group is an optionally substituted aryl and the alkyl is an optionally substituted alkyl.

As used herein, "an optionally substituted heteroarylalkyl" denotes a heteroaryl-alkyl- group wherein the heteroaryl group is an optionally substituted heteroaryl and the alkyl is an optionally substituted alkyl.

As used herein, "an optionally substituted arylalkanoyl" denotes an aryl-alkyl-C(═O)— group wherein the aryl group is an optionally substituted aryl and the alkyl is an optionally substituted alkyl.

As used herein, "an optionally substituted alkoxy" denotes an alkyl-O— group wherein the alkyl group is an optionally substituted alkyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, stereoisomeric, or polymorphic form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific values listed below for radicals, substituents, and ranges, are for illustration only; they do not exclude other defined values or other values within defined ranges for the radicals and substituents.

Specifically, (C$_1$-C$_6$)alkyl can be methyl, ethyl, propyl, isopropyl, butyl, iso-butyl, sec-butyl, pentyl, 3-pentyl, or hexyl; (C$_3$-C$_6$)cycloalkyl can be cyclopropyl, cyclobutyl, cyclopentyl, or cyclohexyl; (C$_1$-C$_6$)alkoxy can be methoxy, ethoxy, propoxy, isopropoxy, butoxy, iso-butoxy, sec-butoxy, pentoxy, 3-pentoxy, or hexyloxy; (C$_1$-C$_6$)alkanoyl can be formyl, acetyl, propanoyl, butanoyl, pentanoyl, or hexanoyl; (C$_1$-C$_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; (C$_1$-C$_6$)alkylthio can be methylthio, ethylthio, propylthio, isopropylthio, butylthio, isobutylthio, pentylthio, or hexylthio; (C$_2$-C$_6$)alkanoyloxy can be acetoxy, propanoyloxy, butanoyloxy, isobutanoyloxy, pentanoyloxy, or hexanoyloxy; aryl can be phenyl, indenyl, or naphthoyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, benximidazole, isoquinolyl (or its N-oxide) or quinolyl (or its N-oxide).

As used herein the term "aryl(C$_1$-C$_6$)alkyl" refers to a (C$_1$-C$_6$)alkyl radical in which one or more of the hydrogen atoms of the (C$_1$-C$_6$)alkyl radical is replaced with an aryl radical. As used herein the term "heteroaryl(C$_1$-C$_6$) alkyl" refers to a (C$_1$-C$_6$)alkyl radical in which one or more of the hydrogen atoms of the (C$_1$-C$_6$)alkyl radical is replaced with a heteroaryl radical.

As used herein, "an aryl(C$_1$-C$_6$)alkanoyl group" refers to a group of the formula aryl-(C$_1$-C$_6$)alkanoyl-, where aryl and (C$_1$-C$_6$)alkanoyl are defined herein. Such aryl(C$_1$-C$_6$)alkanoyl groups may include, but are not limited to, benzoyl, 4-phenylbenzoyl, and naphthoyl, and the like. As used herein, "an heteroaryl(C$_1$-C$_6$)alkanoyl group" refers to a group of the formula heteroaryl-(C$_1$-C$_6$)alkanoyl-, where heteroaryl and (C$_1$-C$_6$)alkanoyl are defined herein.

As used herein, "an aryloxy group" refers to a group of the formula aryl-O—, where aryl is as defined herein. Such aryloxy groups may include, but are not limited to, phenoxy, 4-phenylphenoxy, and naphthyloxy, and the like. As used herein, "an arylthio group" refers to a group of the formula aryl-S—, where aryl is as defined herein. Such arylthio groups may include, but are not limited to, phenylthio, 4-phenylphenylthio, and naphthylthio, and the like. As used herein, "a heteroaryloxy group" refers to a group of the formula heteroaryl-O—, where heteroaryl is as defined herein.

By binding to FtsZ, the compounds of the present invention inhibit the ability of the protein to hydrolyze GTP. This inhibition of FtsZ GTPase activity, in turn, inhibits the ability of the protein to polymerize into Z-rings, as Z-ring formation requires GTP hydrolysis as an energy source for driving the reaction. Since the Z-ring serves as the scaffold for recruitment of all other proteins that comprise the divisome complex, inhibition of Z-ring formation by the compounds of the present invention also results in a corresponding inhibition of divisome protein recruitment.

A specific compound of formula I is a compound wherein:
the dashed line between Y and W represents a single or double bond;
when Y is —$CR^2$—, Z is —$(CR^{13}_2)_2$— or —$CR^{14}$=$C^{14}$— and $R^{12}$ is a bond; W is N or $(NR^a)^+X^-$;
when Y is —$CR^2$— and Z is absent; W is $NR^b$ or $(NR^cR^d)^+X^-$;
when Y is —C=, Z is —$(CR^{13}_2)_2$— or —$CR^{14}$=$CR^{14}$— and $R^{12}$ is a bond; W is $N^+X^-$;
when Y is —C= and Z is absent; W is N or $(NR^a)^+X^-$;
$X^-$ is a pharmaceutically suitable counterion;
$Z^1$, $Z^2$, $Z^3$ and $Z^4$ are each independently O, S or $NR^e$;
$R^1$ is H, $(C_1-C_6)$alkyl, $(C_1-C_6)$alkoxy, $(C_1-C_6)$alkylthio, aryloxy or arylthio; and $R^2$ is H or $(C_1-C_6)$alkyl, wherein any $(C_1-C_6)$alkyl, $(C_1-C_6)$alkoxy, and $(C_1-C_6)$alkylthio of $R^1$ and $R^2$ is optionally substituted with one or more (e.g. 1, 2, 3, or 4) groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^1$ and $R^2$ is optionally substituted with one or more (e.g. 1, 2, 3, or 4) groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$; or $R^1$ and $R^2$ together with the carbon to which they are attached form a carbonyl group;
at least one of $R^3$, $R^4$, $R^5$, $R^6$ and $R^7$ is aryl, heteroaryl, aryl($C_1-C_6$)alkyl, heteroaryl($C_1-C_6$)alkyl, aryl($C_1-C_6$)alkanoyl or heteroaryl($C_1-C_6$)alkanoyl and the remainder are each independently H, alkyl, halo, —$NR^hR^i$, $NO_2$, aryl, heteroaryl, aryl($C_1-C_6$)alkyl, heteroaryl($C_1-C_6$)alkyl, aryl($C_1-C_6$)alkanoyl or heteroaryl($C_1-C_6$)alkanoyl wherein the alkyl, aryl, heteroaryl, aryl($C_1-C_6$)alkyl, heteroaryl($C_1-C_6$)alkyl, aryl($C_1-C_6$)alkanoyl or heteroaryl($C_1-C_6$)alkanoyl of $R^3$, $R^4$, $R^5$, $R^6$ and $R^7$ is optionally substituted with one or more (e.g. 1, 2, 3, or 4) groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;
when Z is absent $R^{12}$ is H, alkyl, halo, —$NR^hR^i$, $NO_2$, aryl, heteroaryl, aryl($C_1-C_6$)alkyl, heteroaryl($C_1-C_6$)alkyl, aryl($C_1-C_6$)alkanoyl or heteroaryl($C_1-C_6$)alkanoyl wherein alkyl, aryl, heteroaryl, aryl($C_1-C_6$)alkyl, heteroaryl($C_1-C_6$)alkyl, aryl($C_1-C_6$)alkanoyl or heteroaryl($C_1-C_6$)alkanoyl are optionally substituted with one or more (e.g. 1, 2, 3, or 4) groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;
$R^8$ and $R^9$ are each independently, $(C_1-C_6)$alkyl, $(C_1-C_6)$alkanoyl or —C(=O)$NR^fR^g$ or $R^8$ and $R^9$ together with the atoms to which they are attached form a 5 to 7 membered ring;
$R^{10}$ and $R^{11}$ are each independently, $(C_1-C_6)$alkyl, $(C_1-C_6)$alkanoyl or —C(=O)$NR^fR^g$ or $R^{10}$ and $R^{11}$ together with the atoms to which they are attached form a 5 to 7 membered ring;
each $R^{13}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{13}$ is optionally substituted with one or more (e.g. 1, 2, 3, or 4) groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^{13}$ is optionally substituted with one or more (e.g. 1, 2, 3, or 4) groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;
each $R^{14}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{14}$ is optionally substituted with one or more (e.g. 1, 2, 3, or 4) groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^{14}$ is optionally substituted with one or more (e.g. 1, 2, 3, or 4) groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;
$R^a$ is $(C_1-C_6)$alkyl wherein $(C_1-C_6)$alkyl is optionally substituted with one or more (e.g. 1, 2, 3, or 4) groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;
$R^b$ is H or $(C_1-C_6)$alkyl wherein $(C_1-C_6)$alkyl is optionally substituted with one or more (e.g. 1, 2, 3, or 4) groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;
$R^c$ and $R^d$ are each independently selected from $(C_1-C_6)$alkyl wherein $(C_1-C_6)$alkyl is optionally substituted with one or more (e.g. 1, 2, 3, or 4) groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;
each $R^e$ is independently H or $(C_1-C_6)$alkyl wherein $(C_1-C_6)$alkyl is optionally substituted with one or more (e.g. 1, 2, 3, or 4) halo;
$R^f$ and $R^g$ are each independently H, $(C_1-C_6)$alkyl, aryl, heteroaryl, aryl($C_1-C_6$) alkyl or heteroaryl($C_1-C_6$) alkyl; or $R^f$ and $R^g$ together with the nitrogen to which they are attached form a morpholino, piperazino, pyrrolidino or piperidino; and
$R^h$ and $R^i$ are each independently H, $(C_1-C_6)$alkyl, aryl, heteroaryl, aryl($C_1-C_6$) alkyl or heteroaryl($C_1-C_6$) alkyl; or $R^f$ and $R^g$ together with the nitrogen to which they are attached form a morpholino, piperazino, pyrrolidino or piperidino;
or a pharmaceutically acceptable salt or prodrug thereof.

A specific group of compounds of formula 1 are compounds of formula Ia:

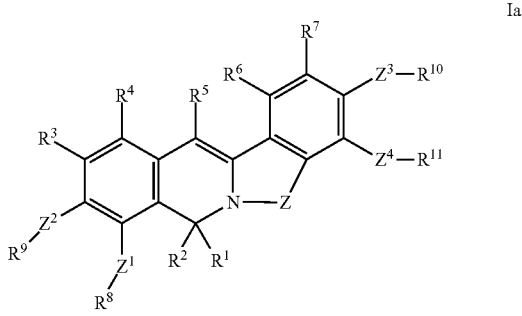

Ia

Another specific group of compounds of formula 1 are compounds of formula Ib:

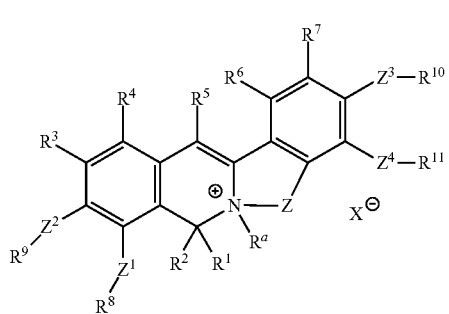

Ib

Another specific group of compounds of formula 1 are compounds of formula Ic:

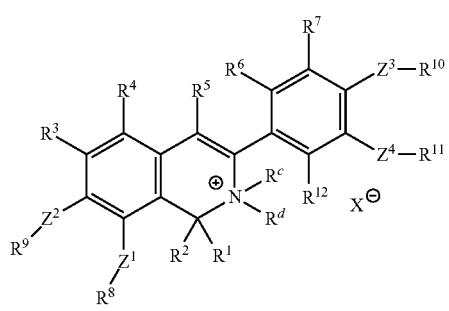

Ic

Another specific group of compounds of formula 1 are compounds of formula Id:

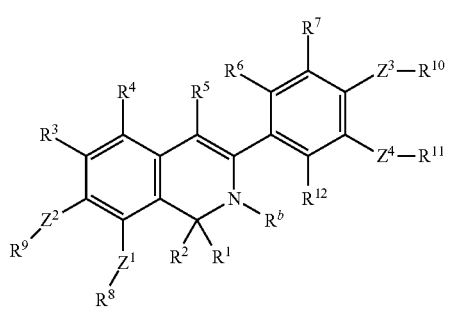

Id

Another specific group of compounds of formula 1 are compounds of formula Ie:

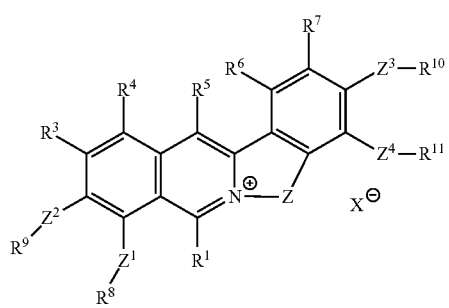

Ie

Another specific group of compounds of formula 1 are compounds of formula If:

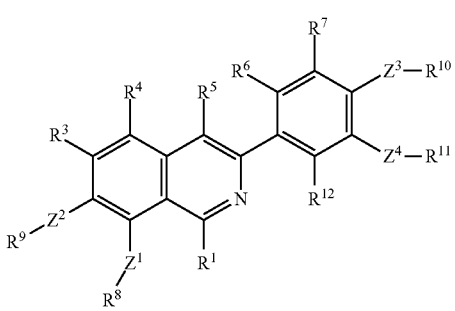

If

Another specific group of compounds of formula 1 are compounds of formula Ig:

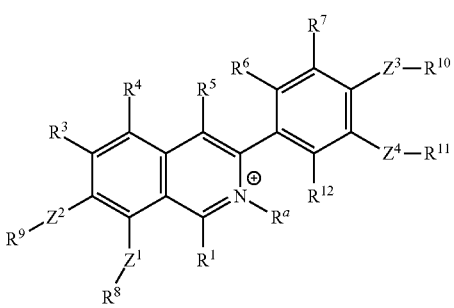

Ig

Another specific group of compounds of formula 1 are compounds of formula Ih:

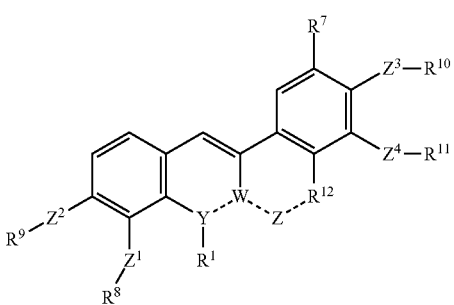

Ih

Another specific group of compounds of formula 1 are compounds of formula Ij:

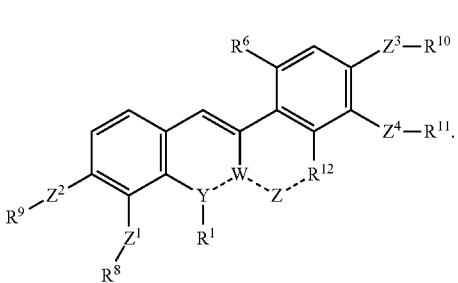

Ij

Another specific group of compounds of formula 1 are compounds of formula Ik:

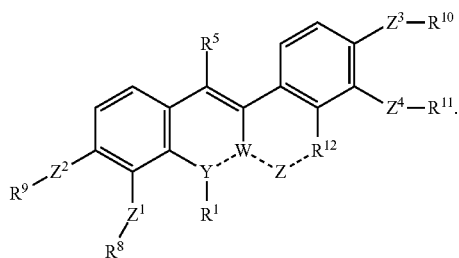

Another specific group of compounds of formula 1 are compounds of formula Im:

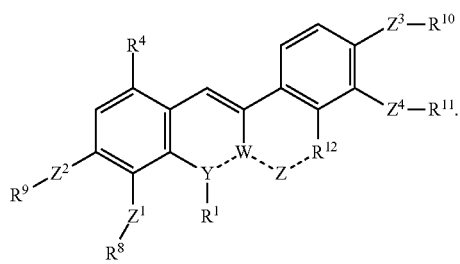

Another specific group of compounds of formula 1 are compounds of formula In:

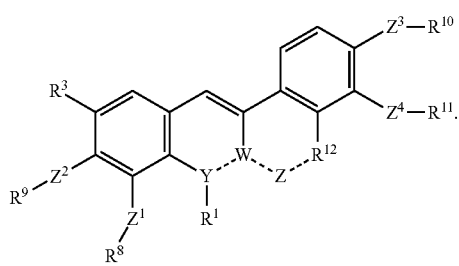

Another specific group of compounds of formula 1 are compounds of Ip:

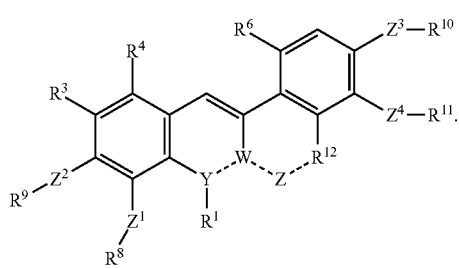

Another specific group of compounds of formula 1 are compounds of formula Ir:

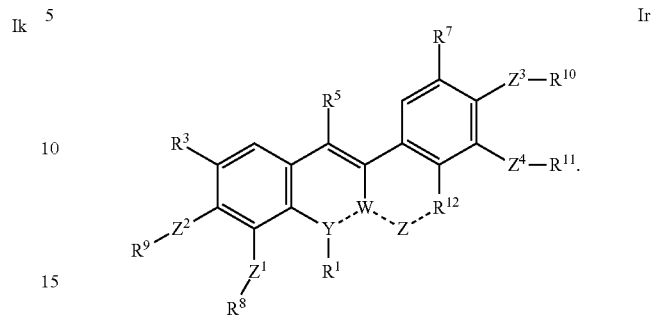

A specific value for $R^a$ is $(C_1\text{-}C_6)$alkyl.
Another specific value $R^a$ is $CH_3$.
A specific value for $R^b$ is $(C_1\text{-}C_6)$alkyl.
Another specific value $R^b$ is $CH_3$.
A specific group of compounds of formula I are compounds wherein $R^c$ and $R^d$ are each independently $(C_1\text{-}C_6)$alkyl.
Another specific group of compounds of formula I are compounds wherein $R^c$ and $R^d$ are each $CH_3$.
A specific group of compounds of formula I are compounds wherein $Z^1$ and $Z^2$ are O.
A specific group of compounds of formula I are compounds wherein $R^8$ and $R^9$ are $(C_1\text{-}C_6)$alkyl.
Another specific group of compounds of formula I are compounds wherein $R^8$ and $R^9$ are $CH_3$.
Another specific group of compounds of formula I are compounds wherein $R^8$ and $R^9$ together with atoms to which they are attached form a five-membered ring.
Another specific group of compounds of formula I are compounds wherein $R^8$, $R^9$, $Z^1$ and $Z^2$ form a methylenedioxy, which when taken together with atoms to which they are attached form a five-membered ring.
A specific group of compounds of formula I are compounds wherein $Z^3$ and $Z^4$ are O.
A specific group of compounds of formula I are compounds wherein $R^{10}$ and $R^{11}$ are $(C_1\text{-}C_6)$alkyl.
Another specific group of compounds of formula I are compounds wherein $R^{10}$ and $R^{11}$ are $CH_3$.
Another specific group of compounds of formula I are compounds wherein $R^{10}$ and $R^{11}$ together with the atoms to which they are attached form a five-membered ring.
Another specific group of compounds of formula I are compounds wherein $R^{10}$, $R^{11}$, $Z^3$ and $Z^4$ form a methylenedioxy, which when taken together with atoms to which they are attached form a five-membered ring.
A specific group of compounds of formula I are compounds wherein $R^1$ and $R^2$ are each independently H.
Another specific group of compounds of formula I are compounds wherein $R^1$ and $R^2$ together with the carbon to which they are attached form a carbonyl group.
In one embodiment at least one of $R^3$, $R^4$, $R^5$, $R^6$ and $R^7$ is aryl, heteroaryl, aryl$(C_1\text{-}C_6)$alkyl or aryl$(C_1\text{-}C_6)$alkanoyl wherein aryl, heteroaryl, aryl$(C_1\text{-}C_6)$alkyl or aryl$(C_1\text{-}C_6)$alkanoyl are optionally substituted with one or more (e.g. 1, 2, 3, or 4) groups selected from halo, cyano, $(C_1\text{-}C_6)$alkyl, $(C_3\text{-}C_6)$cycloalkyl, carboxy, $NO_2$, hydroxy, $(C_1\text{-}C_6)$alkoxy, $(C_1\text{-}C_6)$alkoxycarbonyl, $(C_1\text{-}C_6)$alkanoyloxy, aryl, heteroaryl, aryloxy, heteroaryloxy, and $-NR^hR^i$.

In another embodiment at least one of $R^3, R^4, R^5, R^6$ and $R^7$ is benzyl.

In another embodiment at least one of $R^3, R^4, R^5, R^6$ and $R^7$ is benzimidazolyl (e.g. benzimidazol-5-yl)

In another embodiment at least one of $R^3, R^4, R^5, R^6$ and $R^7$ is 1,1'-biphenyl-4-yl.

In another embodiment at least one of $R^3, R^4, R^5, R^6$ and $R^7$ is benzoyl.

In another embodiment $Z^{13}$ is O and $R^{13}$ is $(C_1-C_6)$alkyl.

In another embodiment $R^3$ is methoxy.

In one embodiment at least one of $R^3, R^4, R^5, R^6$ and $R^7$ is hydroxyl, carboxy, cyano, alkoxy, $CF_3SO_3$—, $(C_2-C_8)$alkyl, substituted alkyl, optionally substituted alkenyl, optionally substituted alkynyl, optionally substituted cycloalkyl, optionally substituted arylalkyl, optionally substituted heteroarylalkyl, optionally substituted aryl, optionally substituted arylalkanoyl, $R^k$, or optionally substituted heteroaryl, wherein substituted alkyl is an alkyl group with 1 to 5 substituent groups independently selected from cycloalkyl, substituted cycloalkyl, alkoxycarbonyl, cyano, halo, hydroxyl, oxo, carboxy, aryloxy, heteroaryloxy, heterocyclooxy, nitro, sulfo, —$S(O)_2NR''R^p$, —$N(R'')S(O)_2R^p$, and —$NR''R^p$, wherein $R''$ and $R^p$ may be the same or different and are chosen from hydrogen, alkyl, arylalkyl, heteroarylalkyl, cycloalkyl, substituted cycloalkyl, aryl, heteroaryl and heterocyclic; and the remainder of $R^3, R^4, R^5, R^6$ and $R^7$ are independently H, halo, nitro, sulfo, —$S(O)_2NR''R^p$, —$N(R'')S(O)_2R^p$, —$NR^hR^i$ optionally substituted alkyl, optionally substituted arylalkyl, optionally substituted heteroarylalkyl, optionally substituted aryl, or optionally substituted heteroaryl; or $R^3$ is —$Z^{13}$—$R^{13}$ wherein $Z^{13}$ is O, S or $NR^e$ and $R^{13}$ is $(C_1-C_6)$alkyl, substituted $(C_1-C_6)$alkyl, $(C_1-C_6)$alkanoyl or —$C(=O)NR^fR^g$ or $R^{13}$ and $R^9$ together with the atoms to which they are attached form a 5 to 7 membered ring; or $R^6$ and $R^7$ together with the atoms to which they are attached form a 5 to 6 membered heterocycle wherein the heterocycle is optionally fused with an optionally substituted aryl.

In another embodiment at least one of $R^3, R^4, R^5, R^6$ and $R^7$ is hydroxyl, carboxy, cyano, alkoxy, $CF_3SO_3$—, $(C_3-C_8)$ alkyl, substituted alkyl, optionally substituted alkenyl, optionally substituted alkynyl, optionally substituted cycloalkyl, optionally substituted arylalkyl, optionally substituted heteroarylalkyl, optionally substituted aryl, optionally substituted arylalkanoyl, $R^k$, or optionally substituted heteroaryl, wherein substituted alkyl is an alkyl group with 1 to 5 substituent groups independently selected from cycloalkyl, substituted cycloalkyl, alkoxycarbonyl, cyano, halo, hydroxyl, oxo, carboxy, aryloxy, heteroaryloxy, heterocyclooxy, nitro, sulfo, —$S(O)_2NR''R^p$, —$N(R'')S(O)_2R^p$, and —$NR''R^p$, wherein $R''$ and $R^p$ may be the same or different and are chosen from hydrogen, alkyl, arylalkyl, heteroarylalkyl, cycloalkyl, substituted cycloalkyl, aryl, heteroaryl and heterocyclic; and the remainder of $R^3, R^4, R^5, R^6$ and $R^7$ are independently H, halo, nitro, sulfo, —$S(O)_2NR''R^p$, —$N(R'')S(O)_2R^p$, —$NR^hR^i$ optionally substituted alkyl, optionally substituted arylalkyl, optionally substituted heteroarylalkyl, optionally substituted aryl, or optionally substituted heteroaryl; or $R^3$ is —$Z^{13}$—$R^{13}$ wherein $Z^{13}$ is O, S or $NR^e$ and $R^{13}$ is $(C_1-C_6)$alkyl, substituted $(C_1-C_6)$alkyl, $(C_1-C_6)$alkanoyl or —$C(=O)NR^fR^g$ or $R^{13}$ and $R^9$ together with the atoms to which they are attached form a 5 to 7 membered ring; or $R^6$ and $R^7$ together with the atoms to which they are attached form a 5 to 6 membered heterocycle wherein the heterocycle is optionally fused with an optionally substituted aryl.

In another embodiment at least one of $R^3, R^4, R^5, R^6$ and $R^7$ is hydroxyl, carboxy, cyano, alkoxy, $CF_3SO_3$—, substituted alkyl, optionally substituted alkenyl, optionally substituted alkynyl, optionally substituted cycloalkyl, optionally substituted arylalkyl, optionally substituted heteroarylalkyl, optionally substituted aryl, optionally substituted arylalkanoyl, $R^k$, or optionally substituted heteroaryl, wherein substituted alkyl is an alkyl group with 1 to 5 substituent groups independently selected from cycloalkyl, substituted cycloalkyl, alkoxycarbonyl, cyano, halo, hydroxyl, oxo, carboxy, aryloxy, heteroaryloxy, heterocyclooxy, nitro, sulfo, —$S(O)_2NR''R^p$, —$N(R'')S(O)_2R^p$, and —$NR''R^p$, wherein $R''$ and $R^p$ may be the same or different and are chosen from hydrogen, alkyl, arylalkyl, heteroarylalkyl, cycloalkyl, substituted cycloalkyl, aryl, heteroaryl and heterocyclic; and the remainder of $R^3, R^4, R^5, R^6$ and $R^7$ are independently H, halo, nitro, sulfo, —$S(O)_2NR''R^p$, —$N(R'')S(O)_2R^p$, —$NR^hR^i$ optionally substituted alkyl, optionally substituted arylalkyl, optionally substituted heteroarylalkyl, optionally substituted aryl, or optionally substituted heteroaryl; or $R^3$ is —$Z^{13}$—$R^{13}$ wherein $Z^{13}$ is O, S or $NR^e$ and $R^{13}$ is $(C_1-C_6)$alkyl, substituted $(C_1-C_6)$alkyl, $(C_1-C_6)$alkanoyl or —$C(=O)NR^fR^g$ or $R^{13}$ and $R^9$ together with the atoms to which they are attached form a 5 to 7 membered ring.

In another embodiment at least one of $R^3, R^4, R^5, R^6$ and $R^7$ is a substituted alkyl, optionally substituted alkenyl, optionally substituted alkynyl, optionally substituted cycloalkyl, optionally substituted arylalkyl, optionally substituted heteroarylalkyl, optionally substituted aryl, optionally substituted arylalkanoyl, $R^k$, or optionally substituted heteroaryl, wherein substituted alkyl is an alkyl group with 1 to 5 substituent groups independently selected from cycloalkyl, substituted cycloalkyl, alkoxycarbonyl, cyano, halo, hydroxyl, oxo, carboxy, aryloxy, heteroaryloxy, heterocyclooxy, nitro, sulfo, —$S(O)_2NR''R^p$, —$N(R'')S(O)_2R^p$, and —$NR''R^p$, wherein $R''$ and $R^p$ may be the same or different and are chosen from hydrogen, alkyl, arylalkyl, heteroarylalkyl, cycloalkyl, substituted cycloalkyl, aryl, heteroaryl and heterocyclic; and the remainder of $R^3, R^4, R^5, R^6$ and $R^7$ are independently H, halo, nitro, sulfo, —$S(O)_2NR''R^p$, —$N(R'')$ $S(O)_2R^p$, —$NR^hR^i$ optionally substituted alkyl, optionally substituted arylalkyl, optionally substituted heteroarylalkyl, optionally substituted aryl, or optionally substituted heteroaryl; or $R^3$ is —$Z^{13}$—$R^{13}$ wherein $Z^{13}$ is O, S or $NR^e$ and $R^{13}$ is $(C_1-C_6)$alkyl, substituted $(C_1-C_6)$alkyl, $(C_1-C_6)$alkanoyl or —$C(=O)NR^fR^g$ or $R^{13}$ and $R^9$ together with the atoms to which they are attached form a 5 to 7 membered ring.

In another embodiment a specific group of compounds of formula I are compounds wherein: when Y is —$CR^2$— and Z is absent; W is $NR^b$ or $(NR^cR^d)^+X^-$; or when Y is and Z is absent; W is N or $(NR^a)^+X^-$.

In another embodiment a specific group of compounds or formula I are compounds wherein:

the dashed line between Y and W represents a single or double bond;

when Y is —$CR^2$—, Z is —$(CR^{13}_2)_2$— or —$CR^{14}$=$CR^{14}$— and $R^{12}$ is a bond; W is N or $(NR^a)^+X^-$; or when Y is Z is —$(CR^{13}_2)_2$— or —$CR^{14}$=$CR^{14}$— and $R^{12}$ is a bond; W is $N^+X^-$;

$X^-$ is a pharmaceutically suitable counterion;

$Z^1, Z^2, Z^3$ and $Z^4$ are each independently O, S or $NR^e$; or $R^8$—$Z^1$—, $R^9$—$Z^2$—, $R^{10}$—$Z^3$—, and $R^{11}$—$Z^4$— can each independently be H;

$R^1$ is H, $(C_1-C_6)$alkyl, $(C_1-C_6)$alkoxy, $(C_1-C_6)$alkylthio, aryloxy or arylthio; and $R^2$ is H or $(C_1-C_6)$alkyl, wherein any $(C_1-C_6)$alkyl, $(C_1-C_6)$alkoxy, and $(C_1-C_6)$alkylthio of $R^1$ and $R^2$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^1$ and $R^2$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$; or $R^1$ and $R^2$ together with the carbon to which they are attached form a carbonyl group;

at least one of $R^3$, $R^4$, $R^5$, $R^6$ and $R^7$ is alkyl, substituted alkyl, optionally substituted alkenyl, optionally substituted alkynyl, optionally substituted cycloalkyl, optionally substituted arylalkyl, optionally substituted heteroarylalkyl, optionally substituted aryl, optionally substituted arylalkanoyl, $R^k$, or optionally substituted heteroaryl, wherein substituted alkyl is an alkyl group with 1 to 5 substituent groups independently selected from cycloalkyl, substituted cycloalkyl, alkoxycarbonyl, cyano, halo, hydroxyl, oxo, carboxy, aryloxy, heteroaryloxy, heterocyclooxy, nitro, sulfo, —$S(O)_2NR''R^p$, —$N(R'')S(O)_2R^p$, and —$NR''R^p$, wherein $R''$ and $R^p$ may be the same or different and are chosen from hydrogen, alkyl, arylalkyl, heteroarylalkyl, cycloalkyl, substituted cycloalkyl, aryl, heteroaryl and heterocyclic; and the remainder of $R^3$, $R^4$, $R^5$, $R^6$ and $R^7$ are independently H, halo, nitro, sulfo, —$S(O)_2NR''R^p$, —$N(R'')S(O)_2R^p$, —$NR^hR^i$ optionally substituted alkyl, optionally substituted arylalkyl, optionally substituted heteroarylalkyl, optionally substituted aryl, or optionally substituted heteroaryl; or $R^3$ is —$Z^{13}$—$R^{13}$ wherein $Z^{13}$ is O, S or $NR^e$ and $R^{13}$ is $(C_1-C_6)$alkyl, substituted $(C_1-C_6)$alkyl, $(C_1-C_6)$alkanoyl or —$C(=O)NR^fR^g$ or $R^{13}$ and $R^9$ together with the atoms to which they are attached form a 5 to 7 membered ring; or $R^6$ and $R^7$ together with the atoms to which they are attached form a 5 to 6 membered heterocycle wherein the heterocycle is optionally fused with an optionally substituted aryl.

when Z is absent $R^{12}$ is H, alkyl, halo, —$NR^hR^i$, $NO_2$, aryl, heteroaryl, aryl$(C_1-C_6)$alkyl, heteroaryl$(C_1-C_6)$alkyl, aryl $(C_1-C_6)$alkanoyl or heteroaryl$(C_1-C_6)$alkanoyl wherein alkyl, aryl, heteroaryl, aryl$(C_1-C_6)$alkyl, heteroaryl$(C_1-C_6)$alkyl, aryl$(C_1-C_6)$alkanoyl or heteroaryl$(C_1-C_6)$alkanoyl are optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;

$R^8$ and $R^9$ are each independently, $(C_1-C_6)$alkyl, $(C_1-C_6)$alkanoyl or —$C(=O)NR^fR^g$ or $R^8$ and $R^9$ together with the atoms to which they are attached form a 5 to 7 membered ring; or $R^8$—$Z^1$— and $R^9$—$Z^2$— can each independently be H;

$R^{10}$ and $R^{11}$ are each independently, $(C_1-C_6)$alkyl, $(C_1-C_6)$alkanoyl or —$C(=O)NR^fR^g$ or $R^{10}$ and $R^{11}$ together with the atoms to which they are attached form a 5 to 7 membered ring; or $R^{10}$—$Z^3$—, and $R^{11}$—$Z^4$— can each independently be H;

each $R^{13}$ is independently H, $(C_1-C_6)$alkyl, $(C_1-C_6)$alkoxy, $(C_1-C_6)$alkylthio, aryloxy or arylthio wherein any $(C_1-C_6)$ alkyl, $(C_1-C_6)$alkoxy, and $(C_1-C_6)$alkylthio of $R^{13}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^{13}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;

each $R^{14}$ is independently H, $(C_1-C_6)$alkyl, $(C_1-C_6)$alkoxy, $(C_1-C_6)$alkylthio, aryloxy or arylthio wherein any $(C_1-C_6)$ alkyl, $(C_1-C_6)$alkoxy, and $(C_1-C_6)$alkylthio of $R^{14}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^{14}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;

$R^a$ is $(C_1-C_6)$alkyl wherein $(C_1-C_6)$alkyl is optionally substituted with one or more groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;

$R^b$ is H or $(C_1-C_6)$alkyl wherein $(C_1-C_6)$alkyl is optionally substituted with one or more groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;

$R^c$ and $R^d$ are each independently selected from $(C_1-C_6)$ alkyl wherein $(C_1-C_6)$alkyl is optionally substituted with one or more groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;

each $R^e$ is independently H or $(C_1-C_6)$alkyl wherein $(C_1-C_6)$alkyl is optionally substituted with one or more halo;

$R^f$ and $R^g$ are each independently H, $(C_1-C_6)$alkyl, aryl, heteroaryl, aryl$(C_1-C_6)$ alkyl or heteroaryl$(C_1-C_6)$ alkyl; or $R^f$ and $R^g$ together with the nitrogen to which they are attached form a morpholino, piperazino, pyrrolidino or piperidino;

$R^h$ and $R^i$ are each independently H, $(C_1-C_6)$alkyl, aryl, heteroaryl, aryl$(C_1-C_6)$ alkyl or heteroaryl$(C_1-C_6)$ alkyl; or $R^h$ and $R^i$ together with the nitrogen to which they are attached form a morpholino, piperazino, pyrrolidino or piperidino;

each $R^k$ is independently selected from an aryl optionally substituted with one or more $R^m$, an alkyl substituted with one or more heterocycle, and an alkyl substituted with one or more substituted heterocycle;

each $R^m$ is independently, alkoxy, substituted alkoxy, heteroaryl, heterocycle, or —$S(O)_2NR''R^v$; and each $R^u$ and $R^v$ is independently H, $(C_1-C_6)$alkyl, aryl, heteroaryl, aryl$(C_1-C_6)$alkyl, or heteroaryl$(C_1-C_6)$alkyl; or $R^m$ and $R^n$ together with the nitrogen to which they are attached form a morpholino, piperazino, pyrrolidino or piperidino;

or a salt or prodrug thereof.

A specific group of compounds of formula I are the compounds of formula:
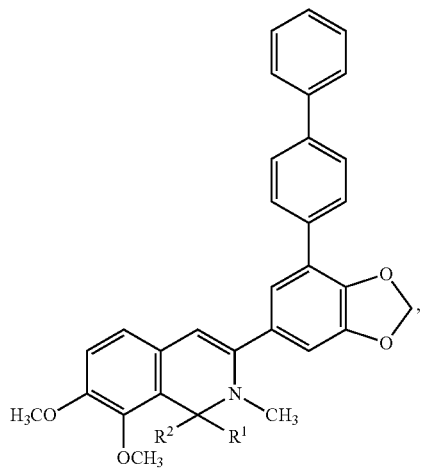
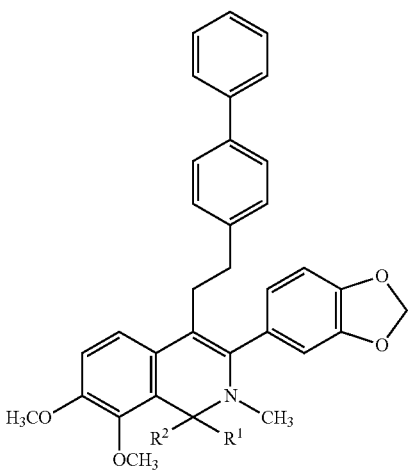
or a salt or prodrug thereof.
A specific group of compounds of formula I are the compounds of formula:
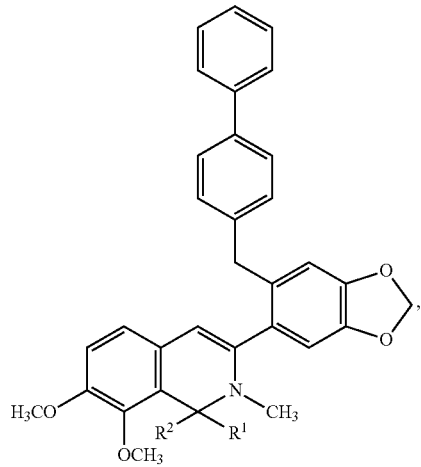
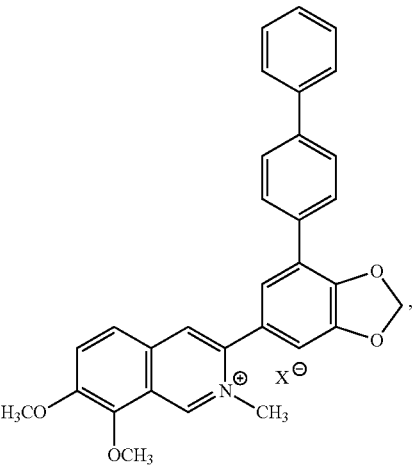
or
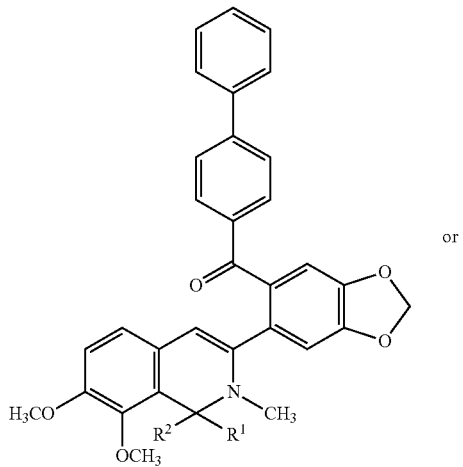
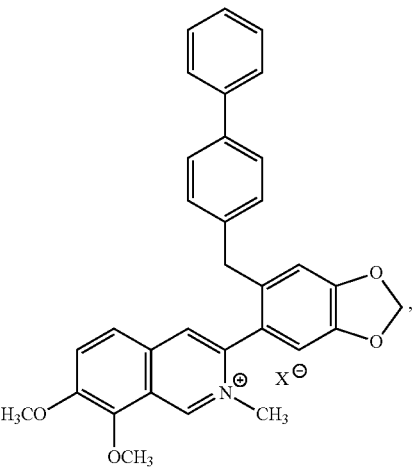

-continued
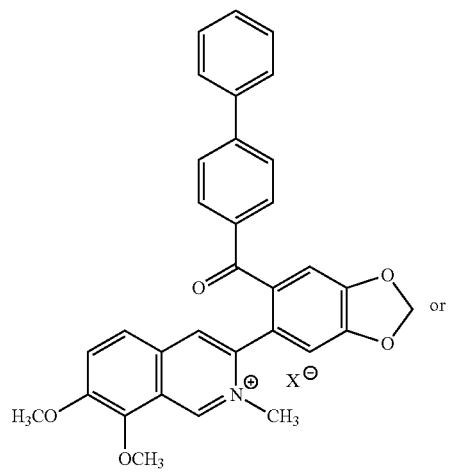
or
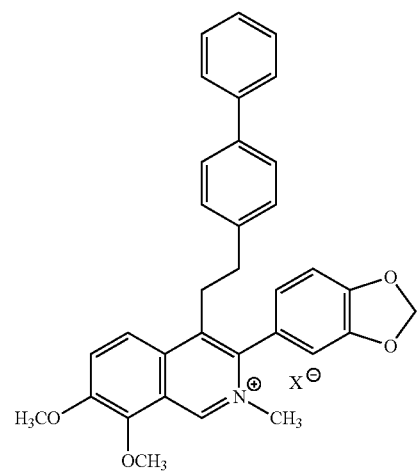
or a prodrug thereof.
A specific group of compounds of formula I are the compounds of formula:
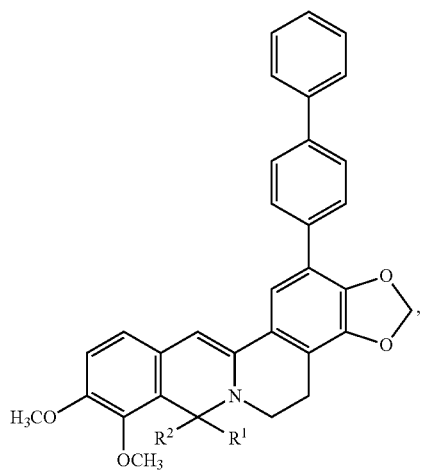
-continued
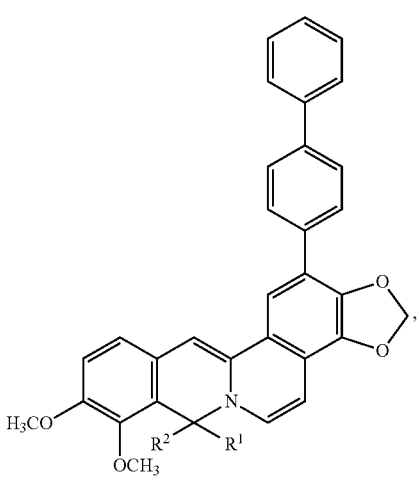
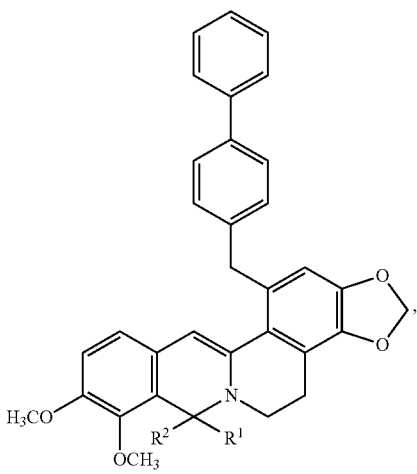
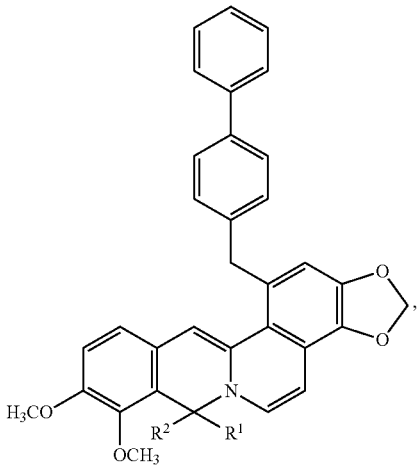

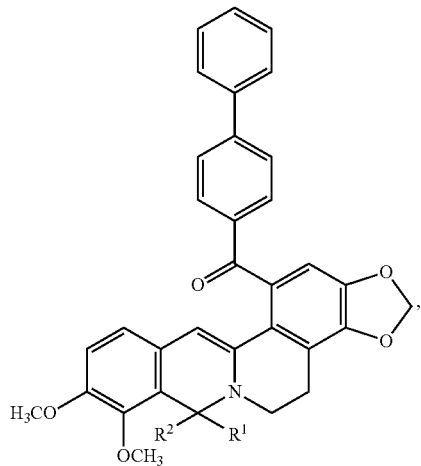
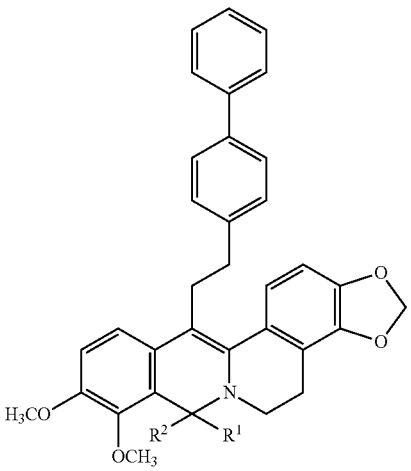
or a salt or prodrug thereof.
A specific group of compounds of formula I are the compounds of formula:
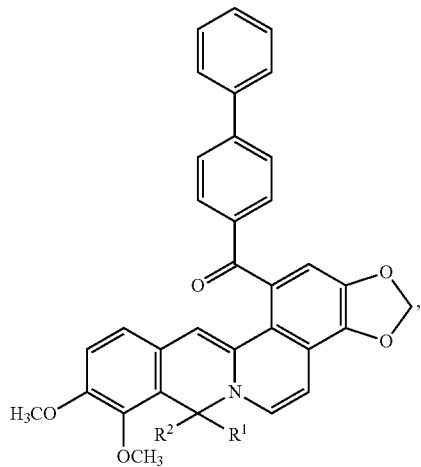
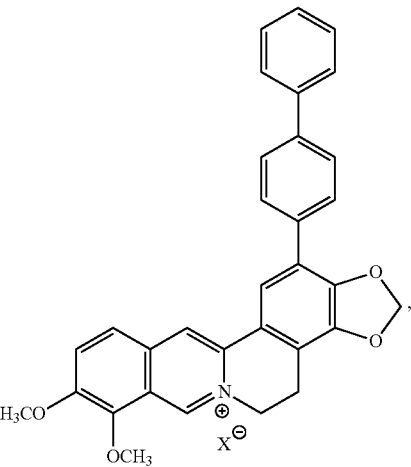
or
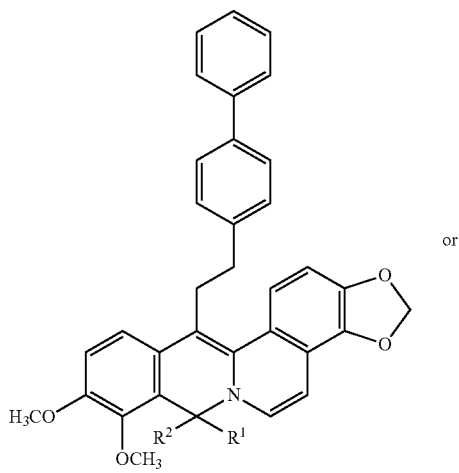
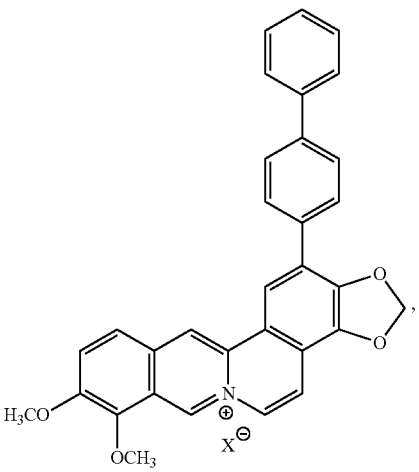

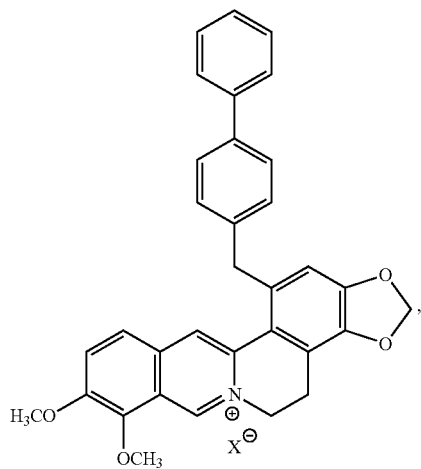
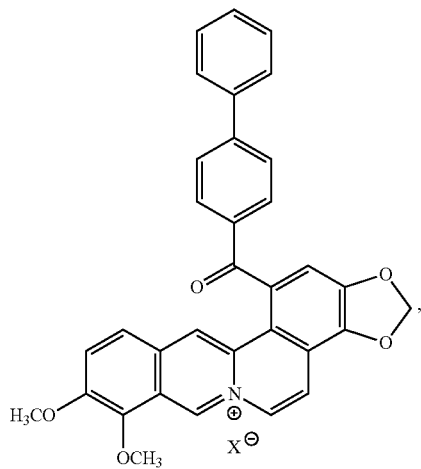
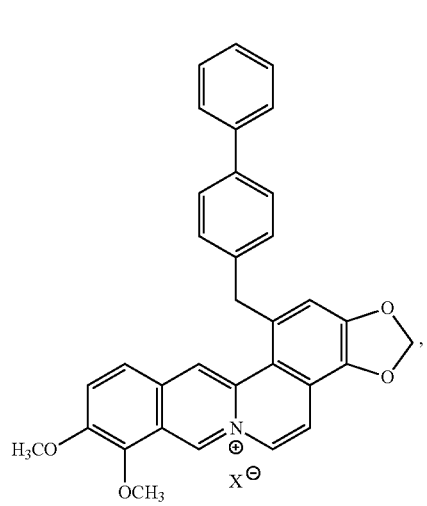
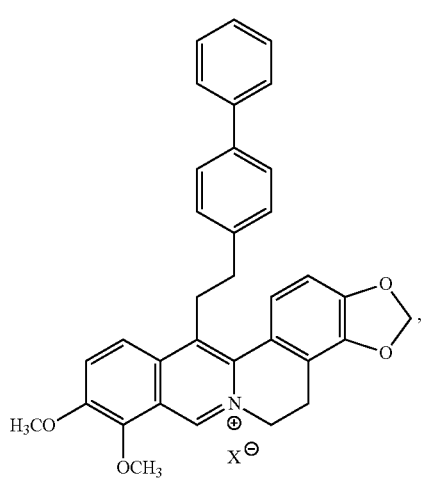
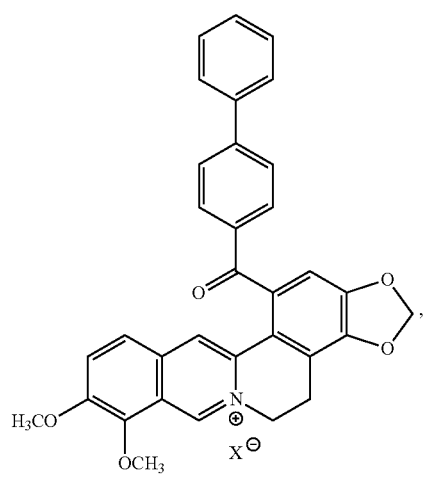
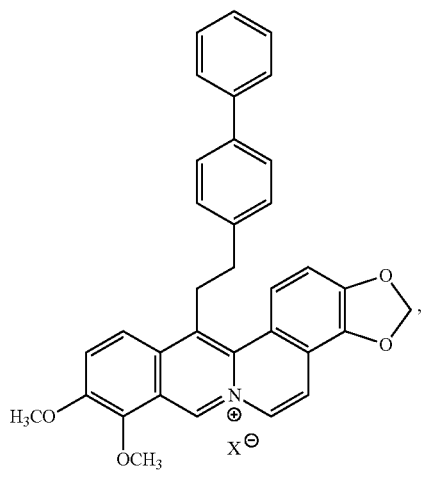

27
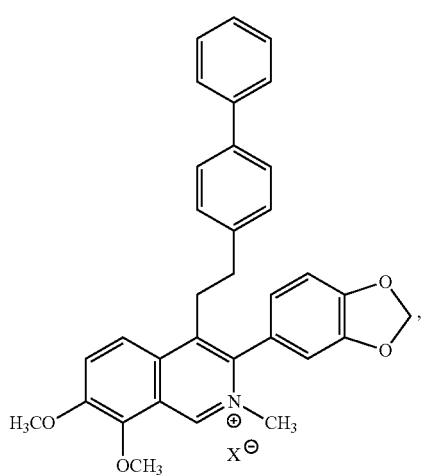
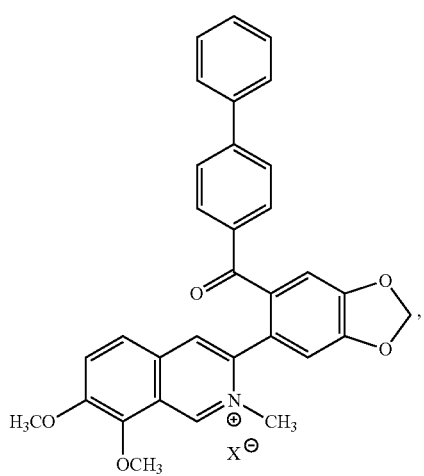
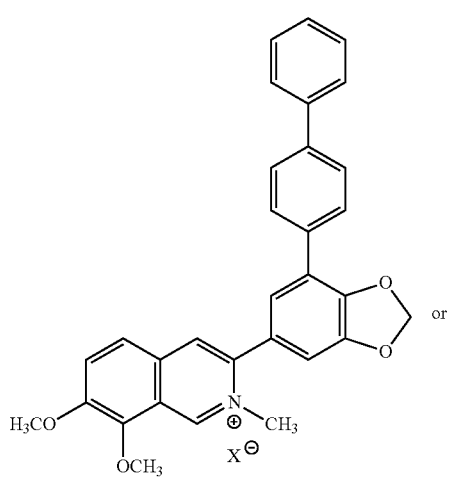
28
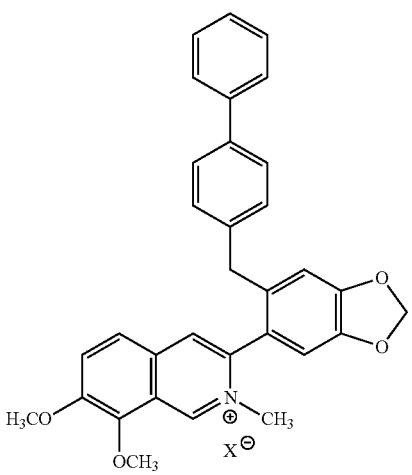
or a prodrug thereof.
A specific compound of the invention is selected from:
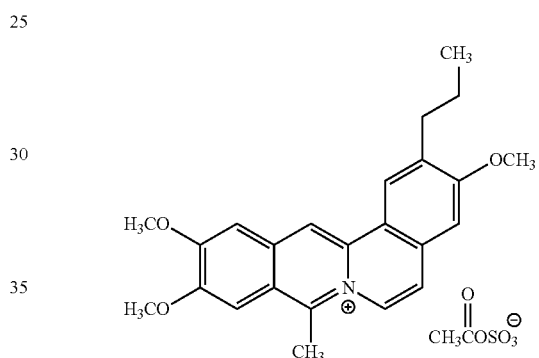
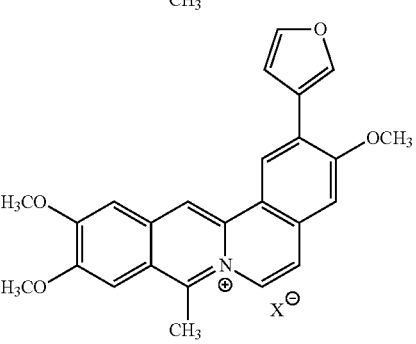
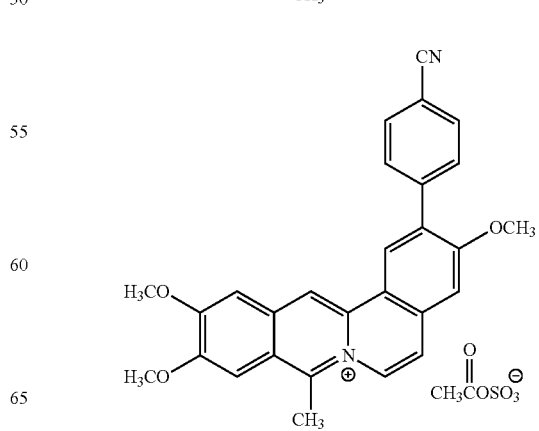

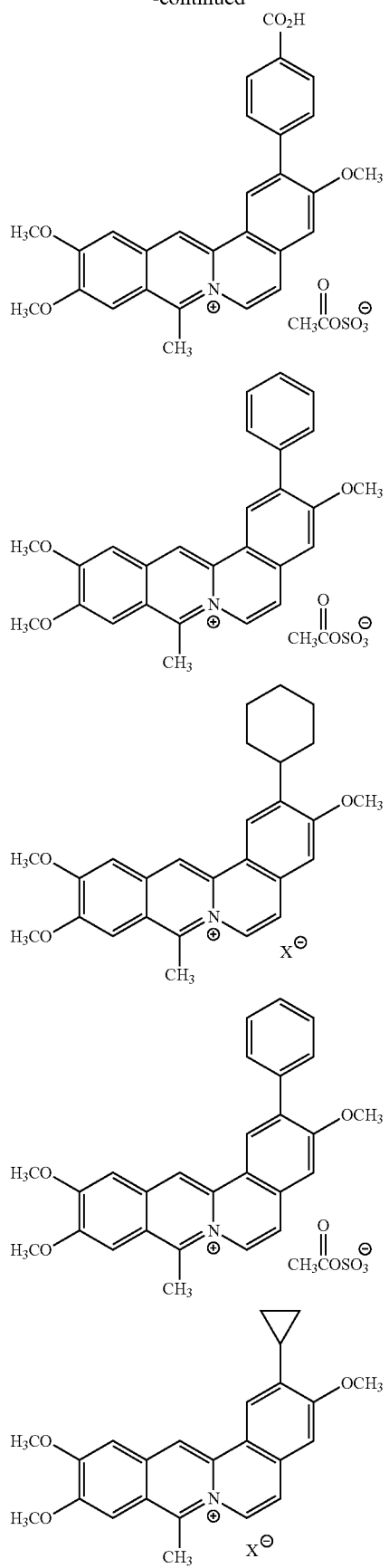
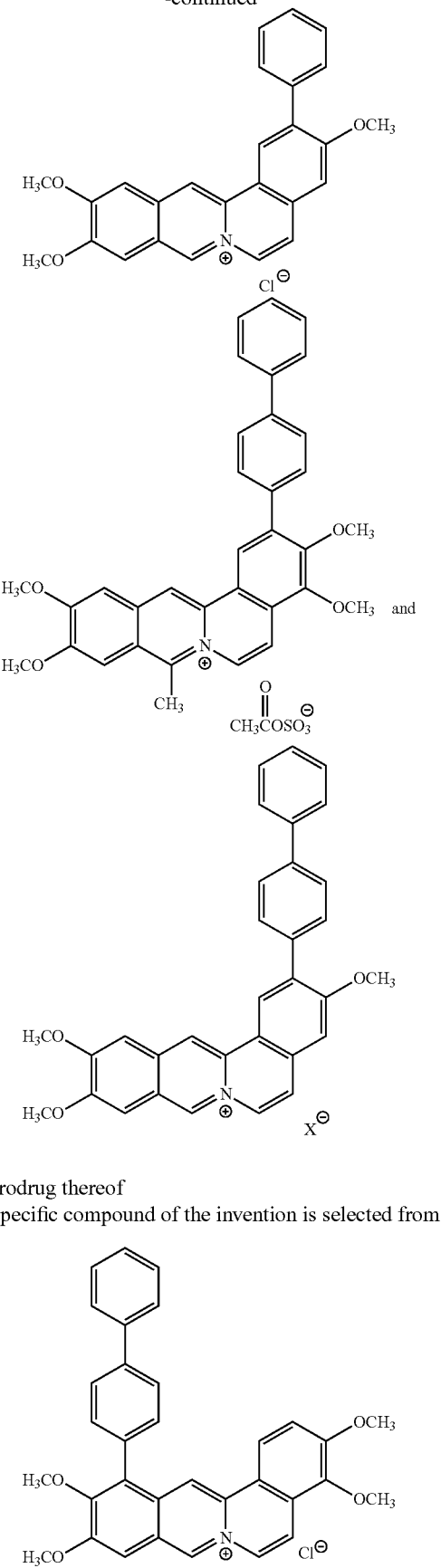
or a prodrug thereof
A specific compound of the invention is selected from:

-continued
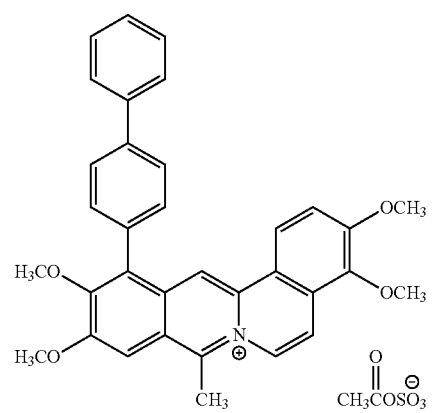
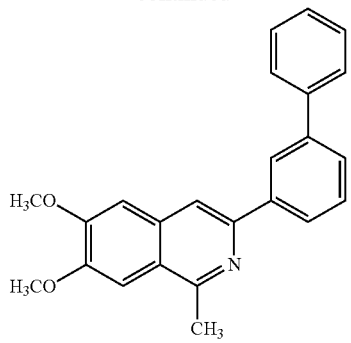
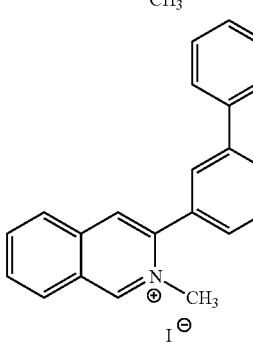
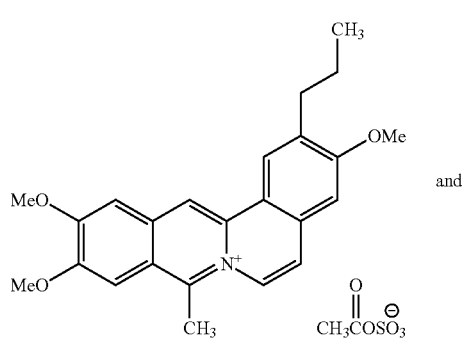
and
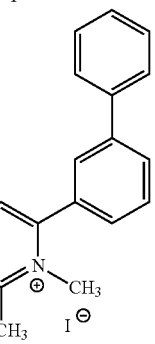
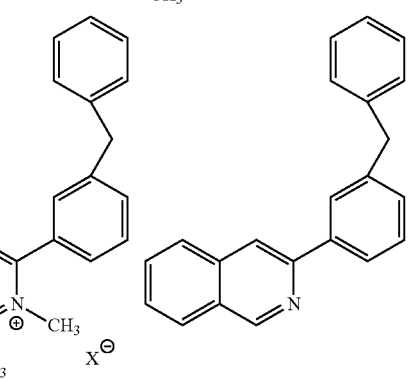
or a prodrug thereof
A specific compound of the invention is selected from:
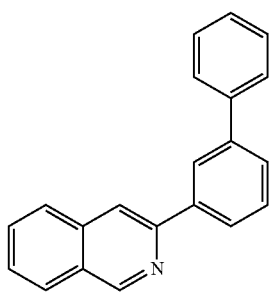
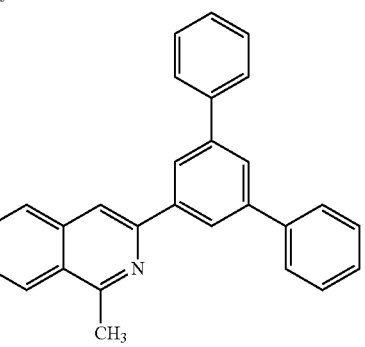

-continued
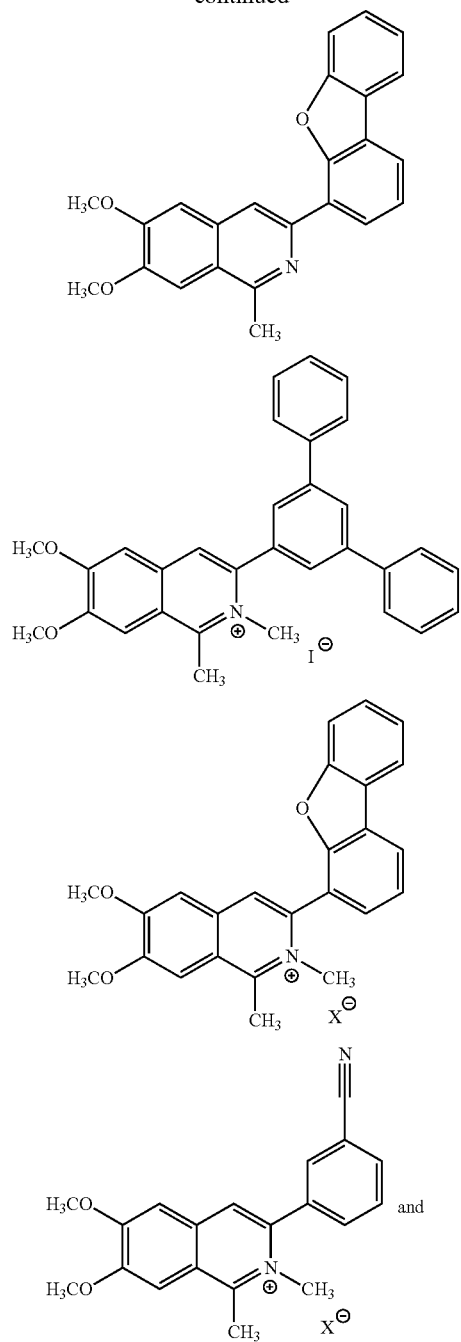
or a salt or prodrug thereof.
A specific compound of the invention is selected from:
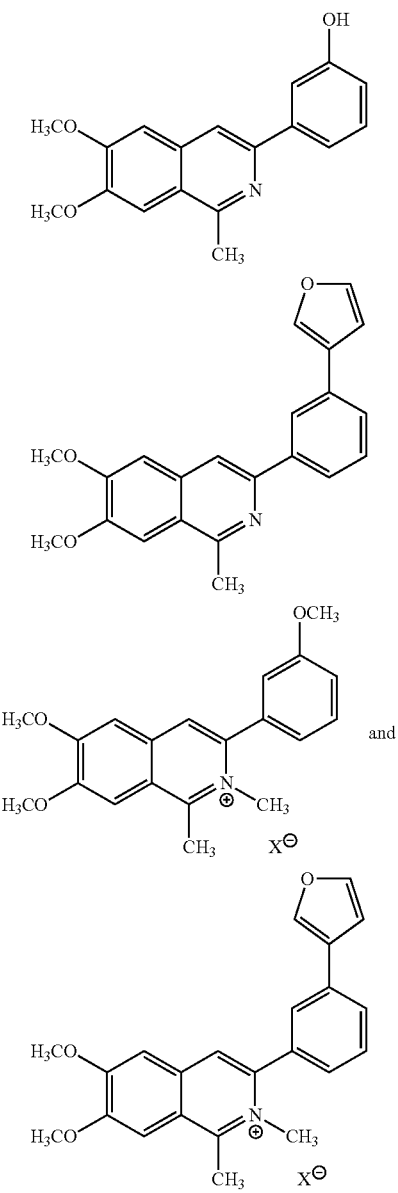
or a salt or prodrug thereof.
A specific compound of the invention is selected from:
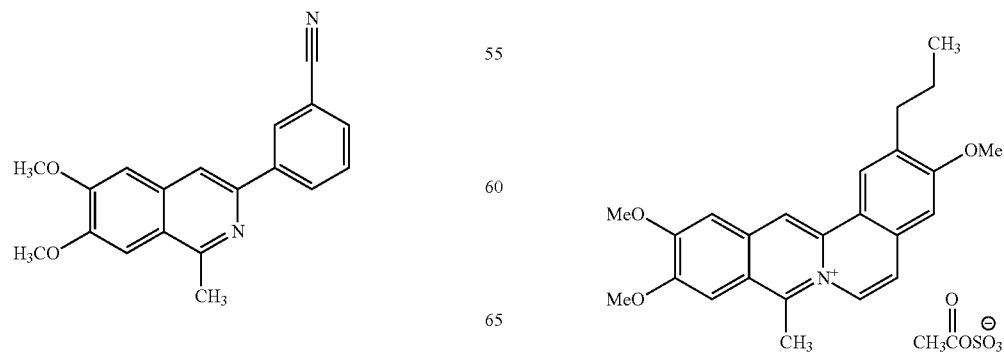

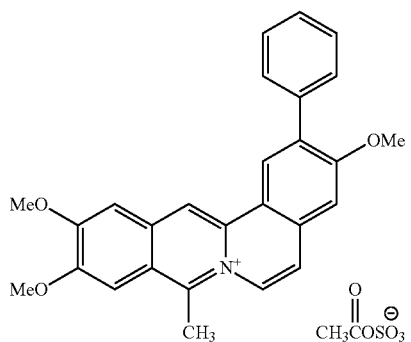
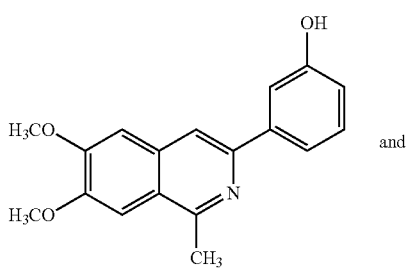
and
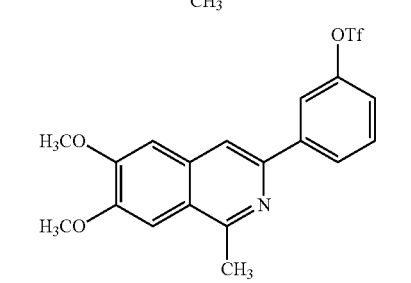
or a prodrug thereof
A specific compound of the invention is selected from:
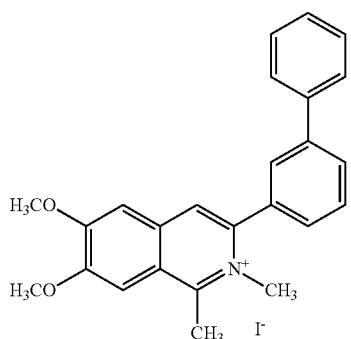
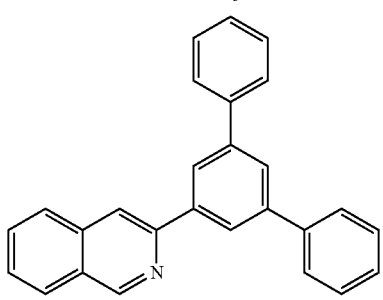
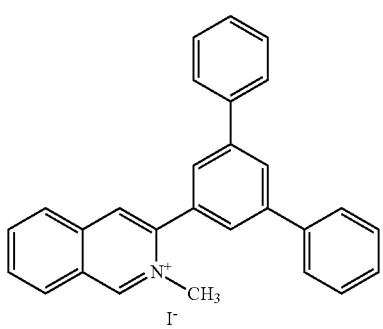
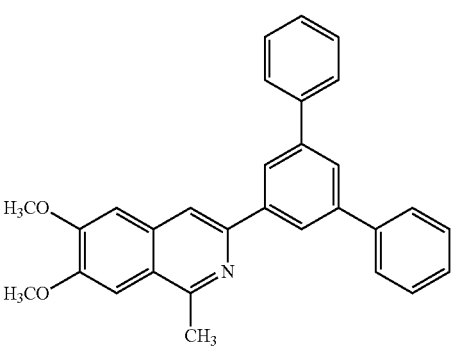
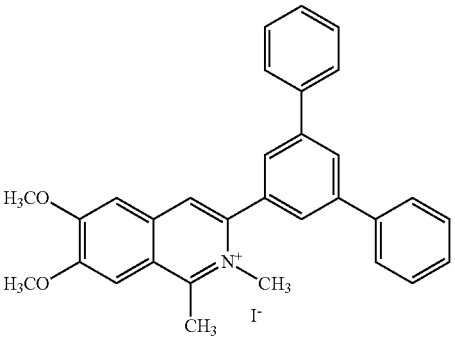

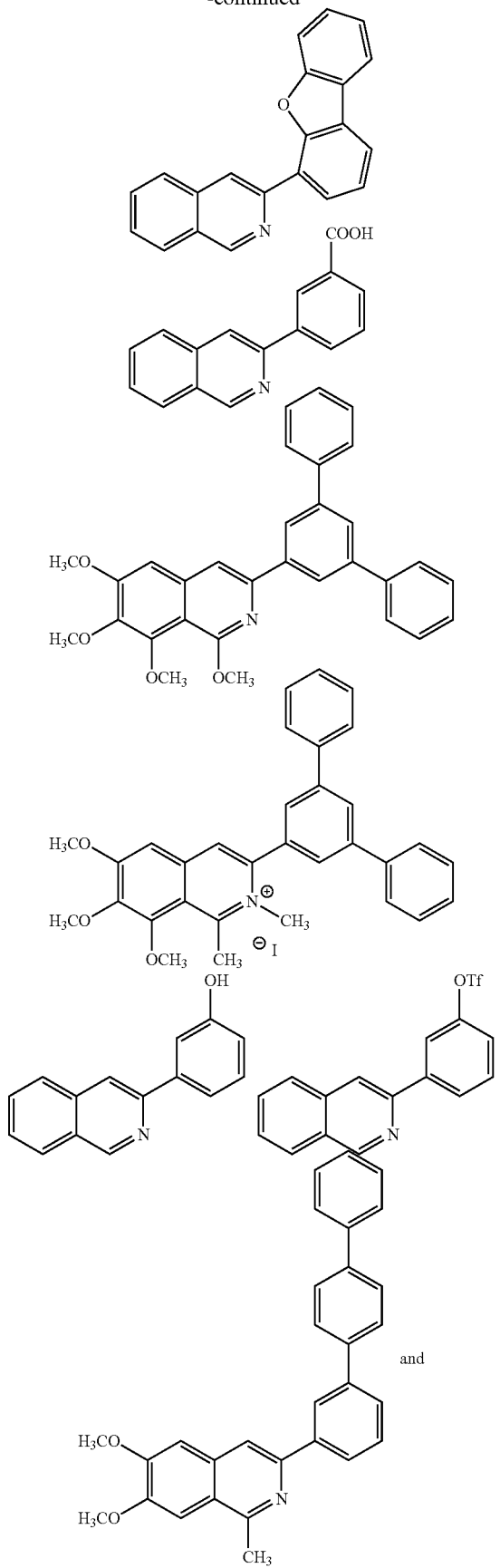
and
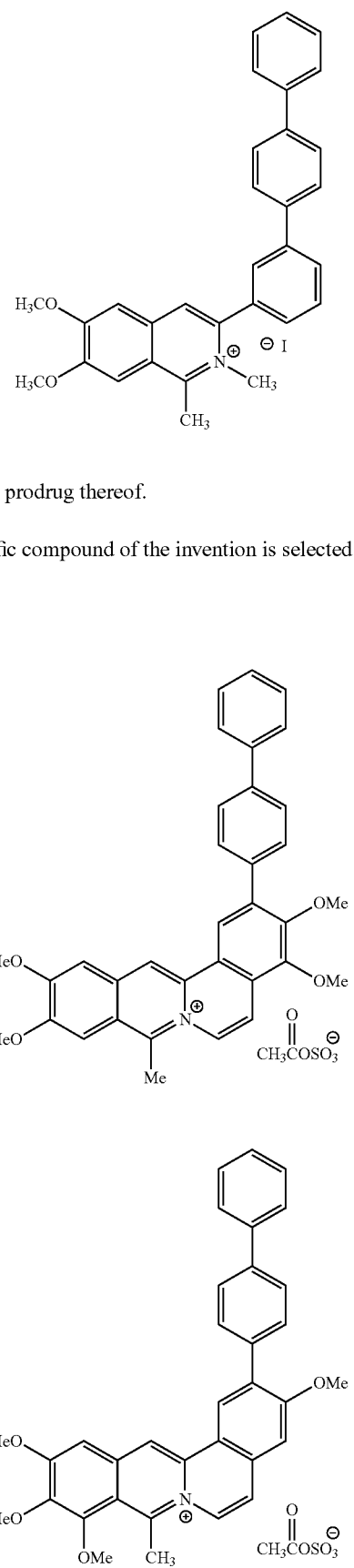
or a salt or prodrug thereof.
A specific compound of the invention is selected from:

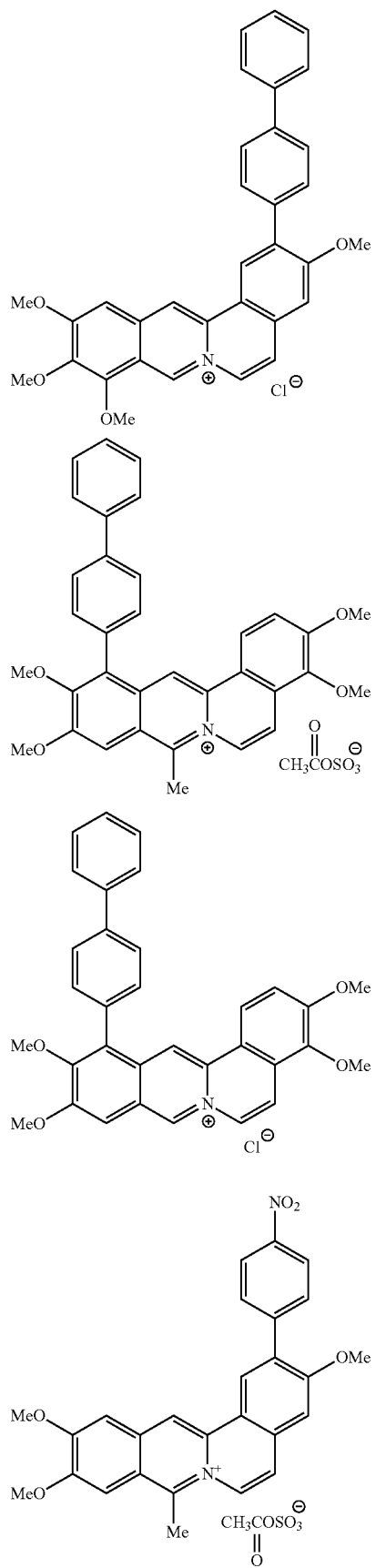
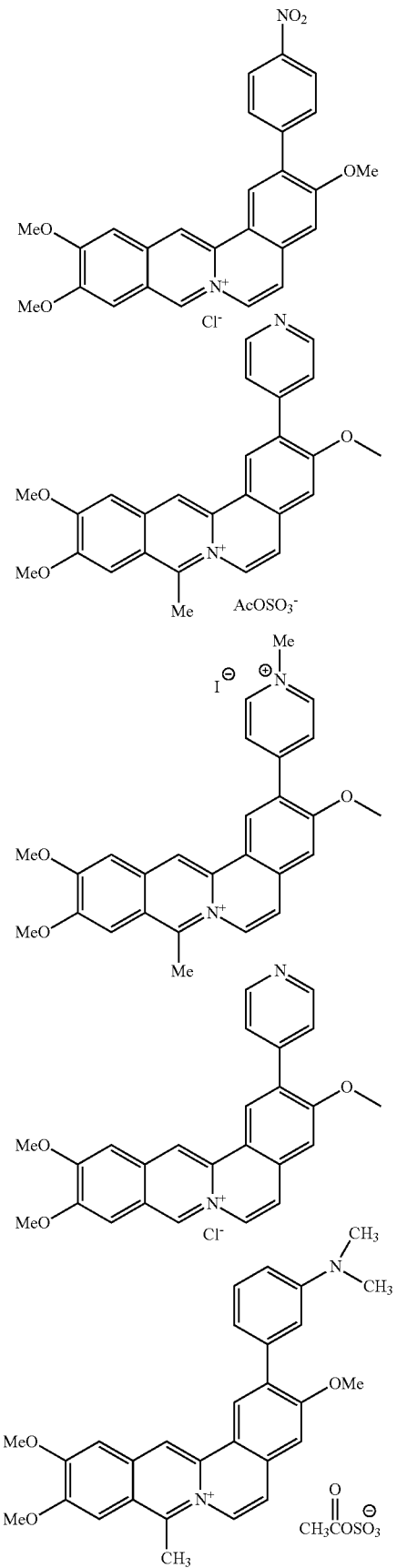

-continued

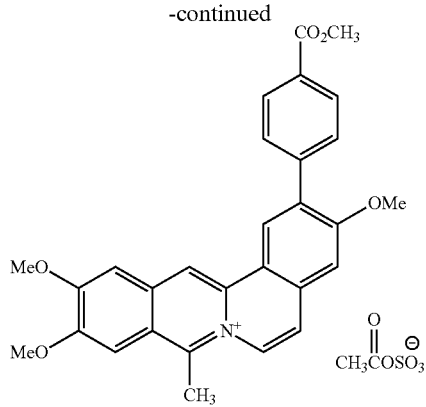
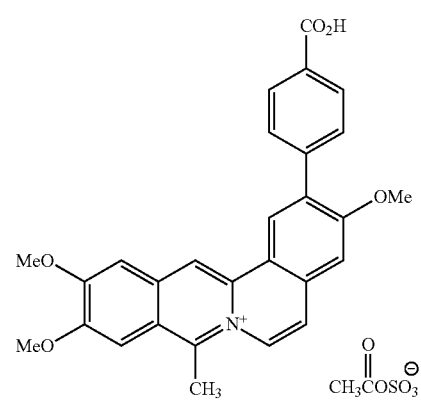
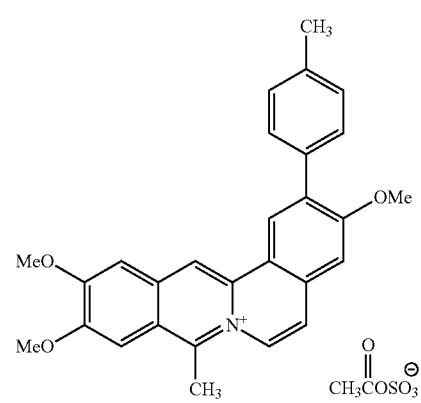
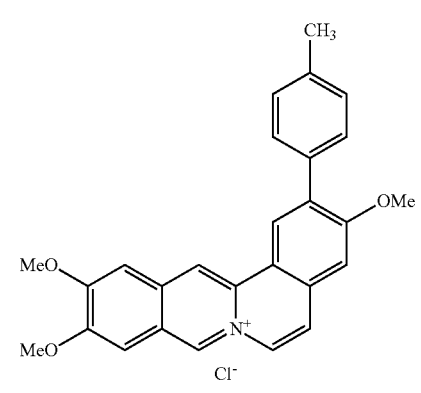

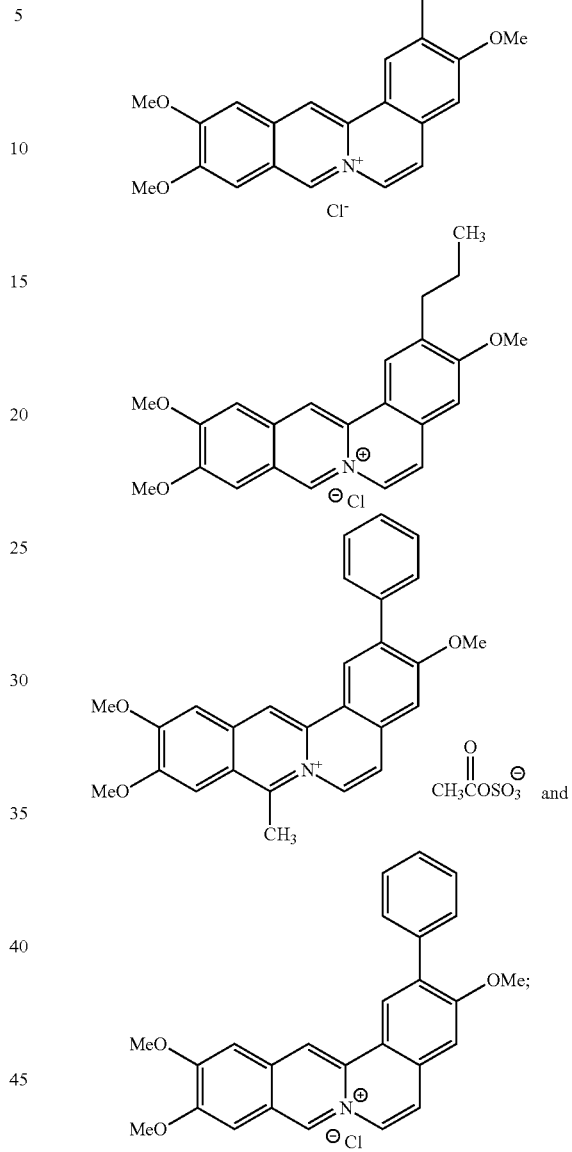

or a prodrug thereof.

A specific group of compounds of formula I are compounds wherein $R^3$ is $(C_1-C_6)$alkyl-O—.

The compounds of the invention are useful to treat bacterial infections including infections by Gram-negative bacterial strains, Gram-positive bacterial strains or multiple drug-resistant bacterial strains Gram-negative bacterial strains include *Escherchia coli, Caulobacter crescentus, Pseudomonas aeruginosa, Agrobacterium tumefaciens, Branhamella catarrhalis, Citrobacter diversus, Enterobacter aerogenes, Enterobacter cloacae, Enterobacter sakazakii, Enterobacter asburiae, Pantoea agglomerans, Klebsiella pneumoniae, Klebsiella oxytoca, Klebsiella rhinoscleromatis, Proteus mirabilis, Salmonella typhimurium, Salmonella enteriditis, Serratia marcescens, Shigella sonnei, Neisseria gonorrhoeae, Acinetobacter baumannii, Acinetobacter calcoaceticus, Acinetobacter lwoffi, Fusobacterium nucleatum, Veillonella parvula, Bacteroides* forsythus, Actinobacillus actinomycetemcomitans, Aggregatibacter actinomycetemcomitans, Porphyromonas gingivalis, Helicobacter pylori, Francisella tularensis, Yersinia pestis, Borrelia burgdorferi, Neisseria meningitidis and Haemophilus influenza.

Gram-positive bacterial strains include Staphylococcus aureus, Staphylococcus epidermidis, Staphylococcus saprophyticus, Streptococcus pyogenes, Streptococcus faecalis, Enterococcus faecalis, Enterococcus faecium, Bacillus subtilis, Bacillus anthracis, Bacillus cereus, Micrococcus luteus, Mycobacterium tuberculosis, Clostridium difficile, Propionibacterium acnes, Streptococcus mutans, Actinomyces viscosus, Actinomyces naeslundii, Streptococcus sanguis, Streptococcus pneumoniae, Streptococcus viridans and Streptococcus salivarius.

Multiple drug-resistant bacterial strains include methicillin-resistant Staphylococcus aureus, vancomycin-resistant Enterococci, multiple drug-resistant Mycobacterium tuberculosis, multidrug-resistant Clostridium difficile.

In one embodiment compounds of the present invention may be administered as a composition used to treat and/or prevent a bacterial infection wherein the bacterial cell uses polymerized FtsZ protein, or a homolog thereof, to facilitate cytokinesis. To this end, compounds of the present invention may be administered to treat Staph Infections, Tuberculosis, Urinary Tract Infections, Meningitis, Enteric Infections, Wound Infections, Acne, Encephalitis, Skin Ulcers, Bed Sores, Gastric and Duodenal Ulcers, Eczema, Periodontal disease, Gingivitis, Halitosis, Anthrax, Tularemia, Endocarditis, Prostatitis, Osteomyelitis, Lyme Disease, Pneumonia, or the like.

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, other antimicrobial (for example, an aminoglycoside, an antifungal, an antiparasitic, an antiviral, a carbapenem, a cephalosporin, a flurorquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an antitussive, an anti-emetic, an anti-ulcer, a laxative, an anticoagulant, an erythropieitin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

The term "prodrug" as used herein refers to any compound that when administered to a biological system (e.g. a mammal such as a human) generates the drug substance, i.e. active ingredient, as a result of spontaneous chemical reaction(s), enzyme catalyzed chemical reaction(s), photolysis, and/or metabolic chemical reaction(s) or by some other process. A prodrug is thus a modified (e.g. covalently modified) analog or latent form of a therapeutically-active compound. A prodrug may also be an active metabolite or therapeutically-active compound itself.

By way of example a prodrug may generate the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191; Tranoyl-Opalinski, I., Fernandes, A., Thomas, M., Gesson, J.-P., and Papot, S., Anti-Cancer Agents in Med. Chem., 8 (2008) 618-637). Enzymes which are capable of an enzymatic activation mechanism with the prodrug compounds of the invention include, but are not limited to nitroreductase, proteases (e.g. serine proteases such as prostate specific antigen (PSA), amidases, esterases, microbial enzymes, phospholipases, cholinesterases, and phosphases. Processes for preparing compounds of formula I are provided as further embodiments of the invention and are illustrated by the following procedures in which the meanings of the generic radicals are as given above unless otherwise qualified.

Representative compounds of the invention and synthetic intermediates that can be used to prepare compounds of the invention can be prepared as illustrated below in Schemes 1-17.

Scheme 1

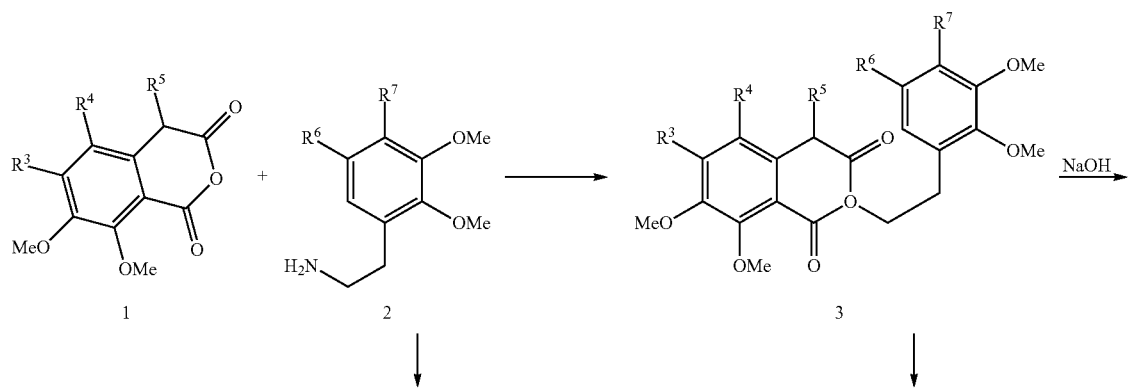

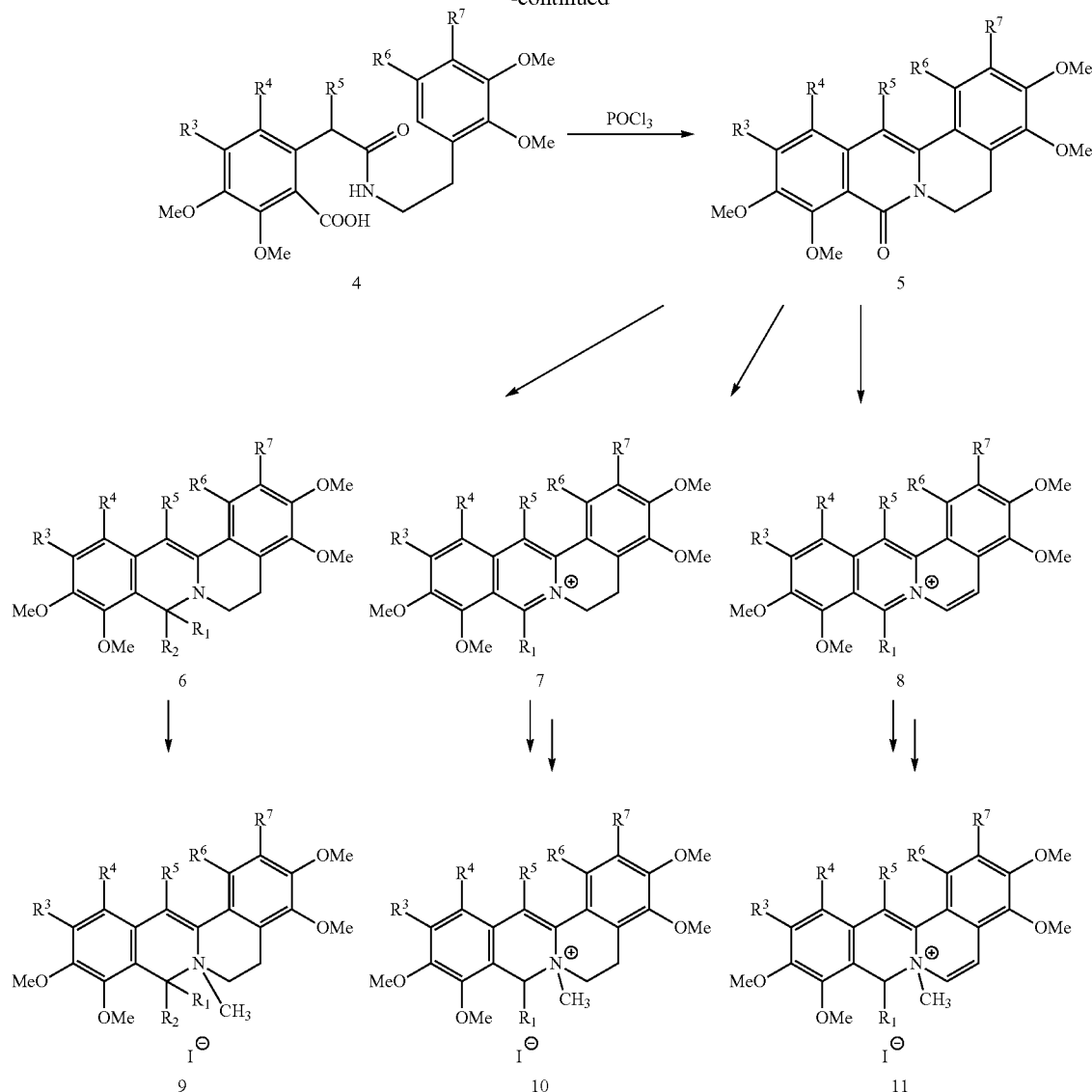

Condensation of readily available anhydride 1 and amine 2 can furnish imide 3. The resulting imide 3 can then be hydrolyzed to the corresponding acid amide 4. Acid catalyzed cyclization of 4 can then lead to oxypseudoberbernine 5. The key intermediate compound 5 can then be converted to compound 6, 7, and 8 using conventional chemistry. Each of these compounds can then be quarternized to afford the desired compounds 9, 10, and 11 respectively.

Scheme 2

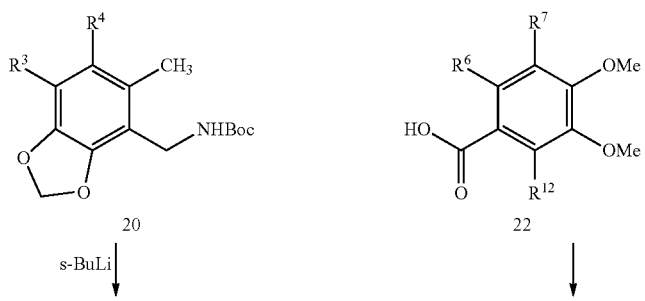

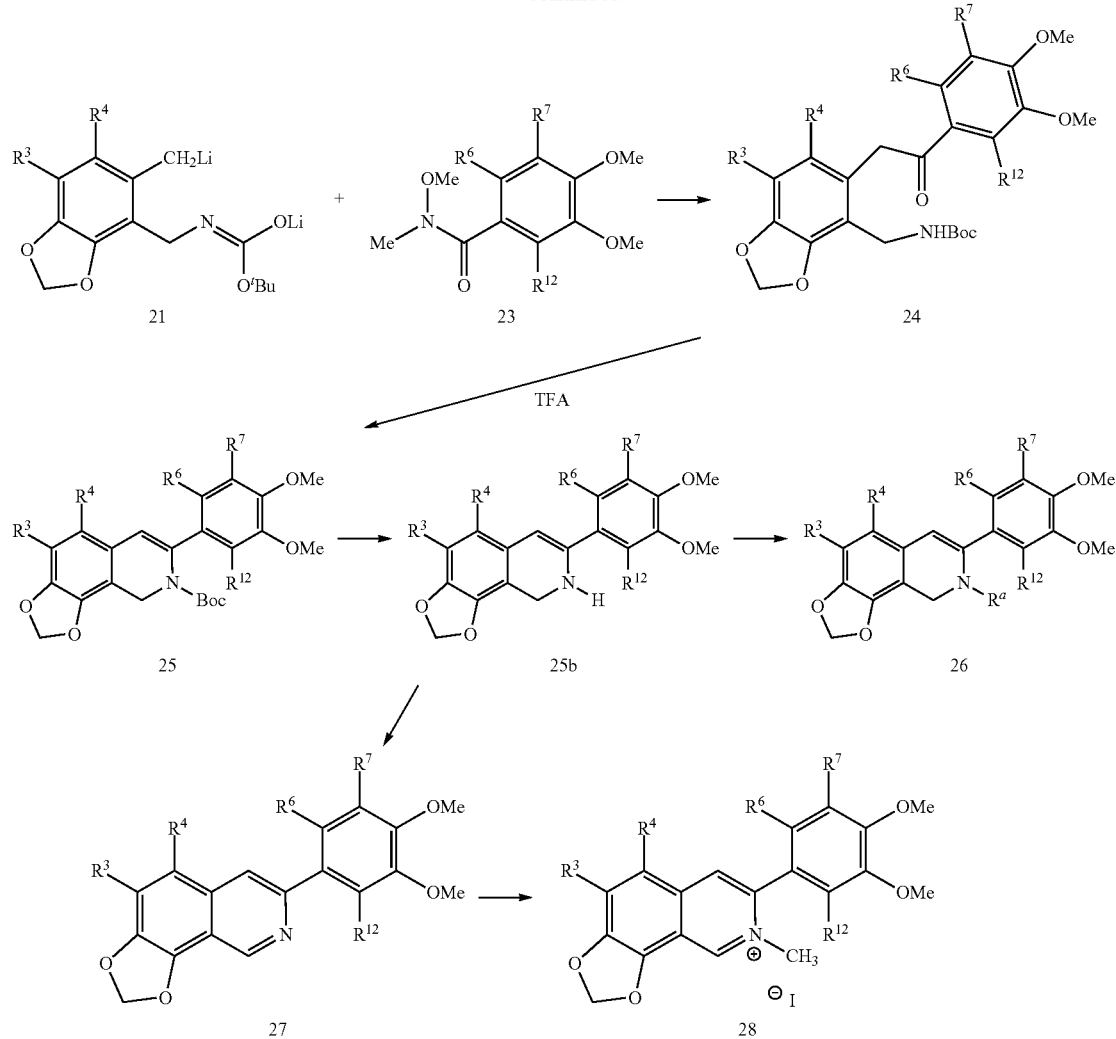

The substituted N-Boc protected benzylamine 20 can be converted to the dilithio 21 by treatment with two equivalents of sec-butyllithium. Acylation of dianion 21 can be accomplished by treatment with N-methoxy-N-methylamides derivative 23 (made from the corresponding acid 22) to afford the key intermediate compound 24. Exposure of ketone 24 to a catalytic amount of TFA can provide the Boc-1,2-dihydroisoquinoline 25. The Boc group in 25 can be removed to provide 25a and the resulting free amine can be functionalized to 26 by various electrophilic reagents. Alternatively 26 can be converted to compound 28.

Scheme 3

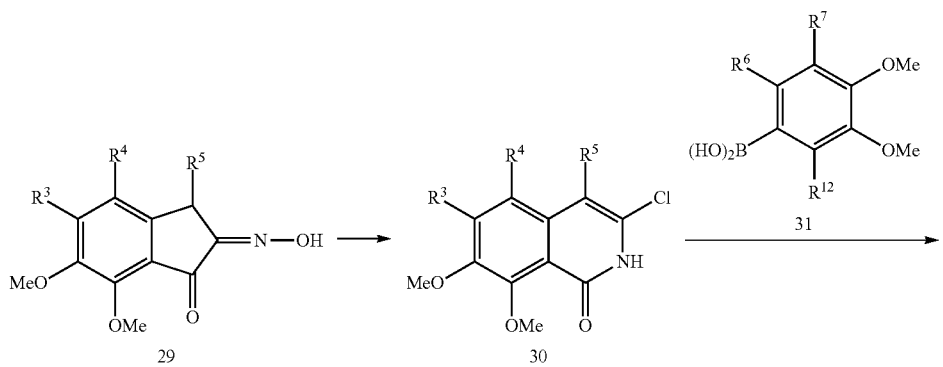

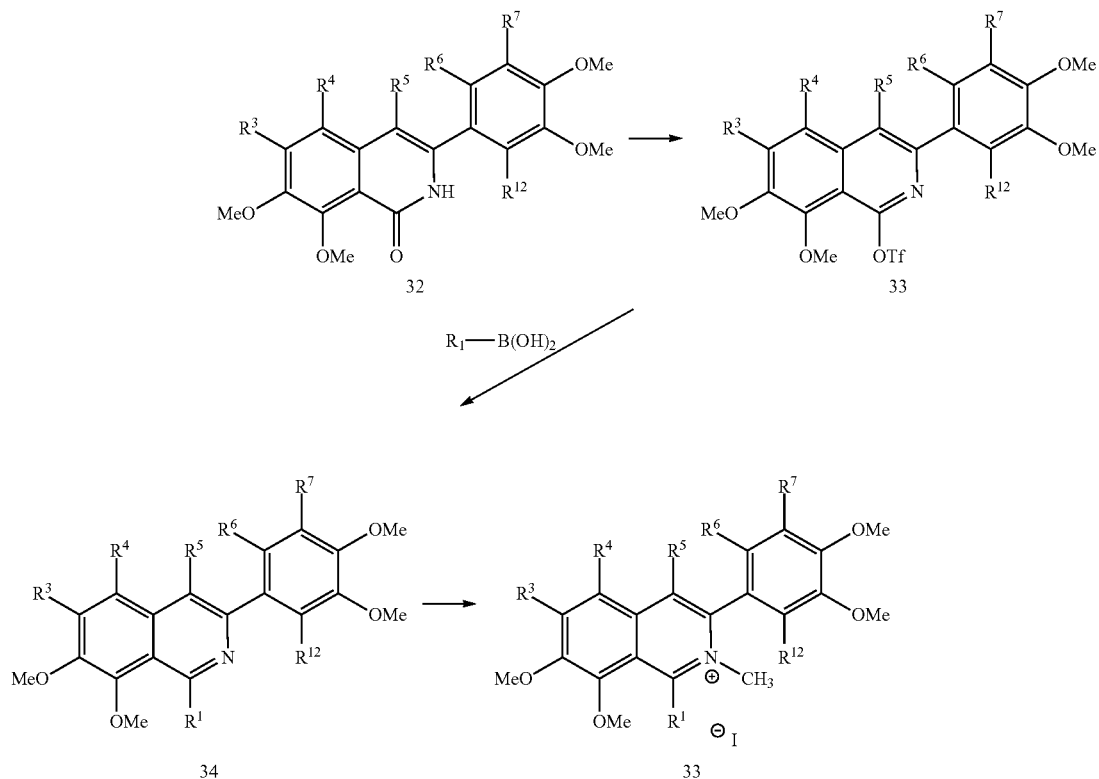

Beckmann rearrangement of α-ketooxime 29 with phosphorus pentachloride can produce 3-chloro-1(2H)isoquinolone 30 using literature methods. Suzuki coupling of 30 with boronic acid 31 can afford the key compound 32. Compound 32 can then be converted to triflate 33 which in turn can undergo a second Suzuki reaction with a boronic acid to afford compound 34. Quarternization of 34 can then lead to compound 35.

Scheme 4 illustrates methods and intermediates that are useful for preparing $R^7$ substituted compounds of the invention.

Scheme 4

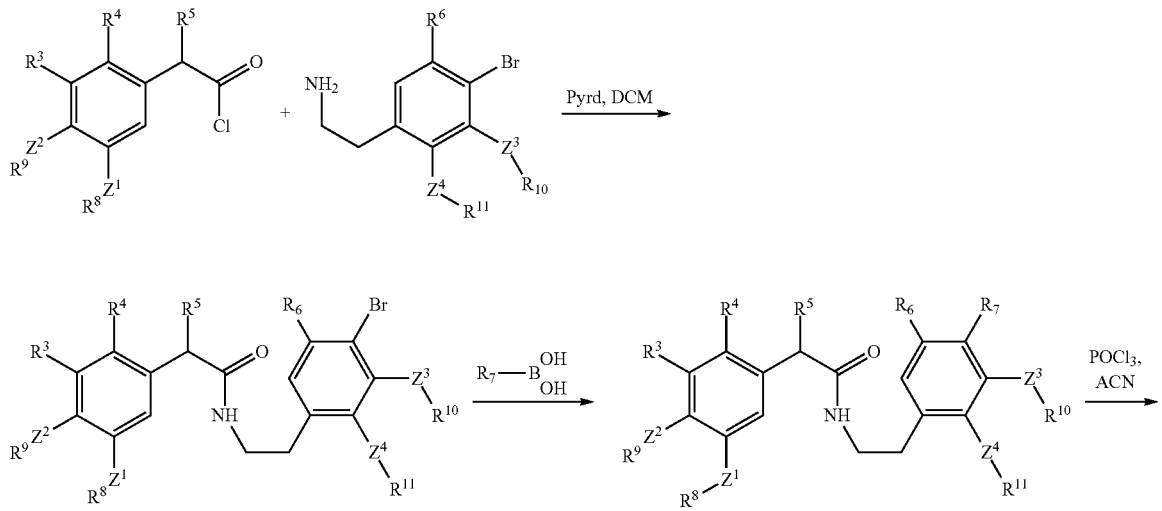

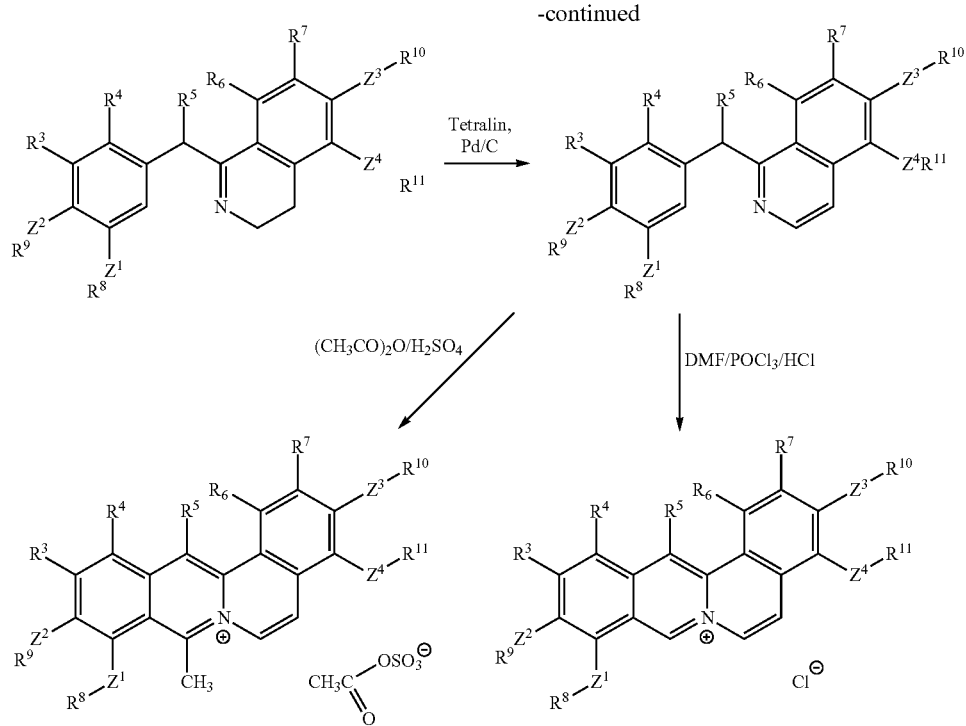
Scheme 5 illustrates the synthesis carried out in Example 1 hereinbelow.

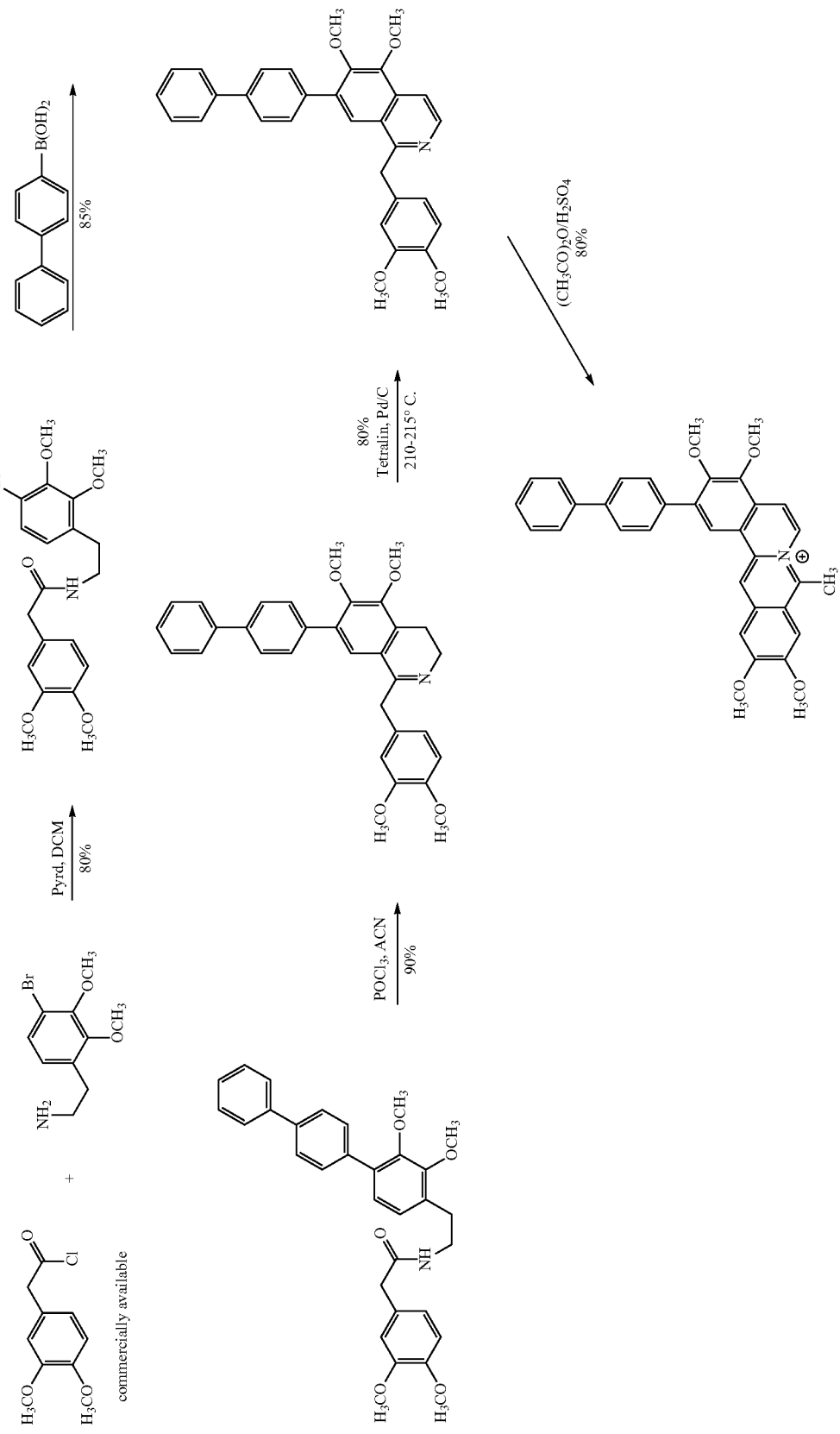

Scheme 6 illustrates methods and intermediates that are useful for preparing $R^5$ substituted compounds of the invention.
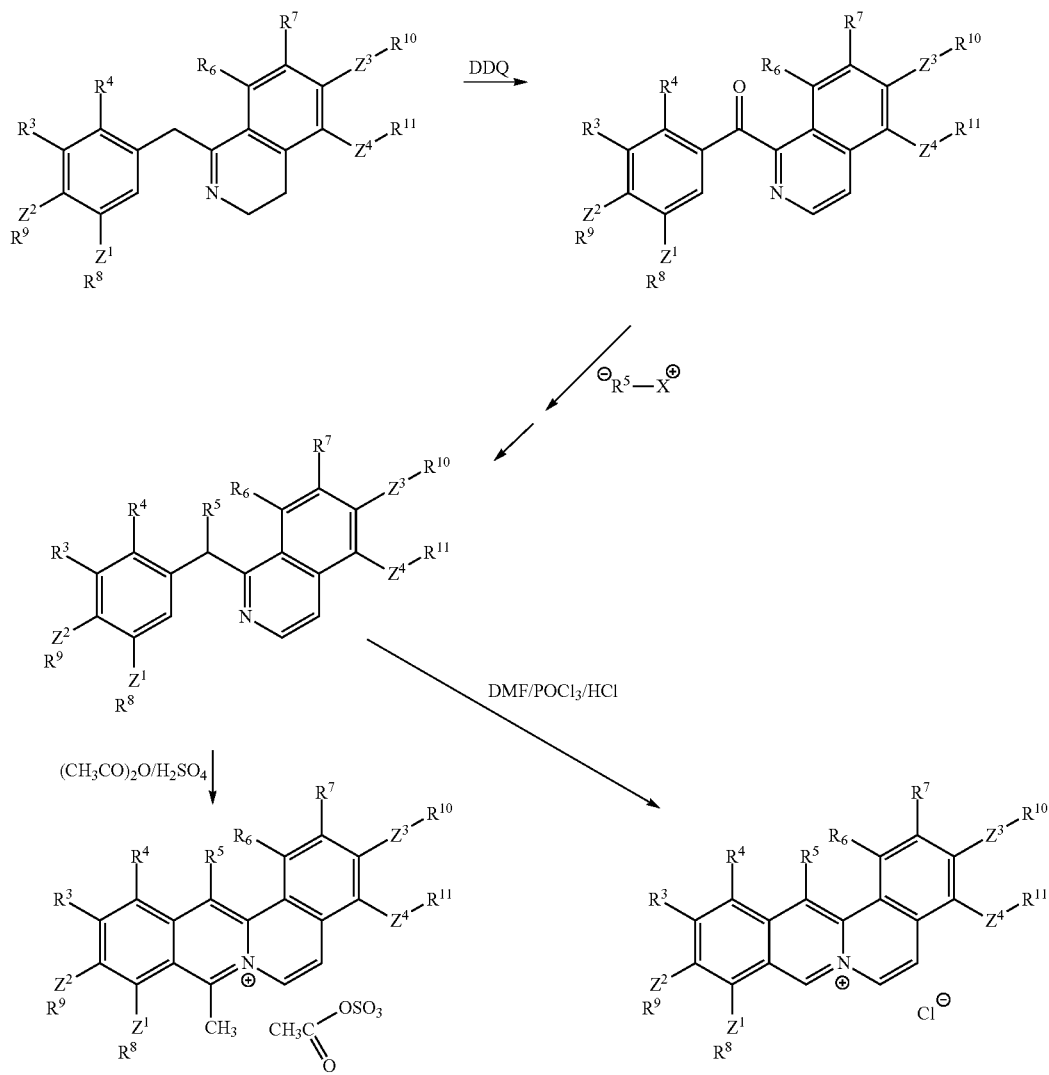
Scheme 7 illustrates methods and intermediates that are useful for preparing compounds that are substituted at $R^5$ and $R^7$.
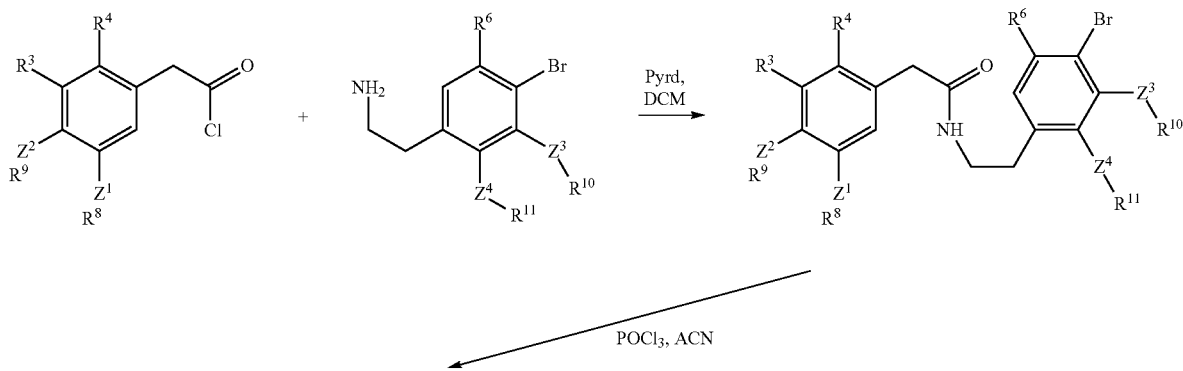

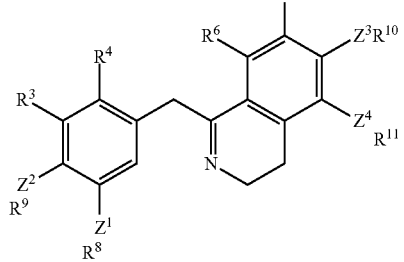
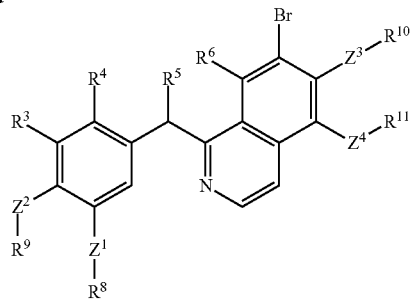
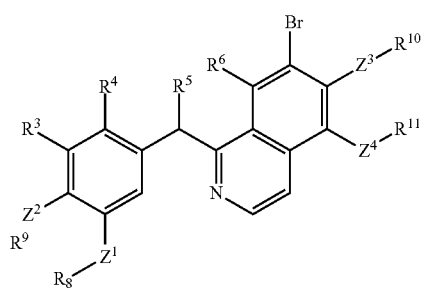
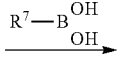
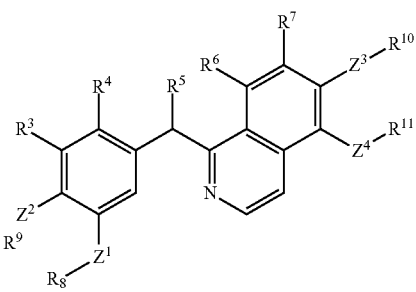
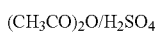
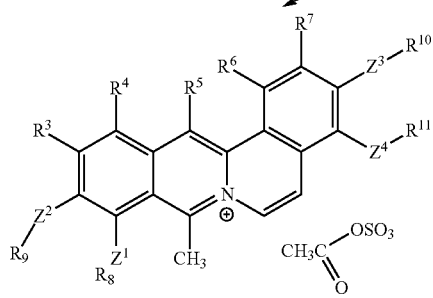
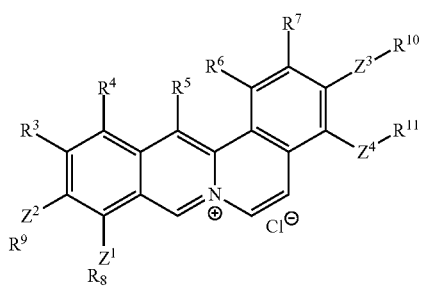

Scheme 8 illustrates the preparation of an intermediate phenethylamine that is useful for preparing compounds of the invention.

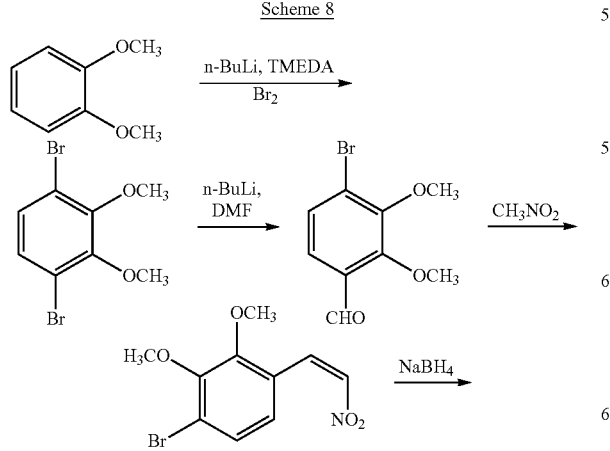

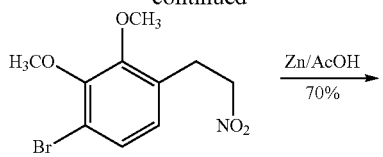
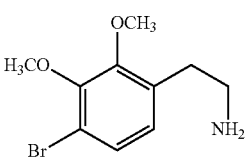

Scheme 8a illustrates methods for the preparation of phenethylamine intermediates that have $R^{14}$ substituents. The formation of β-substituted derivatives uses a nucleophile in a Michael addition reaction and the α-substituted derivatives is formed from a carbanion generated at the position adjacent to the nitro substituent, followed by reaction with an appropriate electrophile.

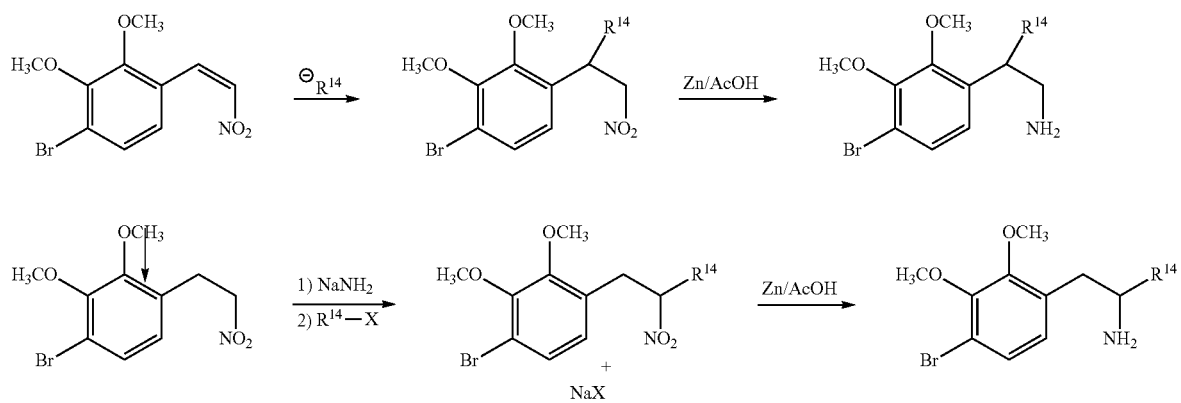
Scheme 9 illustrates methods and intermediates that are useful for preparing compounds of the invention.
Scheme 9
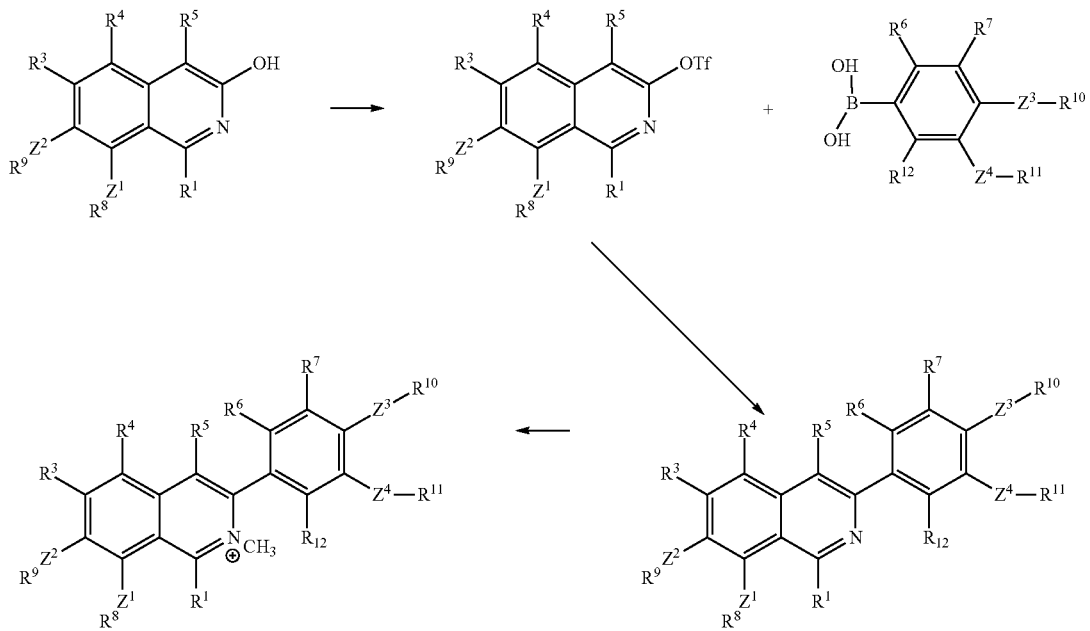
Scheme 10 illustrates methods and intermediates that are useful for preparing $R^7$ substituted compounds of the invention.
Scheme 10
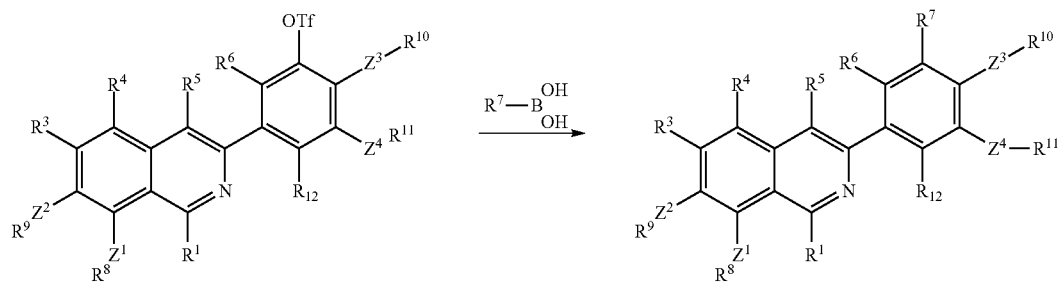

Scheme 11 illustrates the preparation of isoquinoline intermediates that are useful for preparing compounds of the invention.
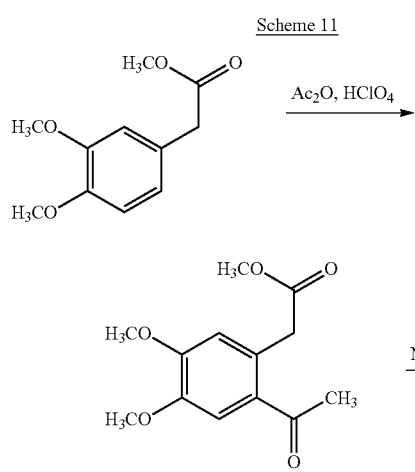
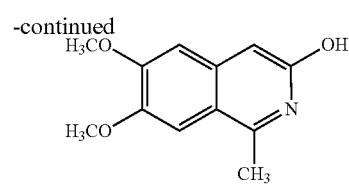
Scheme 12 illustrates the preparation of a triflate intermediate that is useful for preparing compounds of the invention.
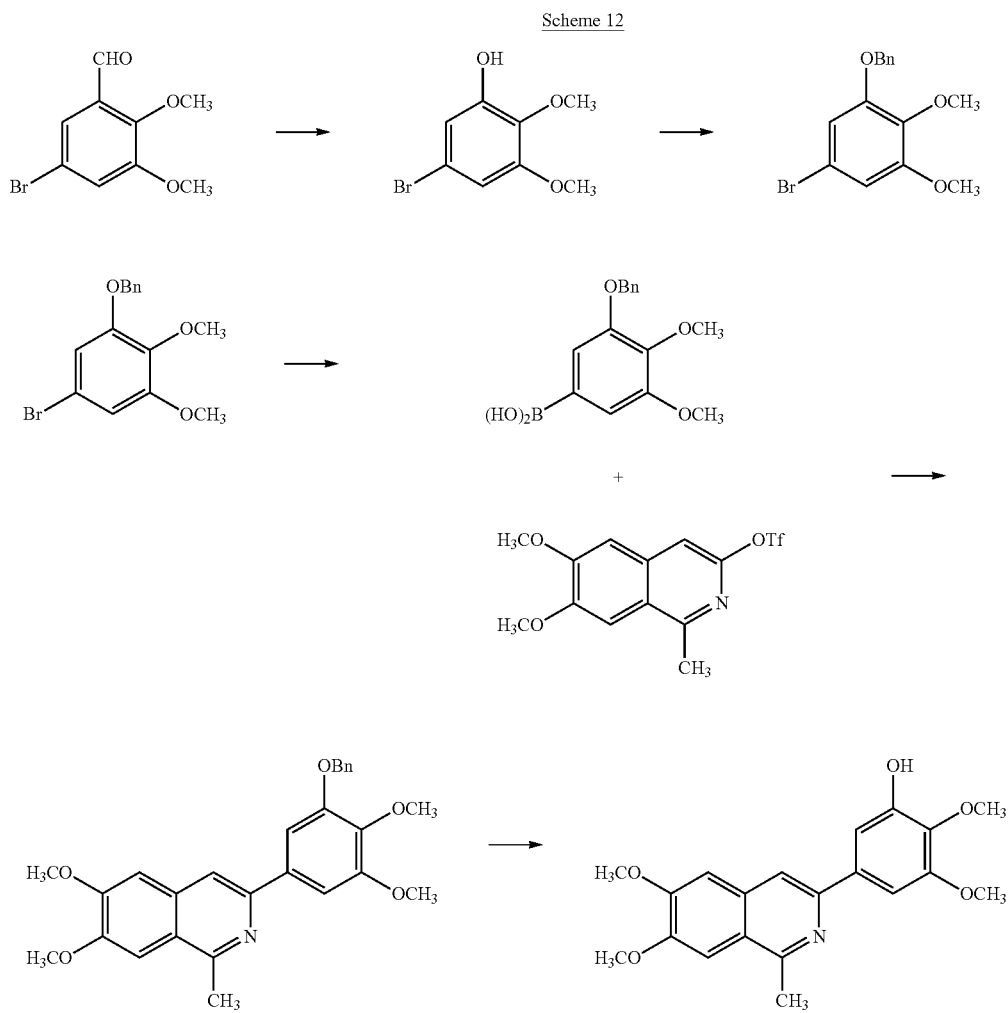

-continued
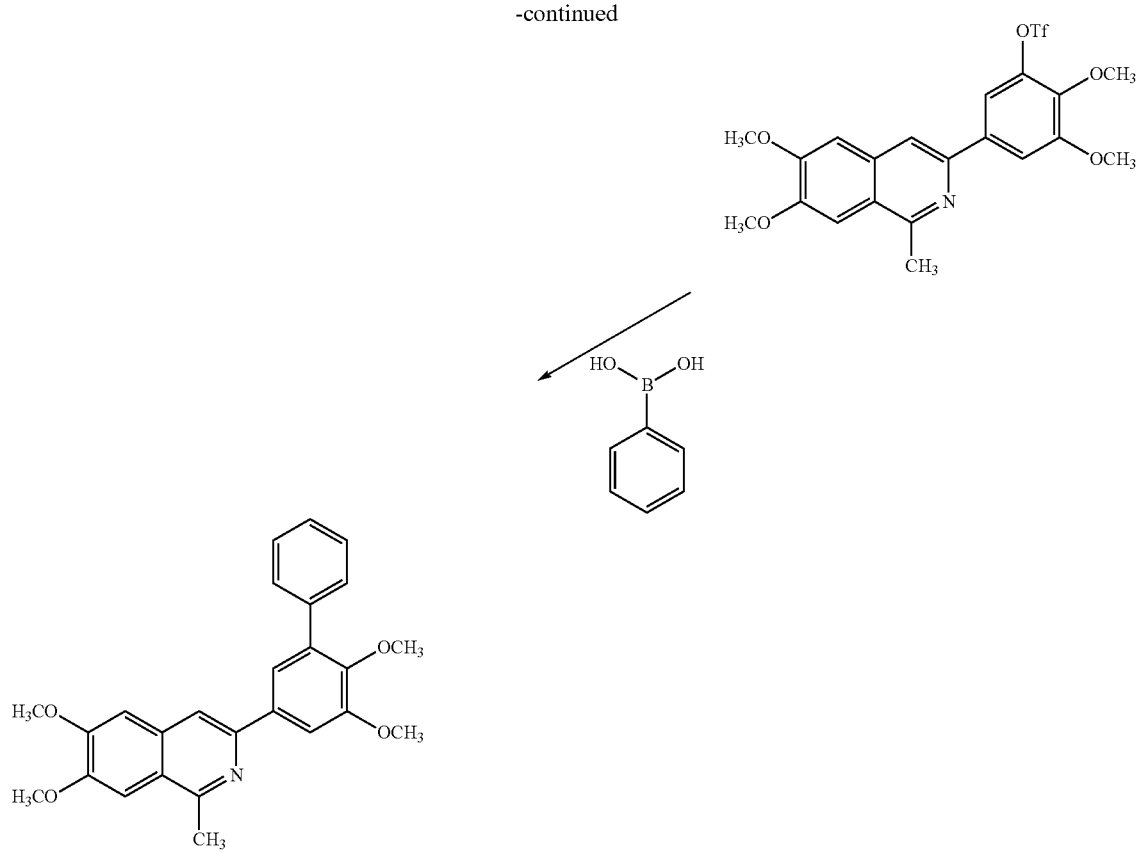
Scheme 13 illustrates methods and intermediates that are useful for preparing $R^7$ substituted compounds of this invention.
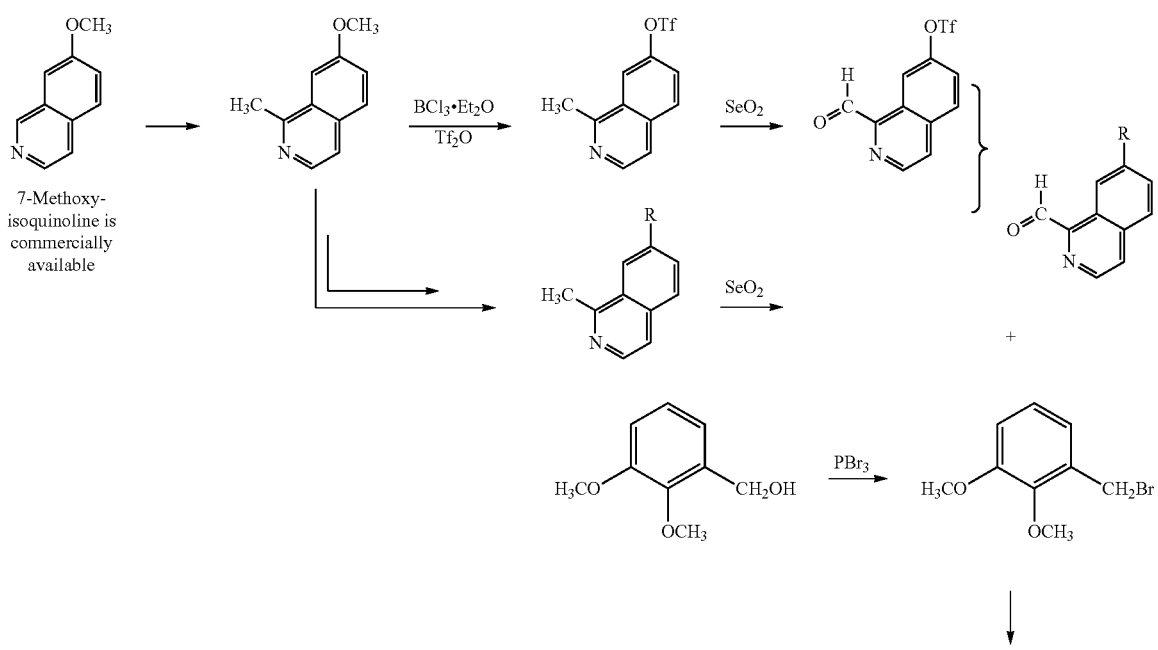

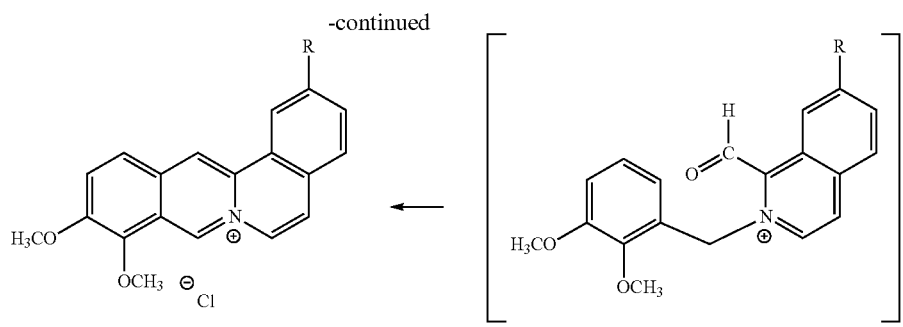
Scheme 14 illustrates methods and intermediates that are useful for preparing $R^6$ substituted compounds of the invention.
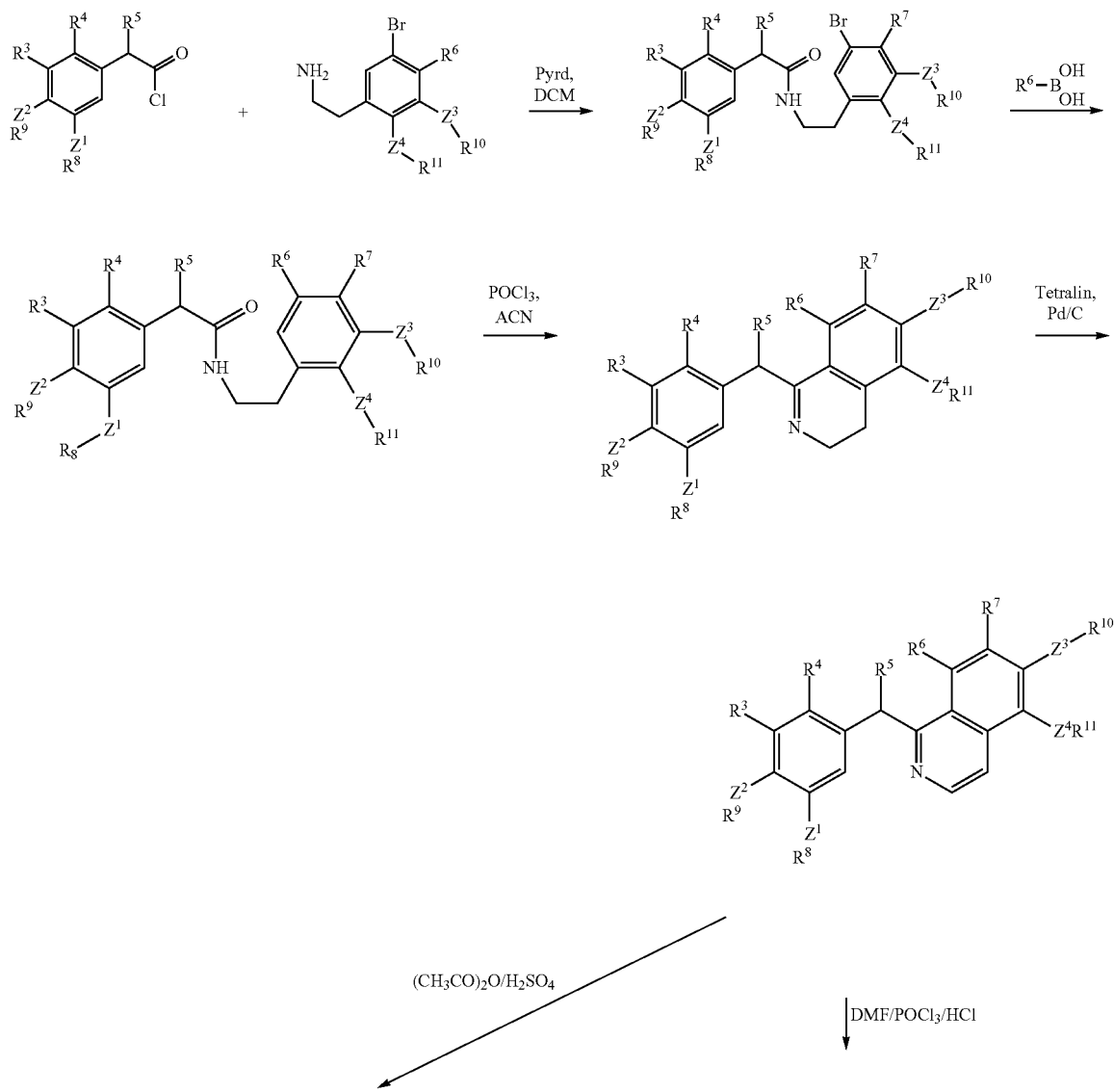

67
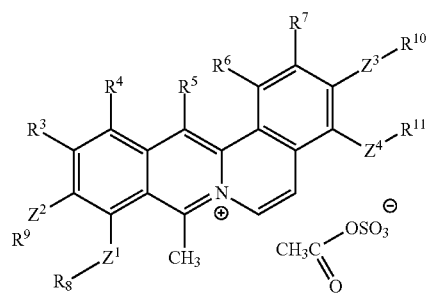
68
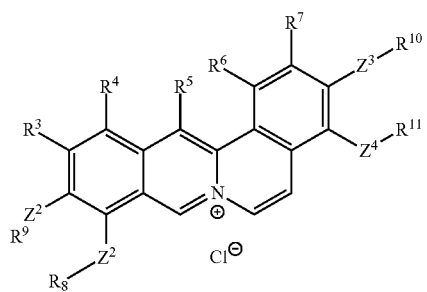
Scheme 15 illustrates methods and intermediates that are useful for preparing $R^6$ substituted compounds of the invention.

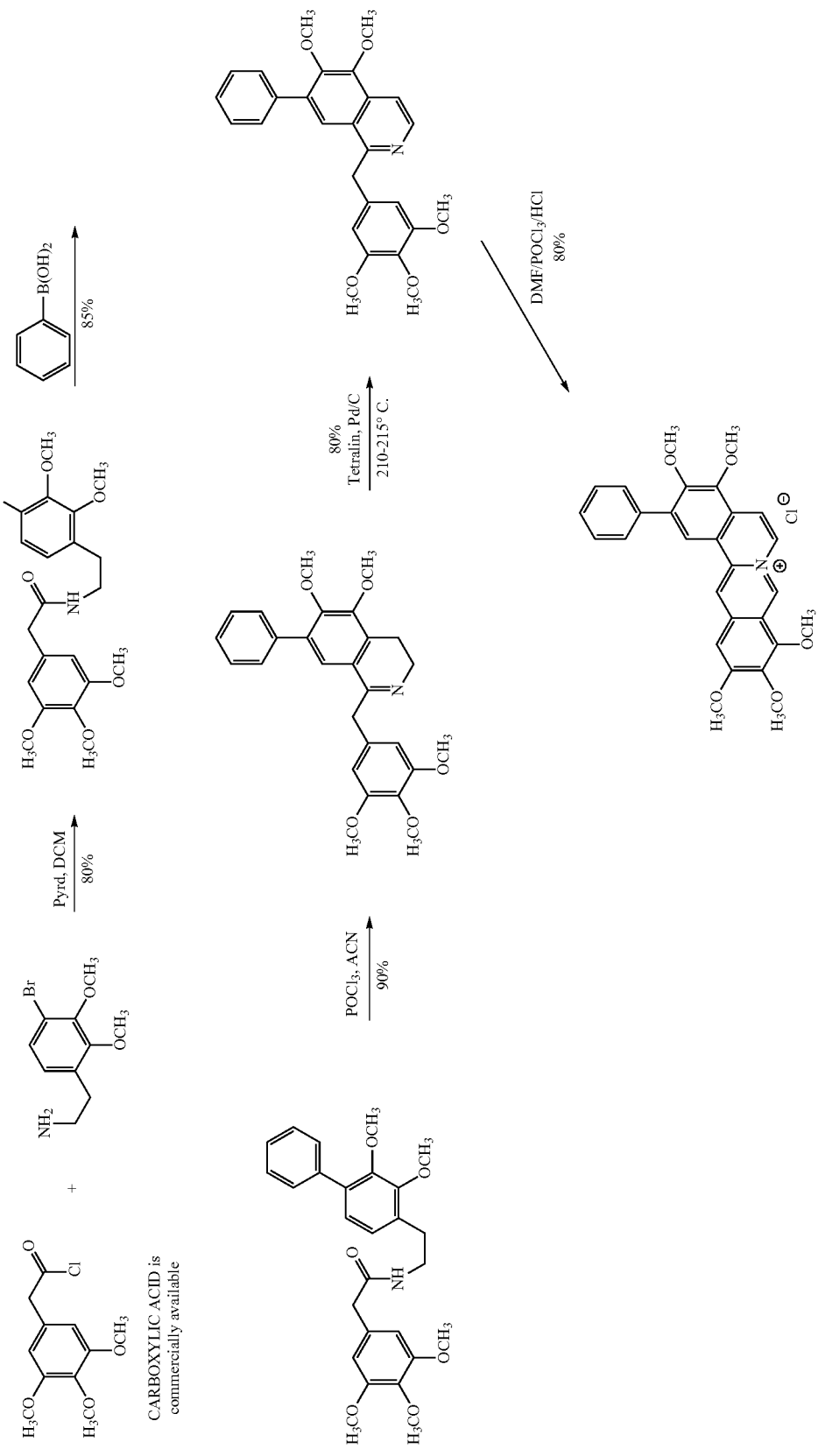

Scheme 16 illustrates methods and intermediates that are useful for preparing $R^7$ substituted compounds of the invention.
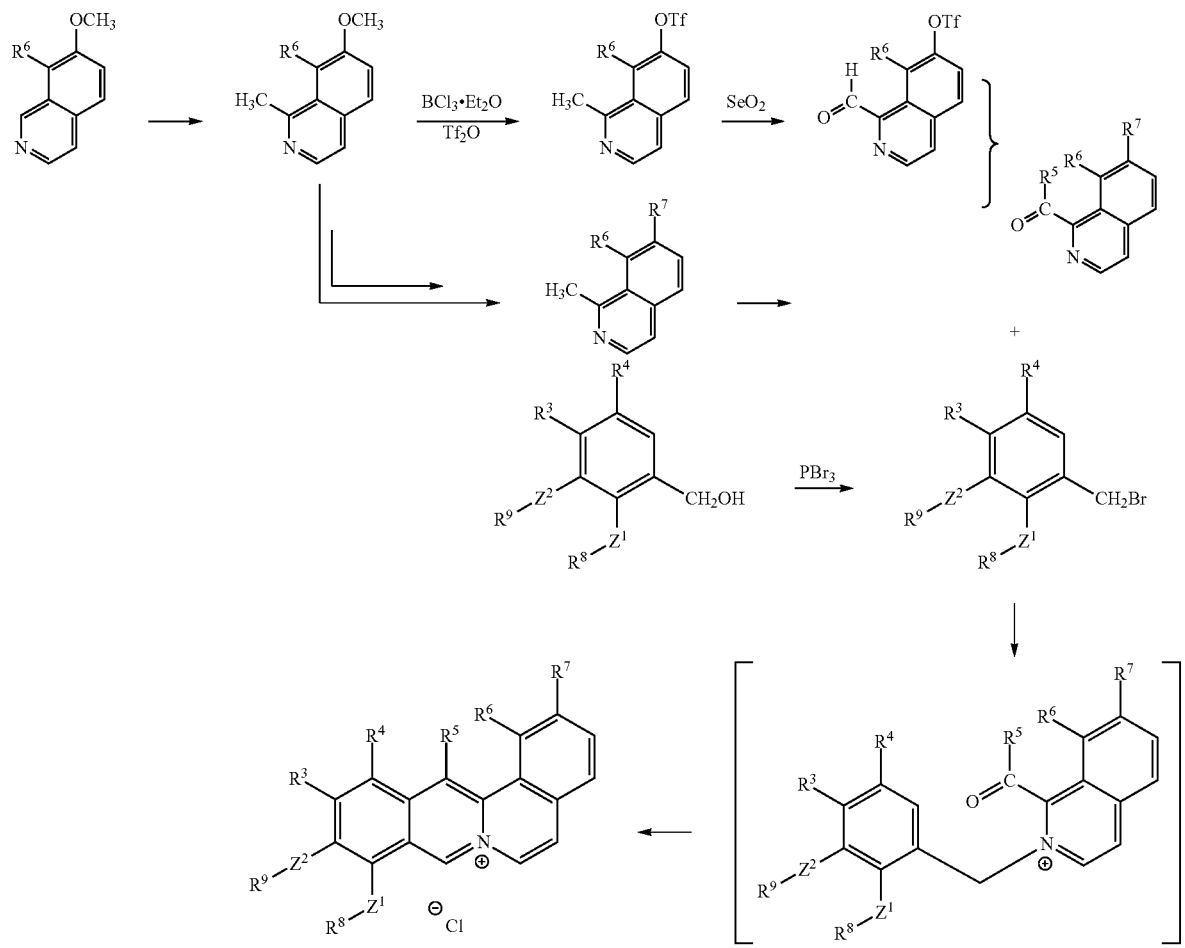
Scheme 17 illustrates methods and intermediates that are useful for preparing $R^6$ substituted compounds of the invention.
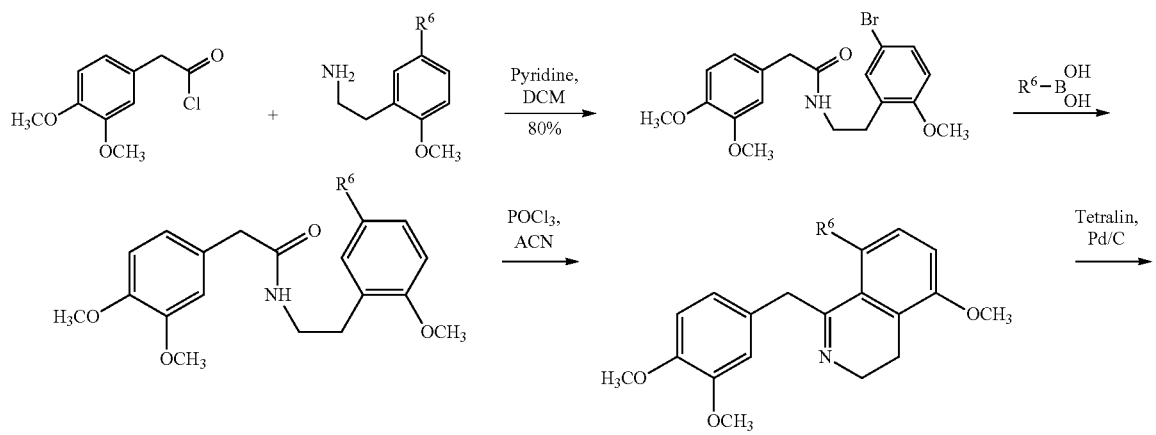

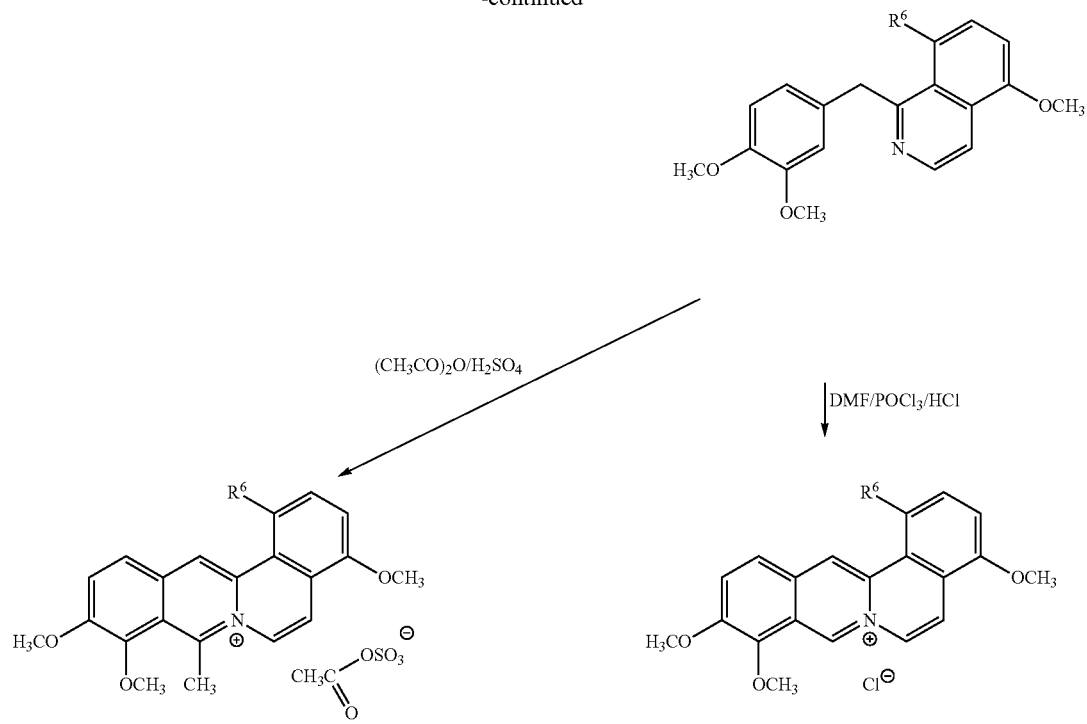
Scheme 18 illustrates methods and intermediates that are useful for preparing R⁴ substituted compounds of the invention.
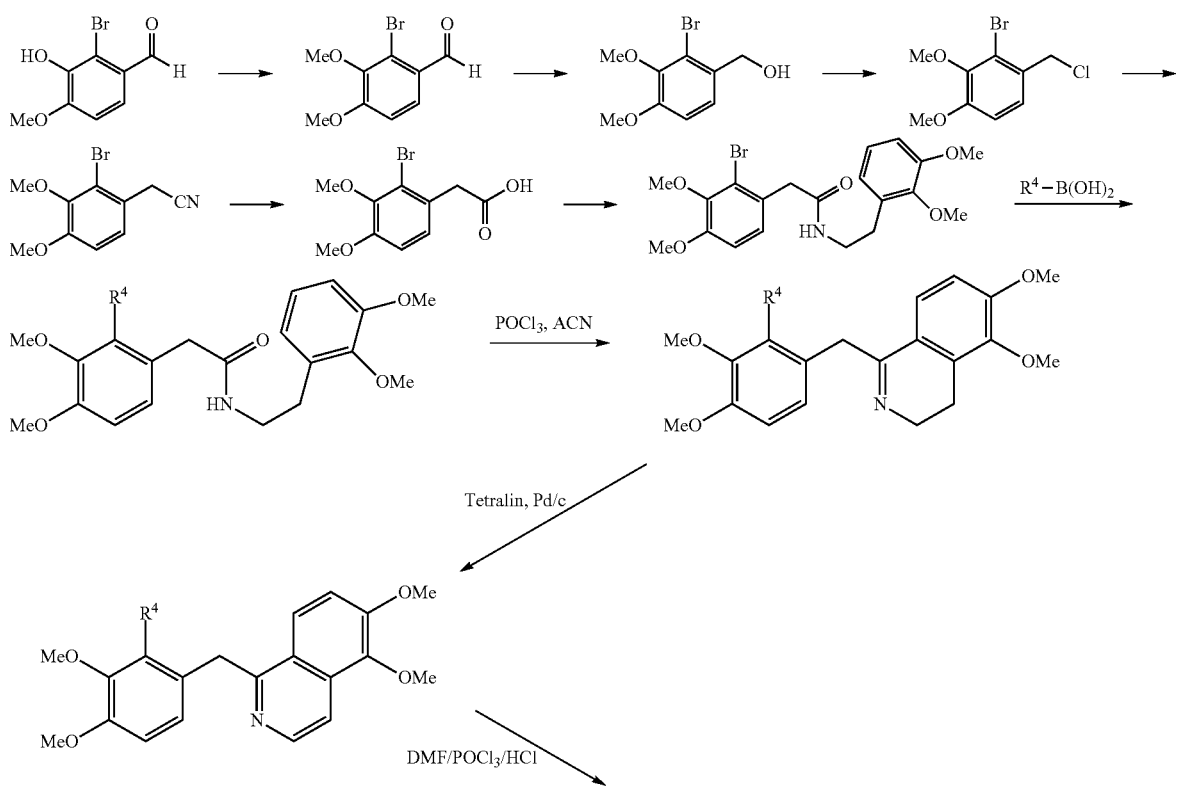

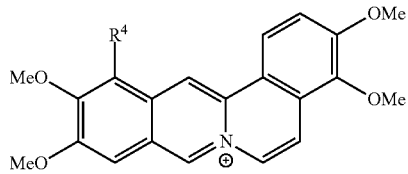

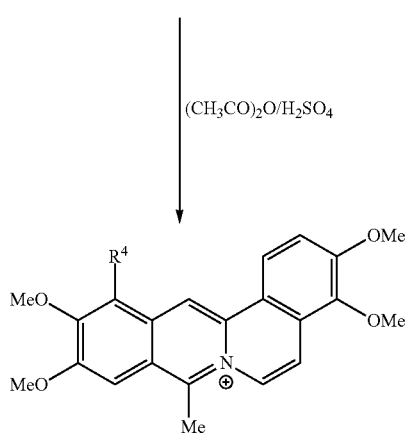

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $CF_3SO_3^-$, $p-CH_3C_6H_4SO_3^-$, citrate, tartrate, malate, fumarate, formate, or acetate.

It will be appreciated by those skilled in the art that a compound of the invention comprising a counterion can be converted to a compound of the invention comprising a different counterion. Such a conversion can be accomplished using a variety of well known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluents, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.1 to about 500 mg/kg, e.g., from about 0.5 to about 400 mg/kg of body weight per day, such as 1 to about 250 mg per kilogram body weight of the recipient per day.

The compound is conveniently formulated in unit dosage form; for example, containing 0.5 to 500 mg, 1 to 400 mg, or 0.5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The ability of a compound of the invention to bind to FtsZ can be determined using a method like Test A described below.

Test A. Determining the FtsZ-Targeting Activities of Compounds of the Invention.

Compound binding to FtsZ can be tested using a fluorescence-based competition binding assay using purified FtsZ and commercially available fluorescent GDP or non-hydrolyzable GTP analogs. One such analog is a GTPγS analog in which the nucleotide is covalently conjugated via its sulfur atom to the fluorescent dye BODIPY (DIPYrromethene BOron difluoride). Upon binding to FtsZ, BODIPY-GTPγS undergoes a dramatic increase in fluorescence emission intensity at 510 nm. The subsequent binding of a compound of the invention results in release of FtsZ-bound BODIPY-GTPγS and a concomitant decrease in fluorescence emission intensity at 510 nm. This binding-induced change in BODIPY-GTPγS fluorescence provides a measure of the equilibrium binding constant (e.g. affinity) of the compound for the protein through analysis of fluorescence titration profiles with standard binding formalisms.

The ability of a compound of the invention to inhibit FtsZ GTPase activity can be determined using a method like Test B described below.

Test B. Determining the FtsZ GTPase Inhibitory Activities of Compounds of the Invention Compound-induced inhibition of the FtsZ GTPase activity can be tested using a colorimetric assay in which the inorganic phosphate ($P_i$) released upon FtsZ-catalyzed hydrolysis of GTP reacts with malachite green and molybdate under acidic conditions to form a ternary complex that absorbs light at 650 nm, thus enabling quantitation of $P_i$ levels by recording the absorbance at 650 nm ($A_{650}$). All reactions are conducted in triplicate in 96-well microtiter plates. Differing concentrations (ranging from 0 to 1.5 mM) of compound are combined with 1 mM GTP and 20 mM $CaCl_2$, the latter being used because FtsZ GTPase activity requires the presence of $Ca^{2+}$ ions. The reactions will be initiated by addition of 2 µM FtsZ and allowed to incubate for 60 minutes at room temperature. Following incubation, the reactions will be stopped by adding 80 µl of an acidic malachite green-molybdate solution containing 0.3 mg/ml malachite green oxalate, 2 mg/ml sodium molybdate, 0.5 mg/ml Triton X-100, and 0.7 N HCl. For the purposes of generating a standard curve, each experiment includes reactions containing known concentrations (ranging from 0 to 10 µM) of monobasic potassium phosphate ($KH_2PO_4$) in place of FtsZ. Ten minutes following addition of the acidic malachite green-molybdate solution, the $A_{650}$ value for each reaction are recorded using a microtiter plate reader. A standard curve of $A_{650}$ versus $P_i$ concentration is constructed using the average $A_{650}$ value obtained for each known $KH_2PO_4$ concentration. This standard curve is then fit by linear regression analysis to yield the quantitative relationship between $A_{650}$ and $P_i$ concentration. The resulting relationship as well as the average $A_{650}$ value for each test reaction is used to calculate the concentrations of $P_i$ released by the GTPase activity of FtsZ. The released $P_i$ concentration in the absence of test compound is set as the mark for 100% GTPase activity, and is used to calculate the percent GTPase activities in reactions containing test compounds. The percent GTPase activity is then plotted as a function of log(compound concentration), with the resulting curves being fit using an appropriate sigmoidal relationship to obtain the compound concentrations at which GTPase activity is inhibited by 50% ($IC_{50}$ values). These $IC_{50}$ values provide quantitative measures of the potencies with which the test compounds of the invention inhibit FtsZ GTPase activity.

The antibacterial activity of a compound of the invention can be determined using methods like Test C and Test D described below.

Test C. Planktonic (Free-Living) Antibacterial Assay.

Planktonic antibacterial activity can be determined using a broth microdilution assay in which log-phase bacteria are grown at 37° C. in appropriate medium containing two-fold serial dilutions of a compound to yield a final concentration ranging from 256 to 0.1 mg/ml. For determination of minimal inhibitory concentration (MIC) values, bacterial growth is monitored after 24 to 48 hours by measuring optical density at 600 nm. MIC values reflect the minimal compound concentrations at which bacterial growth is completely inhibited.

The minimal inhibitory concentration against methicillin-Sensitive *Staphylococcus aureus* (MSSA) for each of the following representative compounds of the invention was determined to be less than 32 µg/ml.

TABLE 5

Minimal Inhibitory Concentrations (MICs) against MSSA for Representative Compounds of the Invention.

| Compound | MIC vs. MSSA (µg/ml) |
| --- | --- |
| Compound of Example 2 | ≤32.0 |
| Compound of Example 4 | ≤32.0 |
| Compound of Example 6 | ≤32.0 |
| Compound of Example 8 | ≤32.0 |
| Compound of Example 12 | ≤32.0 |
| Compound of Example 16 | ≤32.0 |
| Compound of Example 17 | ≤32.0 |
| Compound of Example 19 | ≤32.0 |
| Compound of Example 20 | ≤32.0 |
| Compound of Example 21 | ≤32.0 |
| Compound of Example 27 | ≤32.0 |
| Compound of Example 30 | ≤32.0 |
| Compound of Example 31 | ≤32.0 |
| Compound of Example 35 | ≤32.0 |

Representative compounds of the invention were also tested against Methicillin-Resistant *Staphylococcus aureus*, Vancomycin-Resistant *Enterococcus faecalis*, Vancomycin-Sensitive *Enterococcus faecalis*, *Clostridium difficile*, *Bacillus subtilis*, and *Escherichia coli* and they were found to have significant antibacterial activity.

Test D. Biofilm Antibacterial Assay

Bacteria growing in biofilms frequently exhibit altered sensitivities to antimicrobial agents relative to free-living bacteria. It is therefore important to assess the antibacterial activities of the compounds of the invention against bacteria growing as biofilms. Toward this end, well-established protocols can be used to determine biofilm susceptibilities to compounds. The biofilms are prepared by seeding overnight cultures of bacteria on top of sterile polycarbonate membranes resting on Tryptic Soy Agar (TSA) plates. The plates are inverted and incubated for 48 hours at 37° C. After 48 hours of incubation in the absence of antibiotic, colony biofilms are transferred to fresh TSA plates containing differing compound concentrations. These plates are incubated at 37° C. and the biofilms sampled every hour for four hours and after 24 hours. The biofilms are sampled by placing the membrane and associated bacteria into a tube containing phosphate-buffered water and vortexing at high speed. The resulting cell suspensions are serially diluted and the viable bacteria counted by drop-plating on R2A agar plates. The extent of bacterial killing is calculated relative to the cell count at time zero. Antibacterial potencies are defined by the minimum drug concentrations that eradicate the biofilm (i.e., minimum biofilm eradication concentrations, MBEC).

The following intermediate compounds that are useful for preparing compounds of formula I were prepared.

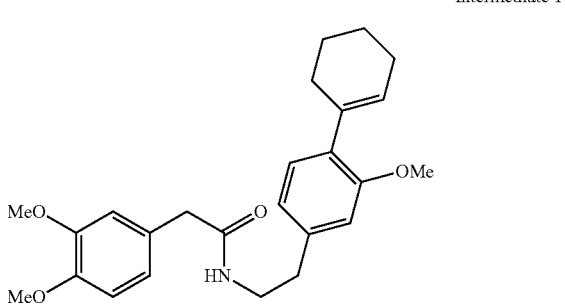

Intermediate 1

N-(4-Bromo-3-methoxyphenylethyl)-2-(3,4-dimethoxyphenyl)acetamide (100 mg), 1-cyclohexeneboronic acid (2 equivalents), palladium acetate (0.05 equivalents), potassium phosphate (3.5 equivalents), and tricyclohexylphospine (0.1 equivalents) were combined in a 2-neck round bottom flask and degassed for 1 hour under vacuum. 3 mL of a toluene/water solution (20:1) was then added to the flask, and the reaction mixed was refluxed at 100° C. under nitrogen for 3 hours. The reaction mixture was then cooled to room temperature and the catalyst was filtered out. The organic layer was then washed with saturated $NaHCO_3$ solution, dried over sodium sulfate, and concentrated under vacuum. Purification with chromatography on silica using 70% ethyl acetate/hexane yielded product as a white solid in 75% yield. $^1$H NMR (400 MHz) ($CDCl_3$) δ 1.68-1.75 (m, 4H), 2.20 (m, 2H), 2.34 (m, 2H), 2.73 (t, 2H), 3.50 (m, 4H), 3.77 (s, 3H), 3.86 (s, 3H), 3.89 (s, 3H), 5.48 (bs, 1H), 5.75 (m, 1H), 6.59 (m, 2H), 6.81 (d, J=8.0 Hz, 1H), 7.00 (d, J=8.0 Hz, 1H).

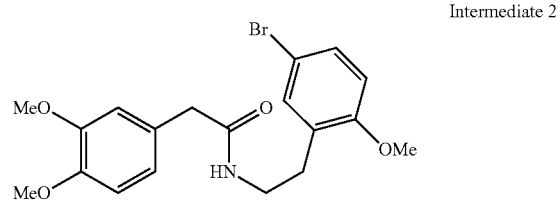 [SMILES: COc1ccc(Br)cc1CCNC(=O)Cc1ccc(OC)c(OC)c1]

Intermediate 2

This intermediate was prepared by reaction of 2-bromo-6-methoxyphenethylamine with the acid chloride of 3,4-dimethoxyacetic acid. $^1$H NMR (400 MHz) ($CDCl_3$) δ 2.73 (m, 2H), 3.47 (m, 4H), 3.71 (s, 3H), 3.84 (s, 3H), 3.88 (s, 3H), 5.58 (m, 1H), 6.66-6.74 (m, 3H), 6.85 (d, J=4.0 Hz, 1H), 7.13 (s, 1H), 7.27 (d, J=8.0 Hz, 1H).

Intermediate 3

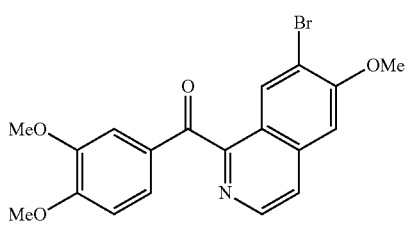

This intermediate was prepared by aromatization of 1-(3,4-dimethoxybenzyl)-7-bromo-6-methoxy-1,2-dihydroisoquinoline with DDQ in the presence of H$_2$O. $^1$H NMR (400 MHz) (CDCl$_3$) δ 3.87 (s, 3H), 3.89 (s, 3H), 3.99 (s, 3H), 6.78 (d, J=8.0 Hz, 1H), 7.09 (s, 1H), 7.32 (dd, J=8.0 Hz, 4.0 Hz, 1H), 7.61 (d, J=8.0 Hz, 1H), 7.64 (s, 1H), 8.36 (s, 3H), 8.46 (d, J=8.0 Hz, 1H).

The following illustrates representative methods for preparing boronates with protected phenolic functionality that are suitable for conversion to intermediate triflates.

a) Preparation of Substituted Bromophenols

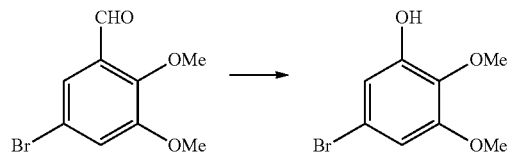 [SMILES: COc1cc(Br)cc(C=O)c1OC ; COc1cc(Br)cc(O)c1OC]

A freshly prepared mixture of 30% H$_2$O$_2$ (3.9 g), formic acid (11 mL), and concentrated sulfuric acid (3 drops) was maintained for 1 hour at room temperature. The mixture was then cooled to 5° C. and treated with a solution of 5-bromo-2,3-dimethoxybenzaldehyde (4.15 g) in formic acid (25 mL). The mixture was maintained for 4 hours at 5° C. then placed in the 4° C. freezer overnight. Reaction mixture was then treated with a solution of Na$_2$SO$_3$ (3.4 g) in water (100 mL), stirred, and extracted with ethyl acetate (3×50 mL). The combined extracts were washed with 50 mL water followed by 50 mL brine and then organic layer was dried over sodium sulfate and concentrated under vacuum. The residue was dissolved in diethyl ether (20 mL) and after addition of 25% aqueous KOH (220 mL) was vigorously stirred under nitrogen. The organic layer was separated, the aqueous phase acidified to a pH of 3 with 2 N HCl and extracted with ethyl acetate (3×100 mL). The combined organic layers were washed with brine, dried over sodium sulfate, and concentrated under vacuum to yield an oily residue which was purified by chromatography on silica in 3:1 hexane/ethyl acetate to provide 2,3-dimethoxy-5-bromophenol in 50% yield. $^1$H NMR (400 MHz) (CDCl$_3$) δ 3.87 (s, 3H), 3.89 (s, 3H), 5.84 (s, 1H), 6.64 (d, J=4.0 Hz, 1H), 6.80 (d, J=4.0 Hz, 1H).

b) Formation of Benzyl Ether of Substituted Bromophenol

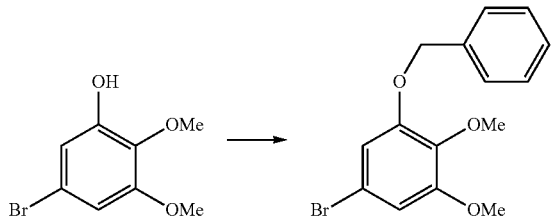 [SMILES: COc1cc(Br)cc(O)c1OC ; COc1cc(Br)cc(OCc2ccccc2)c1OC]

NaH (60% in mineral oil, 300 mg) was added in 3 equal portions to a cooled 0° C. solution of 5-bromo-2,3-dimethoxyphenol (1.16 g) in DMF (10 mL) After 20 minutes, benzyl bromide (0.9 ml) was added, and the reaction mixture was allowed to warm to room temperature and stir overnight. The reaction mixture was then poured into 100 mL of water and extracted with ethyl acetate (4×50 mL). The combined organic layer was then washed with water (4×75 mL) followed by brine (75 mL) and then dried over sodium sulfate and concentrated under vacuum. Chromatography on silica with 5% ethyl acetate/hexane provided 3-benzyloxy-4,5-dimethoxybromobenzene as a colorless oil (1.4 g). $^1$H NMR (400 MHz) (CDCl$_3$) δ 3.87 (s, 6H), 5.12 (s, 2H), 6.75 (s, 1H), 6.80 (s, 1H), 7.34-7.47 (m, 5H).

c) Formation of Boronic Acid Derivative of Substituted Benzyloxyphenyl Compounds

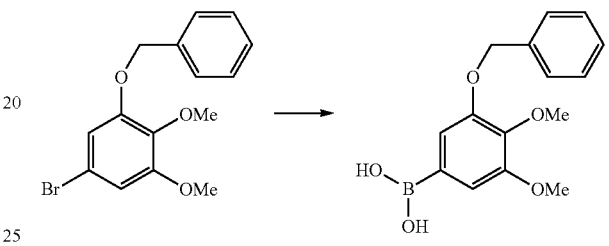

To a 3-neck round bottom flask fitted with a thermometer and under nitrogen atmosphere was added 3-benzyloxy-4,5-dimethoxybromobenzene (426 mg) and dry THF (3 mL). The reaction mixture was cooled to −78° C. and left stirring under nitrogen for 30 minutes. During this time, the reaction was degassed and refilled with nitrogen three times. n-Butyllithium (1.6 M, 0.3 mL) was added dropwise via syringe making sure that the temperature did not exceed −72° C. The reaction was allowed to stir for 30 minutes at −78° C. following the addition of n-butyllithium. Trimethylborate (0.15 mL) was then added dropwise at −78° C., and the reaction mixture was allowed to warm to room temperature over 4-5 hours. The solution was then cooled to −20° C. and acidified with 10% HCl to a pH of 2-3 and allowed to warm to room temperature. The boronic acid was extracted with ethyl acetate and washed once with brine. Organic layer was then dried over sodium sulfate. Following filtration, the volume of solvent was decreased under vacuum until precipitation of boronic acid was observed. Excess hexane was added, and the precipitate filtered to yield product confirmed by LCMS.

The invention will now be illustrated by the following non-limiting Examples.

EXAMPLES

Example 1

Preparation of Compound

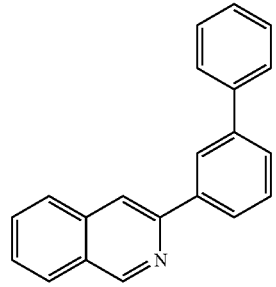 [SMILES: c1ccc(-c2cccc(-c3cc4ccccc4cn3)c2)cc1]

To a mixture of isoquinolin-3-yl trifluoromethanesulfonate (98 mg, 0.37 mmol), biphenyl-3-boronic acid (146 mg, 0.74 mmol) in toluene (4 ml) was added 2N Na$_2$CO$_3$ (370 µl), followed by addition of bis(triphenylphosphine)palladium (II) dichloride (26 mg, 0.037 mmol). The resulting mixture was stirred at 80° C. for overnight, then concentrated under reduced pressure. The crude reaction mixture was diluted with EtOAc and filtered through a pad of Celite. The filtrate was concentrated under reduced pressure and purified on silica gel eluting with 30% EtOAc/hexane to give the title compound as a solid (59 mg, 57%). $^1$H NMR (CDCl$_3$) δ 9.30 (s, 1H), 8.30 (t, 1H), 8.10 (s, 1H), 8.03 (d, 1H), 7.93 (d, 1H), 7.82 (d, 1H), 7.61-7.65 (m, 3H), 7.58 (t, 1H), 7.52 (d, 2H), 7.43-3.77 (m, 2H), 7.30-7.36 (m, 1H).

The intermediate isoquinolin-3-yl trifluoromethanesulfonate was prepared as follows.

a. Preparation of Compound

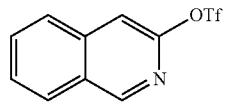 [SMILES: O=S(=O)(Oc1cc2ccccc2cn1)C(F)(F)F]

To a mixture of 3-hydroxyisoquinoline (300 mg, 2.07 mmol) in dichloromethane (18 ml) was added triethylamine (580 µl, 4.14 mmol), followed by addition of triflic anhydride (424 µl, 2.52 mmol) by syringe. The resulting mixture was stirred at room temperature for 1 hour, and then was diluted with dichloromethane, washed with H$_2$O, and then with brine. The organic layer was dried over Na$_2$SO$_4$ and concentrated under reduced pressure. The crude compound was purified on silica gel eluting with dichloromethane to give the title compound as a solid (280 mg, 51%). $^1$H NMR (CDCl$_3$) δ 8.99 (s, 1H), 7.98 (d, 1H), 7.82 (d, 1H), 7.76 (t, 1H), 7.60 (t, 1H), 7.50 (s, 1H).

Example 2

Preparation of Compound

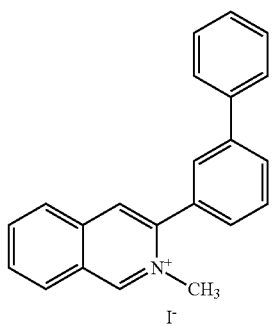 [SMILES: C[n+]1cc2ccccc2cc1-c1cccc(-c2ccccc2)c1 ; [I-]]

A mixture of 3-(biphenyl-3-yl)isoquinoline (20 mg, 0.071) and iodomethane (200 mg, 1.42 mmol) was stirred overnight. The excessive iodomethane was removed under reduced pressure and the crude compound was triturated with hexane/dichloromethane to give the yellow solid (12 mg, 41%). $^1$H NMR (DMSO-d) δ 10.30 (s, 1H), 9.32 (s, 1H), 9.05 (d, 1H), 8.30-8.33 (m, 2H), 8.25 (t, 1H), 8.01 (s, 1H), 7.99 (d, 1H), 7.70-7.85 (m, 4H), 7.51 (t, 2H), 7.47 (t, 1H), 4.25 (s, 3H).

Example 3

Preparation of Compound

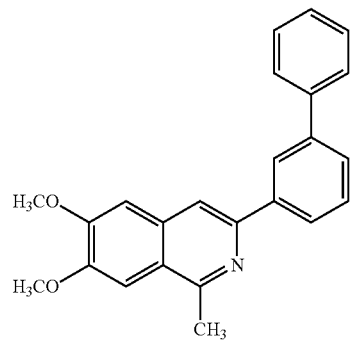

To a mixture of 6,7-dimethoxy-1-methylisoquinolin-3-yl-trifluoromethanesulfonate (113 mg, 0.359 mmol) and biphenyl-3-boronic acid (142 mg, 0.72 mmol) in toluene (4 ml) was added 2N Na$_2$CO$_3$ (360 µl), followed by addition of bis(triphenylphosphine)palladium (II) dichloride (25 mg, 0.036 mmol). The resulting mixture was stirred at 80° C. for 3 hours, then concentrated under reduced pressure. The crude reaction mixture was diluted with EtOAc and filtered through a pad of Celite. The filtrate was concentrated under reduced pressure and the reaction mixture was purified on silica gel eluting with 40% EtOAc/hexane to give the title compound as a solid (69 mg, 58%). $^1$H NMR (CDCl$_3$) δ 8.28 (s, 1H), 8.01 (d, 1H), 7.80 (s, 1H), 7.61-7.59 (m, 2H), 7.55-7.40 (m, 3H), 7.35 (t, 1H), 7.31 (t, 1H), 7.20 (s, 1H), 7.05 (s, 1H), 4.05 (s, 3H), 4.02 (s, 3H), 2.82 (s, 3H).

The intermediate 6,7-dimethoxy-1-methylisoquinolin-3-yl trifluoromethanesulfonate was prepared as follows.

a. Preparation of Compound

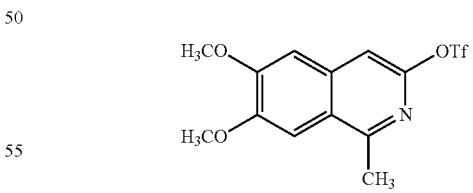

To a suspension of 6,7-dimethoxy-1-methylisoquinolin-3-ol (500 mg, 2.56 mmol) in dichloromethane (22 ml) was added triethylamine (517 µl, 3.08 mmol), followed by addition of triflic anhydride (517 µl, 3.08 mmol) by syringe. The resulting mixture was stirred at room temperature for 2 hours, and then was diluted with dichloromethane, washed with H$_2$O, brine. The organic layer was dried over Na$_2$SO$_4$ and concentrated under reduced pressure. The crude compound was purified on silica gel eluting with dichloromethane to give the title compound as a solid (420 mg, 52%). $^1$H NMR (CDCl$_3$), δ, 7.30 (s, 1H), 7.29 (s, 1H), 4.05 (s, 3H), 4.06 (s, 3H), 2.90 (s, 3H).

Example 4

Preparation of Compound

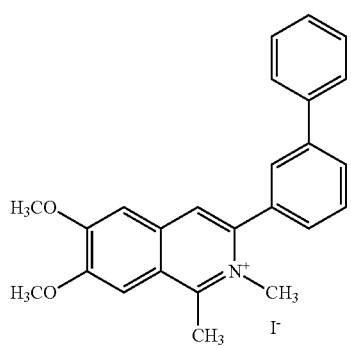 [SMILES: COc1cc2cc(-c3cccc(-c4ccccc4)c3)[n+](C)c(C)c2cc1OC ; [I-]]

A mixture of 3-(biphenyl-3-yl)-6,7-dimethoxy-1-methyl-isoquinoline (35 mg) and iodomethane (1.5 ml) was refluxed for 3 hours. The excessive iodomethane was removed under reduced pressure and the crude compound was purified on silica gel eluting with 10% methanol/dichloromethane to give the yellow solid (5 mg, 10%). $^1$H NMR (CDCl$_3$), δ, 7.88 (s, 1H), 7.60 (s, 1H), 7.58-7.42 (m, 2H), 7.15-7.02 (m, 4H), 7.51 (t, 1H), 7.44-7.30 (m, 4H), 7.28 (t, 1H), 7.24 (s, 1H), 4.05 (s, 3H), 4.50 (s, 3H), 4.05 (s, 3H), 4.02 (s, 3H), 3.35 (s, 3H).

Example 5

Preparation of Compound

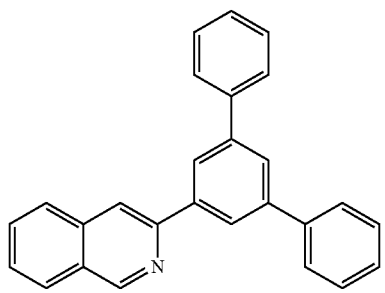 [SMILES: c1ccc(-c2cc(-c3ccccc3)cc(-c3cc4ccccc4cn3)c2)cc1]

To a mixture of isoquinolin-3-yl trifluoromethanesulfonate (80 mg, 0.30 mmol), 1,1':3',1''-terphenyl-5'-boronic acid (165 mg, 0.60 mmol) in toluene (4 ml) was added 2N Na$_2$CO$_3$ (302 μl, 0.60 mmol), followed by addition of bis(triphenylphosphine)palladium (II) dichloride (42 mg, 0.06 mmol). The resulting mixture was stirred at 80° C. for 4 hours, and then concentrated under reduced pressure. The crude reaction mixture was diluted with EtOAc and filtered through a pad of Celite. The filtrate was concentrated under reduced pressure and purified on silica gel eluting with 10% EtOAc/hexane to give the title compound as a solid (51 mg, 48%). $^1$H NMR (CDCl$_3$) δ 9.26 (s, 1H), 8.28 (s, 1H), 8.10 (s, 1H), 7.98-7.92 (m, 2H), 7.82-7.78 (m, 3H), 7.68-7.63 (m, 4H), 7.62-7.58 (m, 2H), 7.51 (t, 1H), 7.42-7.40 (m, 2H), 7.37-7.34 (m, 2H).

Example 6

Preparation of Compound

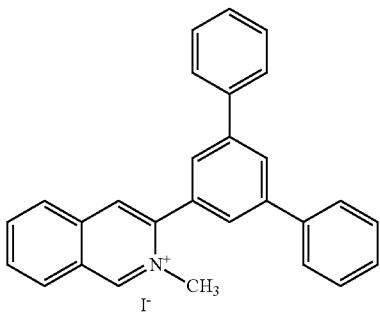 [SMILES: C[n+]1cc2ccccc2cc1-c1cc(-c2ccccc2)cc(-c2ccccc2)c1 ; [I-]]

A mixture of 3-(1,1':3',1''-terphenyl-5'-yl) isoquinoline (35 mg, 0.12 mmol) and iodomethane (1 ml) was refluxed overnight. The excessive iodomethane was removed under reduced pressure and the crude compound was purified on silica gel eluting with 3% methanol/dichloromethane to give the yellow solid (23 mg, 37%). $^1$H NMR (CDCl$_3$) δ 11.55 (s, 1H), 8.78 (d, 1H), 8.14 (s, 1H), 8.22-7.95 (m, 4H), 7.90 (s, 1H), 7.70-7.58 (m, 4H), 7.48-7.40 (m, 4H), 7.35 (t, 1H).

Example 7

Preparation of Compound

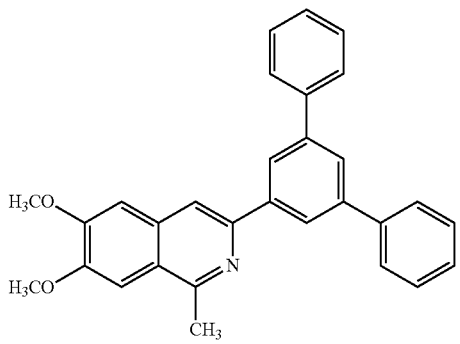

To a mixture of 6,7-dimethoxy-1-methylisoquinolin-3-yl-trifluoromethanesulfonate (84 mg, 0.27 mmol), 1,1':3',1''-terphenyl-5'-boronic acid (110 mg, 0.40 mmol) in actonitrile (1 ml) was added K$_2$CO$_3$ (92 mg, 0.604 mmol), followed by addition of 2-dicyclohexylphosphino-2',4',6'-triisopropylbiphenyl (13 mg, 0.027 mmol) and Pd(OAc)$_2$ (3 mg, 0.013 mmol). The resulting mixture was refluxed for overnight, and then concentrated under reduced pressure. The crude reaction mixture was diluted with EtOAc and filtered through a pad of Celite. The filtrate was concentrated under reduced pressure and purified on silica gel eluting with 10% EtOAc/hexane to give the title compound as a solid (56 mg, 49%). $^1$H NMR (CDCl$_3$), δ, 8.26 (s, 1H), 8.25 (s, 1H), 7.87 (s, 1H), 7.75 (s, 1H), 7.70-7.66 (m, 4H), 7.45-7.38 (m, 4H), 7.36-7.30 (m, 2H), 7.25 (s, 1H), 7.20 (s, 1H), 4.00 (s, 3H), 3.99 (s, 3H), 2.90 (s, 3H).

Example 8

Preparation of Compound

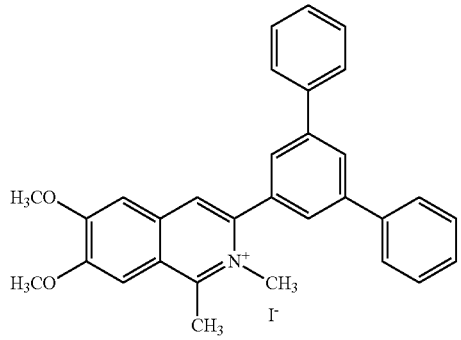 [SMILES: COc1cc2cc(-c3cc(-c4ccccc4)cc(-c4ccccc4)c3)[n+](C)c(C)c2cc1OC ; [I-]]

A mixture of 6,7-dimethoxy-1-methyl-3-(1,1':3',1''-terphenyl-5'-yl) isoquinoline (25 mg, 0.058 mmol) and iodomethane (1 ml) was refluxed for overnight. The excessive iodomethane was removed under reduced pressure and the crude compound was purified on silica gel eluting with 5% methanol/dichloromethane to give the yellow solid (6 mg, 20%). $^1$H NMR (CDCl$_3$) δ 8.22 (s, 1H), 7.92 (s, 1H), 7.80 (s, 1H), 7.78 (s, 1H), 7.72-7.68 (m, 4H), 7.60 (s, 1H), 7.46-7.38 (m, 4H), 7.36-7.30 (m, 2H), 7.22 (s, 1H), 4.40 (s, 3H), 3.90 (s, 3H), 3.81 (s, 3H), 3.25 (s, 3H).

Example 9

Preparation of Compound

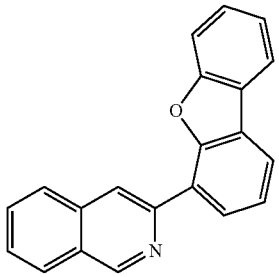 [SMILES: c1ccc2cc(-c3cccc4c3oc3ccccc34)ncc2c1]

To a mixture of isoquinolin-3-yl trifluoromethanesulfonate (98 mg, 0.370 mmol), dibenzofuran-4-boronic acid (94 mg, 0.443 mmol) in toluene (4 ml) was added 2N Na$_2$CO$_3$ (370 µl), followed by addition of bis(triphenylphosphine)palladium (II) dichloride (26 mg, 0.037 mmol). The resulting mixture was stirred at 80° C. for overnight, and then concentrated under reduced pressure. The crude reaction mixture was diluted with EtOAc and filtered through a pad of Celite. The filtrate was concentrated under reduced pressure and purified on silica gel eluting with 20% EtOAc/Hexane to give the title compound as a white solid (78 mg, 72%). $^1$H NMR (CDCl$_3$) δ 9.25 (s, 1H), 8.65 (s, 1H), 8.30 (d, 1H), 7.88-7.82 (m, 4H), 7.62-7.52 (m, 2H), 7.48-7.52 (t, 1H), 7.38-7.32 (m, 2H), 7.21 (t, 1H).

Example 10

Preparation of Compound

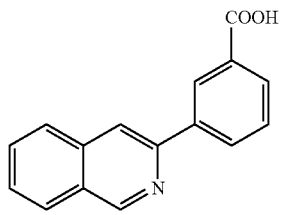 [SMILES: O=C(O)c1cccc(-c2cc3ccccc3cn2)c1]

To a mixture of isoquinolin-3-yl trifluoromethanesulfonate (91 mg, 0.34 mmol), 3-carboxyphenyl boronic acid (68 mg, 0.41 mmol) in toluene (4 ml) was added 2N Na$_2$CO$_3$ (343 µl), followed by addition of tetrakis(triphenylphosphine)palladium (39 mg, 0.034 mmol). The resulting mixture was stirred at 80° C. for overnight, and then concentrated under reduced pressure. The crude reaction mixture was diluted with EtOAc and filtered through a pad of Celite. The filtrate was concentrated under reduced pressure and purified on silica gel eluting with 2% MeOH/CH$_2$Cl$_2$ to give the title compound as a white solid (21 mg, 25%). $^1$H NMR (CDCl$_3$) δ 9.85 (s, 1H), 7.64 (s, 1H), 7.62-7.58 (m, 2H), 7.57-7.53 (d, 1H), 7.50 (m, 2H), 7.43-7.36 (m, 4H).

Example 11

Preparation of Compound

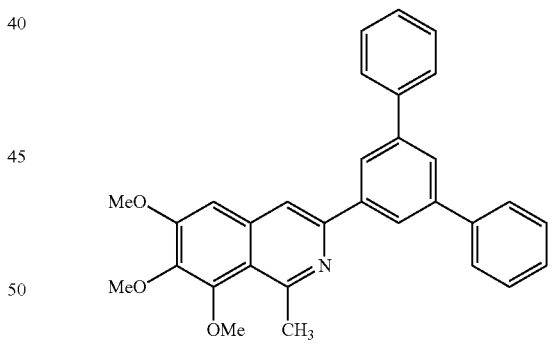

A 50-mL round bottom flask equipped with a magnetic stirrer, a condenser and a nitrogen in/outlet adapter was charged with 6,7,8-trimethoxy-1-methylisoquinolin-3-yl trifluoromethanesulfonate (100 mg, 0.26 mmol), 1,1':3',1''-terphenyl-5'-boronic acid (108 mg, 0.39 mmol), water/acetonitrile (5 mL/10 ml), K$_2$CO$_3$ (90 mg, 0.66 mmol), 2-dicyclohexylphosphino-2',4',6'-triisopropylbiphenyl (12.5 mg, 0.03 mmol). The resulting solution was degassed for 5 minutes, then Pd(OAc)$_2$ (3.0 mg, 0.013 mmol) was added and the solution was carefully degassed. The reaction mixture was warmed to 90° C. and stirred for 12 hours. After cooled to 20° C., the reaction mixture was diluted with CH$_2$Cl$_2$ (60 mL) and washed with brine (20 mL). The organic layer was passed through a pad of Celite, then concentrated under reduced pressure and purified on silica gel. Elution with CH$_2$Cl$_2$ afforded the title compound (108 mg, 90%) as a white foam solid. $^1$H NMR (CDCl$_3$, 400 MHz) δ 8.24 (d, 2H, J=1.72 Hz), 7.79 (s, 1H), 7.75 (m, 1H), 7.68-7.70 (m, 41I), 7.40-7.44 (m, 4H), 7.32-7.34 (m, 2H), 6.83 (s, 1H), 3.97 (s, 3H), 3.95 (s, 3H), 3.91 (s, 3H), 3.10 (s, 3H).

The intermediate 6,7,8-trimethoxy-1-methylisoquinolin-3-yl trifluoromethanesulfonate was prepared as follows.

a. Preparation of Compound

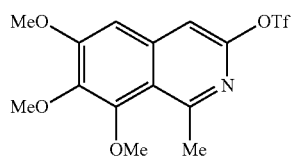 [SMILES: COc1cc2cc(OS(=O)(=O)C(F)(F)F)nc(C)c2c(OC)c1OC]

A 50-mL round bottom flask equipped with a magnetic stirrer under nitrogen was charged with 6,7,8-trimethoxy-1-methylisoquinolin-3-ol (200 mg, 0.80 mmol), CH$_2$Cl$_2$ (15 mL), and triethylamine (0.22 ml, 1.60 mmol). After cooling to −70° C., triflic anhydride (0.15 ml, 0.88 mmol) was added via a syringe. The resulting reaction mixture was stirred at −70 to −40° C. for 30 minutes, then diluted with CH$_2$Cl$_2$ (50 mL) and washed with saturated NaHCO$_3$ (20 mL), brine (20 mL), dried over MgSO$_4$, and concentrated to afford a brown solid. The brown solid was purified on silica gel, and elution with CH$_2$Cl$_2$ afforded the title compound (210 mg, 69%) as a white solid. $^1$H NMR (CDCl$_3$, 400 MHz) δ 7.13 (s, 1H), 6.83 (s, 1H), 3.96 (s, 3H), 3.94 (s, 3H), 3.88 (s, 3H), 2.96 (s, 3H).

Example 12

Preparation of Compound

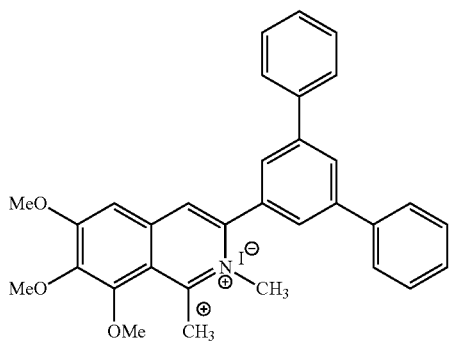

A solution of the 1-methyl-3-(1,1':3',1''-terphenyl-5'-yl)-6,7,8-trimethoxyisoquinoline (75 mg, 0.16 mmol) in iodomethane (1.5 mL) was stirred in a sealed tube at 70° C. overnight. The excessive iodomethane was removed under reduced pressure and the crude compound was triturated with acetone/EtOAc to afford the title compound (50 mg, 51%) as an off white solid. $^1$H NMR (CDCl$_3$, 400 MHz) δ 7.94 (t, 1H, J=1.7 Hz), 7.88 (d, 2H, J=1.7 Hz), 7.85 (s, 1H), 7.67-7.69 (m, 41-1), 7.40-7.44 (m, 4H), 7.31-7.35 (m, 2H), 7.06 (s, 1H), 4.27 (s, 3H), 4.06 (s, 3H), 4.01 (s, 3H), 3.96 (s, 3H), 3.55 (s, 3H).

Example 13

Preparation of Compound

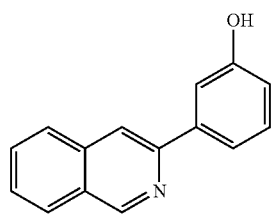 [SMILES: Oc1cccc(-c2cc3ccccc3cn2)c1]

To a mixture of isoquinolin-3-yl trifluoromethanesulfonate (548 mg, 2.07 mmol), 3-hydroxyphenyl boronic acid (570 mg, 4.14 mmol) in toluene (20 ml) was added 2N Na$_2$CO$_3$ (2.06 ml), followed by addition of bis(triphenylphosphine) palladium (II) dichloride (290 mg, 0.41 mmol). The resulting mixture was stirred at 80° C. for 4 hours, then concentrated under reduced pressure. The crude reaction mixture was diluted with EtOAc and filtered through a pad of Celite. The filtrate was concentrated under reduced pressure and the reaction mixture was purified on silica gel eluting with 40-60% EtOAc/hexane to give the title compound as a solid. $^1$H NMR (CDCl$_3$) δ 9.22 (s, 1H), 7.88-7.92 (m, 2H), 7.79 (d, 1H), 7.68-7.60 (m, 2H), 7.42-7.51 (m, 2H), 7.25 (t, 1H), 6.80 (t, 1H).

Example 14

Preparation of Compound

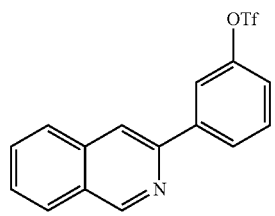 [SMILES: O=S(=O)(Oc1cccc(-c2cc3ccccc3cn2)c1)C(F)(F)F]

To a mixture of 3-(isoquinolin-3-yl)phenol (75 mg, 0.34 mmol) in dichloromethane (4 ml) was added triethylamine (95 μl, 0.68 mmol), followed by addition of triflic anhydride (84 μl, 0.51 mmol) by syringe. The resulting mixture was stirred at room temperature for 2 hours, and then was diluted with dichloromethane, washed with H$_2$O, brine. The organic layer was dried over Na$_2$SO$_4$ and concentrated under reduced pressure. The crude compound was purified on silica gel eluting with 20% EtOAc/Hexane to give the title compound as a solid (68 mg, 57%). $^1$H NMR (CDCl$_3$) δ 9.25 (s, 1H), 8.08 (d, 1H), 8.04 (s, 1H), 8.02 (s, 1H), 7.93 (d, 1H), 7.82 (d, 1H), 7.66 (t, 1H), 7.56 (t, 1H), 7.50 (t, 1H), 7.23 (dd, 1H).

Example 15

Preparation of Compound

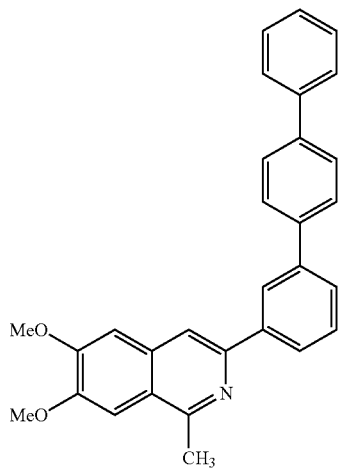 [SMILES: COc1cc2cc(-c3cccc(-c4ccc(-c5ccccc5)cc4)c3)nc(C)c2cc1OC]

A 50-mL round bottom flask equipped with a magnetic stirrer, a condenser and a nitrogen in/outlet adapter was charged with 3-(6,7-dimethoxy-1-methylisoquinolin-3-yl)phenyl trifluoromethanesulfonate (80 mg, 0.19 mmol), 4-biphenylboronic acid (56 mg, 0.28 mmol), water/acetonitrile (5 mL/10 ml), $K_2CO_3$ (65 mg, 0.47 mmol), 2-dicyclohexylphosphino-2',4',6'-triisopropylbiphenyl (9.0 mg, 0.02 mmol). The resulting solution was degassed for 5 minutes, then Pd(OAc)$_2$ (2.1 mg, 0.01 mmol) was added and the reaction mixture was carefully degassed. The reaction solution was heated to 90° C. and stirred for 12 hours. After cooling to 20° C., the reaction mixture was diluted with $CH_2Cl_2$ (60 mL) and washed with brine (20 mL). The organic layer was passed through a pad of Celite, then concentrated in vacuum and purified on silica gel. Elution with 50% EtOAc/hexanes afforded the title compound (63.8 mg, 79%) as a white solid. $^1$H NMR (CDCl$_3$, 400 MHz) δ 8.40 (m, 1H), 8.10-8.12 (m, 1H) 7.91 (s, 1H), 7.82-7.84 (m, 2H), 7.68-7.75 (m, 5H), 7.59 (t, 1H, J=8.0 Hz), 7.46-7.52 (m, 2H), 7.37-7.41 (m, 1H), 7.34 (s, 1H), 7.18 (s, 1H), 4.09 (s, 3H), 4.08 (s, 3H), 3.02 (s, 3H).

Example 16

Preparation of Compound

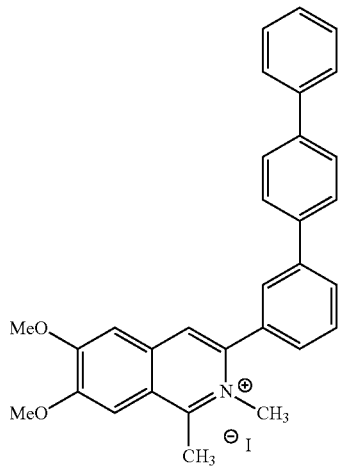 [SMILES: COc1cc2cc(-c3cccc(-c4ccc(-c5ccccc5)cc4)c3)[n+](C)c(C)c2cc1OC ; [I-]]

A solution of 1-methyl-3-(1,1':1',1"-terphenyl-3-yl)-6,7-dimethoxyisoquinoline (60 mg, 0.14 mmol) in iodomethane (1.5 mL) was stirred in a sealed tube at 70° C. overnight. After cooling to room temperature, acetone (10 mL) was added and the solid was collected by filtration. The title compound was obtained as an off white solid (50 mg, 75% yield). $^1$H NMR (CDCl$_3$, 400 MHz) δ 8.21 (s, 1H), 7.97 (t, 1H, J=4 Hz), 7.83-7.85 (m, 3H), 7.74-7.76 (m, 211), 7.62-7.69 (m, 4H), 7.56 (t, 1H, J=8 Hz), 7.47-7.52 (m, 2H), 7.38-7.42 (m, 2H), 4.29 (s, 3H), 4.11 (s, 3H), 4.01 (s, 3H), 3.38 (s, 3H).

Example 17

Preparation of Compound

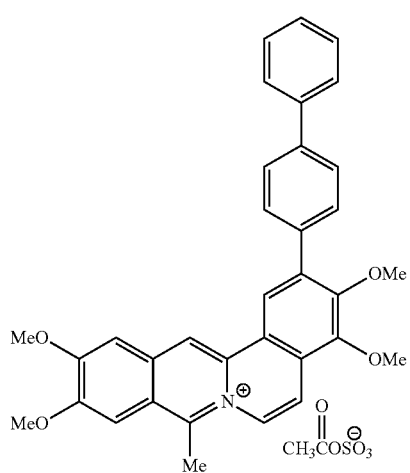

Fuming sulfuric acid (0.2 mL) was added to 0.8 mL freshly distilled acetic anhydride resulting in a vigorous exothermic reaction and the mixture becoming wine-red in color. This mixture was heated at 85-90° C. for 10 minutes. A solution of 7-(biphenyl-4-yl)-1-(3,4-dimethoxybenzyl)-5,6-dimethoxyisoquinoline (24 mg in 1.0 mL) of Ac$_2$O was added under nitrogen to the wine red sulfuric acid solution and the resulting mixture was heated at 85-90° C. for 1 h. The reaction mixture was cooled to room temperature and methanol was added. The solution was then chilled and ether was added until a solid precipitated. The solid was then filtered off, washed with small amount of methanol and ether to furnish a yellowish solid in quantitative yield in high purity. $^1$H NMR (400 MHz) (CDCl$_3$) δ 3.50 (s, 3H), 3.88 (s, 3H), 4.18 (s, 6H), 4.22 (s, 3H), 7.42 (t, J=8.0 Hz, 1H), 7.52 (t, J=8.0 Hz, 2H), 7.76 (d, J=8.0 Hz, 2H) 7.80 (s, 2H), 7.87 (m, 5H), 8.22 (d, J=8.0 Hz, 1H), 8.78 (s, 1H) 8.90 (d, J=8.0 Hz, 1H), 9.65 (s, 1H).

The intermediate 7-(biphenyl-4-yl)-1-(3,4-dimethoxybenzyl)-5,6-dimethoxyisoquinoline was prepared as follows.

a. Preparation of Compound

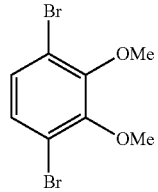 [SMILES: COc1c(Br)ccc(Br)c1OC]

To 1,2-dimethoxy benzene (1.1 g, 8 mmol) and TMEDA (7.5 ml, 50 mmol) in Et$_2$O (80 ml) was added 1.6 M BuLi in hexane (25 ml, 40 mmol). After 3 days at room temperature, bromine (2.5 ml) was added at −78° C., and the mixture was stirred for 1 day at room temperature. The ethereal phase was extracted with water and dried (Na$_2$SO$_4$). The solvent was removed under reduced pressure and the product was purified by column chromatography on silica (hexane:dichloromethane=2:1) to provide the product (800 mg product). $^1$H NMR (400 MHz) (CDCl$_3$) δ 3.93 (s, 6H), 7.20 (s, 2H).

b. Preparation of Compound

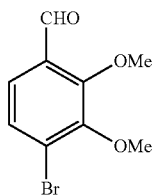 [SMILES: COc1c(Br)ccc(C=O)c1OC]

A solution of 1,4-dibromo-2,3-dimethoxybenzene (1.0 mmol) in THF (1.0 mmol per 3 mL) was cooled to −78° C., and then treated with n-BuLi (1.6 M in hexane, 1.05 equiv). After 10 minutes of stirring at −78° C., the yellow colored reaction mixture was quenched with the addition of DMF and allowed to come to room temperature after which it was poured into water and extracted with ether. The combined organic layers were then washed with water and brine and concentrated. Chromatography on silica using 5% EtOAC in hexane afforded the product. (Yield: 120 mg product from 300 mg starting material). $^1$H NMR (400 MHz) (CDCl$_3$) δ 3.86 (s, 3H), 3.98 (s, 3H), 7.32 (d, J=8.0 Hz, 1H), 7.39 (d, J=8.0 Hz, 1H), 10.23 (s, 1H).

c. Preparation of Compound

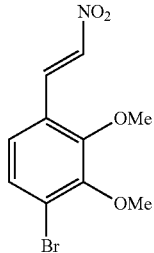 [SMILES: COc1c(Br)ccc(/C=C/[N+](=O)[O-])c1OC]

A mixture of 4-bromo-2,3-dimethoxybenzaldehyde (1.0 mmol), ammonium acetate (1.7 mmol), and 0.26 ml of nitromethane was refluxed in 2 ml glacial acetic acid for 2 h. The reaction mixture was allowed to cool to room temperature. Glacial acetic acid was removed and the crude product was purified by silica gel chromatography using 30% dichloromethane in hexane as solvent (Yield: 90 mg product from 105 mg starting material). $^1$H NMR (400 MHz) (CDCl$_3$) δ 3.83 (s, 3H), 3.92 (s, 3H), 7.04 (d, J=8.0 Hz, 1H), 7.29 (d, J=8.0 Hz, 1H), 7.269 (d, J=12.0 Hz, 1H) 8.03 (d, J=12.0 Hz, 1H).

d. Preparation of Compound

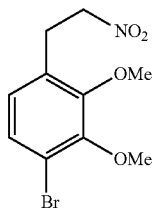

To a stirred suspension of NaBH$_4$ (5 equiv.) in 10 mL 1,4-dioxane/EtOH (2:1) was added a solution of 1-bromo-2,3-dimethoxy-4-(2-nitrovinyl)benzene (1 mmol) in 1,4-dioxane (5 mL) dropwise at 0° C. After this addition, the reaction mixture was stirred for one and half hour. The resulting mixture was diluted with ice-water and quenched with 50% aq AcOH. The resulting suspension was concentrated and then partitioned between NaHCO$_3$ and CH$_2$Cl$_2$. Column using 10% EtOAc in hexane. (Yield: 74 mg product from 86 mg starting material). $^1$H NMR (400 MHz) (CDCl$_3$) δ 3.29 (t, J=4.0 Hz, 2H), 3.89 (s, 3H), 3.95 (s, 3H), 4.62 (t, J=8.0 Hz, 2H), 6.83 (d, J=8.0 Hz, 1H), 7.25 (d, J=8.0 Hz, 1H).

e. Preparation of Compound

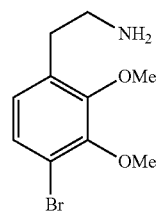 [SMILES: COc1c(Br)ccc(CCN)c1OC]

To a stirred suspension of 1-bromo-2,3-dimethoxy-4-(2-nitroethyl)benzene (70 mg) in 5 mL acetic acid was added Zn Powder (315 mg) portionwise at room temperature. The reaction was complete within 5 minutes. The Zn powder was filtered off, the acetic acid was removed, the residue was diluted with NaHCO$_3$ and extracted with dichloromethane. Chromatography on silica using 10:1:0.1 (dichloromethane:MeOH:triethylamine) gave pure product. (Yield: 50 mg product from 70 mg starting material). $^1$H NMR (400 MHz) (CDCl$_3$) δ 2.73 (t, J=4.0 Hz, 2H), 2.91 (t, J=8.0 Hz, 2H), 3.73 (bs, 2H), 3.79 (s, 3H), 3.82 (s, 3H), 6.75 (d, J=8.0 Hz, 1H), 7.14 (d, J=8.0 Hz, 1H).

f. Preparation of Compound

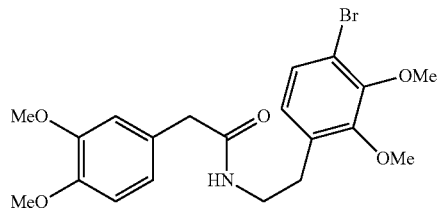 [SMILES: COc1ccc(CC(=O)NCCc2ccc(Br)c(OC)c2OC)cc1OC]

A solution of the acid chloride of 3,4-dimethoxyphenyl acetic acid (4 mmol) in chloroform (6 mL) was added dropwise under nitrogen to a mixture of the substituted phenethylamine (4 mmol), chloroform (6 mL) and 2M sodium carbonate (3 mL) at 0° C. with vigorous stirring. Stirring was continued at 0° C. until the reaction is complete. The reaction mixture was transferred to a separatory funnel using additional amounts of chloroform and water. The organic phase was separated and the aqueous phase extracted with chloroform. The combined chloroform extract was washed with 0.1 N NaOH, 0.1 N HCl and brine. The chloroform extract was dried and evaporated. The crude product was purified by flash column chromatography on silica using 1:1 ethyl acetate:hexane to afford the pure product as a white solid (quantitative yield). $^1$H NMR (400 MHz) (CDCl$_3$) δ 2.73 (t, J=8.0 Hz, 2H), 3.44 (qt, J=4.0 Hz, 2H), 3.49 (s, 2H), 3.83 (s, 3H), 3.87 (s, 3H), 3.90 (s, 3H), 3.92 (s, 3H), 5.62 (bs, 1H), 6.65 (d, J=8.0 Hz, 1H), 6.72 (m, 2H), 6.84 (d, J=8.0 Hz, 1H), 7.17 (d, J=8.0 Hz, 1H).

g. Preparation of Compound

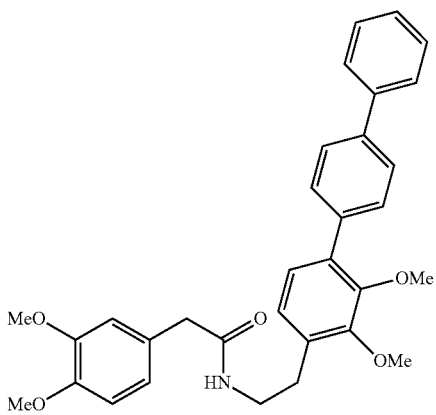 [SMILES: COc1ccc(CC(=O)NCCc2ccc(-c3ccc(-c4ccccc4)cc3)c(OC)c2OC)cc1OC]

To a solution of N-(4-bromo-2,3-dimethoxyphenethyl)-2-(3,4-dimethoxyphenyl)acetamide (0.5 mmol) in 3 mL of dioxane was added biphenyl-4-yl-boronic acid (1.0 mmol), Pd(PPh$_3$)$_2$Cl$_2$ (10 mol %) and Cs$_2$CO$_3$ (1.5 mmol). The mixture was irradiated at 120° C. for 10 minutes using a microwave reactor and cooled to room temperature. The mixture was diluted with ethyl acetate and filtered through a short Celite pad. The solution was concentrated in vacuo and purified by flash column chromatography on silica using ethyl acetate:hexane solvent system (Yield 95%). $^1$H NMR (400 MHz) (CDCl$_3$) δ 2.72 (t, J=8.0 Hz, 2H), 3.43 (m, 4H), 3.55 (s, 3H), 3.77 (s, 3H), 3.78 (s, 3H), 3.79 (s, 3H), 6.67 (s, 2H), 6.73-6.77 (m, 2H) 6.95 (d, J=8.0 Hz, 1H), 7.30 (m, 1H), 7.39 (m, 2H) 7.52 (d, J=8.0 Hz, 2H), 7.59 (m, 4H).

h. Preparation of Compound

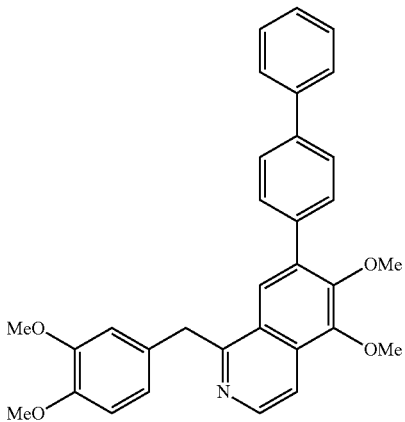 [SMILES: COc1ccc(Cc2nccc3c(OC)c(OC)c(-c4ccc(-c5ccccc5)cc4)cc23)cc1OC]

A mixture of N-[4-(4-biphenyl)-2,3-dimethoxyphenethyl]-2-(3,4-dimethoxyphenyl)acetamide and POCl$_3$ (4 equiv) in dry acetonitrile was heated at reflux for 1 hour. After the reaction is finished, the reaction mixture was diluted with H$_2$O, made basic (10% aqueous NH$_4$OH), and extracted with dichloromethane. The organic solution was washed with H$_2$O, dried with anhydrous sodium sulfate, and concentrated to give the dihydroisoquinoline, which was used for the next step without further purification.

The dihydroisoquinoline is heated at reflux with 10% Pd/C catalyst and tetralin (purged with nitrogen for 30 minutes prior to use) until the reaction is complete as judged by TLC. The catalyst is filtered from the cooled reaction mixture and washed with dichloromethane. Removal of tetralin by vacuum distillation affords the crude product which was then purified by flash column chromatography on silica to give the pure compound (Yield 84%). $^1$H NMR (400 MHz) (CDCl$_3$) δ 3.74 (s, 3H), 3.75 (s, 6H), 4.00 (s, 3H), 4.56 (s, 2H), 6.71 (d, J=8.0 Hz, 1H), 6.79 (d, J=8.0 Hz, 1H), 6.89 (s, 1H), 7.33 (d, J=8.0 Hz, 1H), 7.42 (t, J=8.0 Hz, 2H), 7.52 (d, J=8.0 Hz, 2H), 7.59-7.64 (m, 4H) 7.83 (d, J=4.0 Hz, 1H), 7.96 (s, 1H), 8.40 (d, J=8.0 Hz, 1H).

Example 18

Preparation of Compound

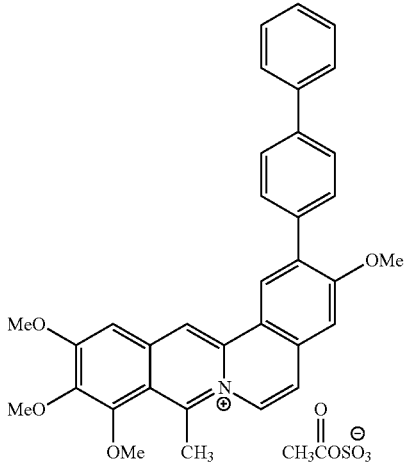

Fuming sulfuric acid (0.2 mL) was added to 0.8 mL freshly distilled acetic anhydride resulting in a vigorous exothermic reaction and the mixture becoming wine-red in color. This mixture was heated at 85-90° C. for 10 minutes. A solution of 7-(biphenyl-4-yl)-1-(3,4,5-trimethoxybenzyl)-6-methoxyisoquinoline (23 mg) in 1 mL of Ac$_2$O was added under nitrogen to the wine red sulfuric acid solution and the resulting mixture was heated at 85-90° C. for 1 h. The reaction mixture was cooled to room temperature and methanol was added. The solution was then chilled and ether was added until a solid precipitated. The solid was then filtered off, washed with small amount of methanol and ether to furnish a yellowish solid in quantitative yield in high purity. $^1$H NMR (400 MHz) (DMSO-d$_6$) δ 3.57 (s, 3H), 3.99 (s, 3H), 4.01 (s, 3H), 4.02 (s, 3H), 4.09 (s, 3H), 7.43 (t, J=8.0 Hz, 1H) 7.53 (d, J=8.0 Hz, 2H), 7.60 (s, 1H), 7.75-7.83 (m, 7H), 7.98 (d, J=8.0 Hz, 1H) 8.83 (s, 1H), 8.92 (d, J=8.0 Hz, 1H), 9.67 (s, 1H).

The intermediate 7-(biphenyl-4-yl)-1-(3,4,5-trimethoxybenzyl)-6-methoxyisoquinoline was prepared as follows.

a. Preparation of Compound

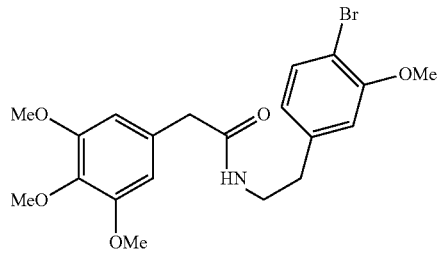 [SMILES: COc1cc(CCNC(=O)Cc2cc(OC)c(OC)c(OC)c2)ccc1Br]

The acid chloride of 2,3,4-trimethoxyphenyl acetic acid (4 mmol) in chloroform (6 mL) was added dropwise under nitrogen to a mixture of 4-bromo-3-methoxyphenethylamine (4 mmol), chloroform (6 mL) and 2M sodium carbonate (3 mL)

at 0° C. with vigorous stirring. Stirring was continued at 0° C. until the reaction was complete. The reaction mixture was transferred to a separatory funnel using additional amounts of chloroform and water. The organic phase was separated and the aqueous phase extracted with chloroform. The combined chloroform extract was washed with 0.1 N NaOH, 0.1 N HCl and brine. The chloroform extract was dried and evaporated. The crude product was purified by flash column chromatography on silica using 1:1 ethyl acetate:hexane to afford the pure product as a white solid (quantitative yield). $^1$H NMR (400 MHz) (CDCl$_3$) δ 2.76 (t, J=4.0 Hz, 2H), 3.50 (m, 4H), 3.87 (s, 6H), 3.89 (s, 6H), 5.48 (bs, 1H), 6.39 (s, 2H), 6.54 (dd, J=8.0 Hz, 4.0 Hz, 1H), 6.69 (s, 1H), 7.41 (d, J=8.0 Hz, 1H).

b. Preparation of Compound

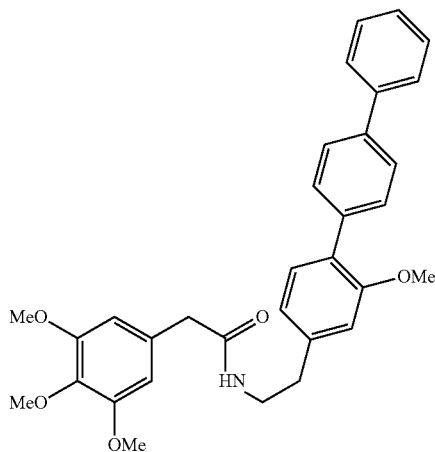 [SMILES: COc1cc(CCNC(=O)Cc2cc(OC)c(OC)c(OC)c2)ccc1-c1ccc(-c2ccccc2)cc1]

To a solution of N-(4-bromo-3-methoxyphenethyl)-2-(2,3,4-trimethoxyphenyl)acetamide (0.5 mmol) in 3 mL of dioxane was added biphenyl-4-yl-boronic acid (1.0 mmol), Pd(PPh$_3$)$_2$Cl$_2$ (10 mol %) and Cs$_2$CO$_3$ (1.5 mmol). The mixture was irradiated at 120° C. for 10 minutes using a microwave reactor and cooled to room temperature. The mixture was diluted with ethyl acetate and filtered through a short Celite pad. The solution was concentrated in vacuo and purified by flash column chromatography on silica using ethyl acetate:hexane solvent system (yields ranging from 85%-95%). $^1$H NMR (400 MHz) (CDCl$_3$) δ 2.74 (d, J=4.0 Hz, 2H), 3.43 (s, 2H), 3.48 (m, 2H), 3.72 (s, 9H), 3.75 (s, 3H), 5.60 (bs, 1H), 6.35 (s, 2H), 6.66 (dd, J=8.0 Hz, 4 Hz, 1H), 6.69 (d, J=4.0 Hz, 1H), 7.18 (d, J=8.0 Hz, 1H) 7.29 (m, 1H), 7.29 (m, 1H), 7.35-7.39 (m, 2H), 7.50-7.57 (m, 6H).

c. Preparation of Compound

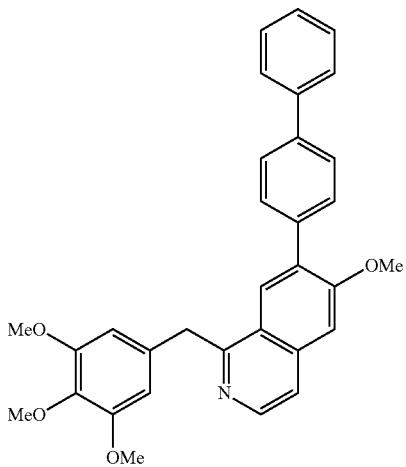 [SMILES: COc1cc2ccnc(Cc3cc(OC)c(OC)c(OC)c3)c2cc1-c1ccc(-c2ccccc2)cc1]

A mixture of N-[4-(4-biphenyl)-3-dimethoxyphenethyl]-2-(3,4,5-trimethoxyphenyl)acetamide and POCl$_3$ (4 equiv) in dry acetonitrile was heated at reflux for 1 hour. After the reaction is finished, the reaction mixture was diluted with H$_2$O, made basic (10% aqueous NH$_4$OH), and extracted with dichloromethane. The organic solution was washed with H$_2$O, dried with anhydrous sodium sulfate, and concentrated to give the dihydroisoquinoline, which was used for the next step without further purification (quantitative yield).

The dihydroisoquinoline is heated at reflux with 10% Pd/C catalyst and tetralin (purged with nitrogen for 30 minutes prior to use) until the reaction is complete as judged by TLC. The catalyst is filtered from the cooled reaction mixture and washed with dichloromethane. Removal of tetralin by vacuum distillation affords the crude product which was then purified by flash column chromatography on silica to give the pure compound (72%). $^1$H NMR (400 MHz) (CDCl$_3$) δ 3.80 (s, 6H), 3.83 (s, 3H), 3.99 (s, 3H), 4.60 (s, 2H), 6.59 (s, 2H), 7.20 (s, 1H) 7.41 (d, J=8.0 Hz, 1H), 7.48-7.55 (m, 3H), 7.60 (d, J=8.0 Hz, 2H) 7.69 (m, 4H), 8.22 (s, 1H), 8.47 (d, J=8.0 Hz, 1H).

Example 19

Preparation of Compound

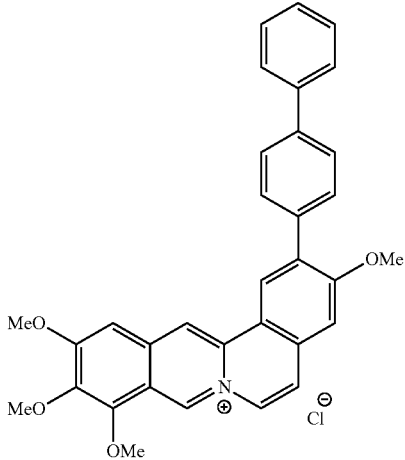 [SMILES: COc1cc2cc[n+]3cc4c(OC)c(OC)c(OC)cc4cc3c2cc1-c1ccc(-c2ccccc2)cc1 ; [Cl-]]

Phosphorus oxychloride (0.2 mL) was added dropwise to chilled (0° C.) DMF (1.0 mL) under nitrogen. The reaction mixture was stirred for 15 minutes at 0° C. A solution of 7-(biphenyl-4-yl)-1-(2,3,4-trimethoxybenzyl)-6-methoxyisoquinoline (25 mg in 1 mL of DMF) was added and allowed to stir at 0° C. for 1 hour. The reaction mixture was subsequently heated at 100° C. for 1 hour. After 1 h at 100° C., the reaction mixture was cooled down and was added to a flask containing some cubes of ice and 0.5 mL of 6N HCl. The solid thus formed was filtered off, washed with a small amount of methanol and ether to afford a yellowish solid in quantitative yield and in high purity. $^1$H NMR (400 MHz) (DMSO-d$_6$) δ 4.01 (s, 3H), 4.06 (s, 3H), 4.14 (s, 3H), 4.24 (s, 3H), 7.44 (t, J=8.0 Hz, 1H), 7.54 (t, J=8.0 Hz, 3H), 7.77-7.85 (m, 7H), 8.03 (s, 1H), 8.94 (s, 1H), 9.03 (s, 1H), 9.82 (s, 1H), 10.17 (s, 1H).

Example 20

Preparation of Compound

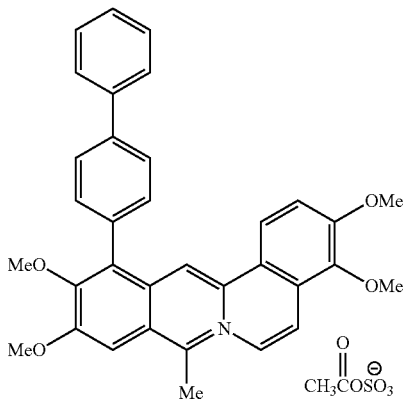

Fuming sulfuric acid (0.2 mL) was added to 0.8 mL freshly distilled acetic anhydride resulting in a vigorous exothermic reaction and the mixture becoming wine-red in color. This mixture was heated at 85-90° C. for 10 minutes. A solution of 1-[2-(biphenyl-4-yl)-3,4-dimethoxybenzyl]-5,6-dimethoxy-isoquinoline (25 mg in 1.0 mL) of Ac$_2$O was added under nitrogen to the wine red sulfuric acid solution and the resulting mixture was heated at 85-90° C. for 1 hour. The reaction mixture was cooled to room temperature and methanol was added. The solution was then chilled and ether was added until a solid precipitated. The solid was then filtered off, washed with small amount of methanol and ether to furnish a yellowish solid in quantitative yield in high purity. $^1$H NMR (400 MHz) (MeOH-d$_4$) δ 3.43 (s, 3H), 3.75 (s, 3H), 3.84 (s, 3H), 3.94 (s, 3H), 4.16 (s, 3H), 7.32-7.36 (m, 1H), 7.42-7.45 (m, 2H), 7.47 (d, J=8.0 Hz, 2H), 7.56 (d, J=8.0 Hz, 2H), 7.68 (d, J=8.0 Hz, 2H), 7.85-7.93 (m, 4H), 8.74 (s, 1H), 8.80 (d, J=8.0 Hz, 1H).

The intermediate 1-[2-(biphenyl-4-yl)-3,4-dimethoxybenzyl]-5,6-dimethoxyisoquinoline was prepared as follows.

a. Preparation of Compound

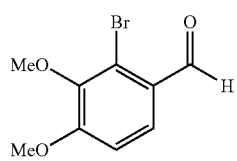 [SMILES: COc1ccc(C=O)c(Br)c1OC]

A suspension of commercially available 2-bromo-3-hydroxy-4-methoxybenzaldehyde (5.63 g) and K$_2$CO$_3$ (10.4 g) in 30 mL DMF was stirred for 10 minutes and then dimethylsulfate (4.4 mL) was added dropwise over a 10 minute period. The reaction mixture was heated over a steam bath for 5 minutes then 2.0 mL water was added. Heating was then continued for an additional 5 minutes. The reaction mixture was then poured into 50 mL of water, and the crystals were collected. Crude product was carried to next step.

b. Preparation of Compound

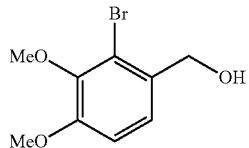

A solution of 2-bromo-3,4-dimethoxybenzaldehyde (4 g) in 30 mL of 95% ethanol was treated with 385 mg of NaBH$_4$ in 95% ethanol while keeping the temperature at 25° C. After 1 hour, acetone (1.5 mL) was added and the filtered solution was concentrated under vacuum. The residue was partitioned between water (60 mL) and dichloromethane (150 mL), and the organic layer was washed with water, dried over sodium sulfate, and concentrated to give a white solid in 86% yield. $^1$H NMR (400 MHz) (CDCl$_3$) δ 3.88 (s, 3H), 3.89 (s, 3H), 4.71 (s, 2H), 6.88 (d, J=8.0 Hz, 1H), 7.18 (d, J=8.0 Hz, 1H).

c. Preparation of Compound

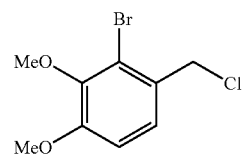

A mixture of (2-bromo-3,4-dimethoxyphenyl)methanol (2.4 g) dissolved in toluene (11 mL) and 12 N HCl (5.6 mL) was stirred over a steam bath for 1 hour. The layers were then separated and toluene layer was washed with water four times. Toluene was then evaporated, redissolved in dichloromethane, and dried over sodium sulfate. The solution was then filtered and concentrated to yield a colorless oil in 90% yeld. $^1$H NMR (400 MHz) (CDCl$_3$) δ 3.89 (s, 3H), 3.91 (s, 3H), 4.72 (s, 2H), 6.89 (d, J=8.0 Hz, 1H), 7.22 (d, J=8.0 Hz, 1H).

d. Preparation of Compound

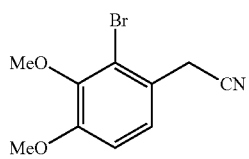 [SMILES: COc1ccc(CC#N)c(Br)c1OC]

The benzyl chloride (1.0 g) and KCN (325 mg) were dissolved in sieve-dried DMSO (5 mL) and stirred for 12 hours at room temperature. Water (50 mL) was then added to the reaction mixture and the reaction mixture was extracted with ethyl acetate. Organic layer was dried with sodium sulfate and concentrated under vacuum. Chromatography on silica using 10% ethyl acetate/hexane yielded the product (830 mg) as a white solid. $^1$H NMR (400 MHz) (CDCl$_3$) δ 3.82 (s, 2H), 3.89 (s, 3H), 3.91 (s, 3H), 6.92 (d, J=8.0 Hz, 1H), 7.25 (d, J=8.0 Hz, 1H).

e. Preparation of Compound

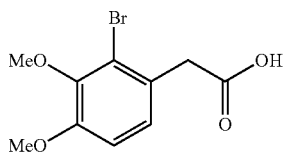 [SMILES: COc1ccc(CC(=O)O)c(Br)c1OC]

2-(2-Bromo-3,4-dimethoxyphenyl)acetonitrile (800 mg) was added to 1 mL of HOAc, 1 mL water, and 1 mL concentrated H₂SO₄ and refluxed for 5 hours. Reaction mixture was then cooled and poured into ice water resulting in a white precipitate. The precipitate was filtered off then dissolved in dichloromethane and washed with water. Organic layer was dried with sodium sulfate then concentrated under vacuum. Purification with chromatography on silica using 5% methanol/dichloromethane yielded the product as a white solid. ¹H NMR (400 MHz) (CDCl₃) δ 3.82 (s, 2H), 3.88 (s, 6H), 6.87 (d, J=8.0 Hz, 1H), 7.03 (d, J=8.0 Hz, 1H), 11.19 (bs).

f. Preparation of Compound

The acid chloride of 2-bromo-3,4-dimethoxyphenyl acetic acid (4 mmol) in chloroform (6 mL) was added dropwise under nitrogen to a mixture of 2,3-dimethoxyphenethylamine (4 mmol), chloroform (6 mL) and 2M sodium carbonate (3 mL) at 0° C. with vigorous stirring. Stirring was continued at 0° C. until the reaction is complete. The reaction mixture was transferred to a separatory funnel using additional amount of chloroform and water. The organic phase was separated and the aqueous phase extracted with chloroform. The combined chloroform extract was washed with 0.1 N NaOH, 0.1 N HCl and brine. The chloroform extract was dried and evaporated. The crude product was purified by flash column chromatography on silica using 1:1 ethyl acetate:hexane to afford the pure product as white solid (quantitative yield). ¹H NMR (400 MHz) (CDCl₃) δ 2.70 (m, 2H), 3.45 (m, 2H), 3.62 (s, 2H), 3.84-3.87 (m, 12H), 5.55 (m, 1H), 6.59-6.64 (m, 2H), 6.73 (d, J=8.0 Hz, 1H), 6.82 (d, J=8.0 Hz, 1H), 6.98 (d, J=8.0 Hz, 1H).

g. Preparation of Compound

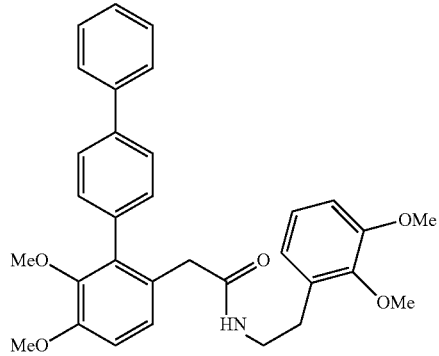 [SMILES: COc1cccc(CCNC(=O)Cc2ccc(OC)c(OC)c2-c2ccc(-c3ccccc3)cc2)c1OC]

To a solution of N-(2,3-dimethoxyphenethyl)-2-(2-bromo-3,4-dimethoxyphenyl)acetamide (0.5 mmol) in 3 mL of dioxane was added biphenyl-4-yl-boronic acid (1.0 mmol), Pd(PPh₃)₂Cl₂ (10 mol %) and Cs₂CO₃ (1.5 mmol). The mixture was irradiated at 120° C. for 10 minutes using a microwave reactor and cooled to room temperature. The mixture was diluted with ethyl acetate and filtered through a short Celite pad. The solution was concentrated in vacuo and purified by flash column chromatography on silica using ethyl acetate:hexane solvent system (93% yield). ¹H NMR (400 MHz) (CDCl₃) δ 2.68 (t, J=8.0 Hz, 2H), 3.32 (s, 2H), 3.40 (qt, J=8.0 Hz, 2H), 3.57 (s, 3H), 3.83 (s, 3H), 3.85 (s, 3H), 3.94 (s, 3H), 4.58 (dd, J=8.0 Hz, 4.0 Hz, 1H), 6.64 (d, J=4.0 Hz, 1H), 6.74 (d, J=8.0 Hz, 1H) 6.93 (d, J=8.0 Hz, 1H), 7.04 (d, J=8.0 Hz, 1H), 7.19 (d, J=8.0 Hz, 2H), 7.40 (m, 1H), 7.48 (t, J=8.0 Hz, 2H), 7.63 (d, J=8.0 Hz, 2H), 7.66 (d, J=8.0 Hz, 2H).

h. Preparation of Compound

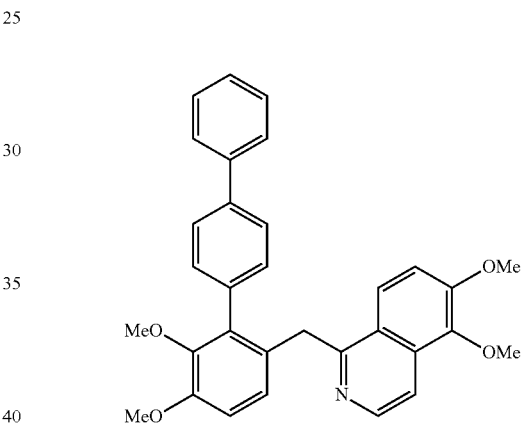

A mixture of N-(2,3-dimethoxyphenethyl)-2-[(2-(4-biphenyl)-3,4-dimethoxyphenyl)]acetamide and POCl₃ (4 equiv) in dry acetonitrile was heated at reflux for 1 hour. After the reaction was finished, the reaction mixture was diluted with H₂O, made basic (10% aqueous NH₄OH), and extracted with dichloromethane. The organic solution was washed with H₂O, dried with anhydrous sodium sulfate, and concentrated to give the dihydroisoquinoline, which was used for the next step without further purification (quantitative yield).

The dihydroisoquinoline is heated at reflux with 10% Pd/C catalyst and tetralin (purged with nitrogen for 30 minutes prior to use) until the reaction is complete as judged by TLC. The catalyst is filtered from the cooled reaction mixture and washed with dichloromethane. Removal of tetralin by vacuum distillation affords the crude product which was then purified by flash column chromatography on silica to give the desired compound (71% yield). ¹H NMR (400 MHz) (CDCl₃) δ 3.82 (s, 3H), 3.87 (s, 3H), 3.99 (s, 3H), 4.41 (s, 2H), 6.80 (d, J=8.0 Hz, 2H), 6.90 (s, 1H), 4.41 (s, 2H), 6.80 (d, J=8.0 Hz, 2H), 6.90 (s, 1H), 7.02 (s, 1H), 7.37-7.42 (m, 4H), 7.47 (m, 2H), 7.61-7.67 (m, 4H), 8.33 (d, J=8.0 Hz, 1H).

Example 21

Preparation of Compound

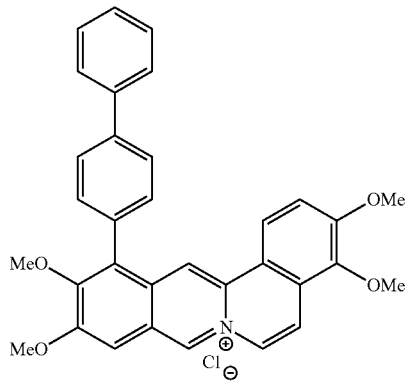 [SMILES: COc1cc2c[n+]3ccc4c(OC)c(OC)ccc4c3cc2c(-c2ccc(-c3ccccc3)cc2)c1OC ; [Cl-]]

Phosphorus oxychloride (0.2 mL) was added dropwise to chilled (0° C.) DMF (1.0 mL) under nitrogen. The reaction mixture was stirred for 15 minutes at 0° C. A solution of 1-[(2-biphenyl-4-yl)3,4-dimethoxybenzyl]-5,6-dimethoxy-isoquinoline (23 mg in 1 mL of DMF) was added and allowed to stir at 0° C. for 1 hour. The reaction mixture was subsequently heated at 100° C. for 1 hour. After 1 h at 100° C., the reaction mixture was cooled down and was added to a flask containing some cubes of ice and 0.5 mL of 6N HCl. The solid thus formed was filtered off, washed with a small amount of methanol and ether to afford a yellowish solid in quantitative yield in high purity. $^1$H NMR (400 MHz) (MeOH-$d_4$) δ 3.76 (s, 3H), 3.81 (s, 3H), 3.90 (s, 3H), 4.10 (s, 3H), 7.35 (m, 1H), 7.44 (m, 4H), 7.53 (d, J=8.0 Hz, 2H), 7.66 (d, J=8.0 Hz, 2H), 7.73 (s, 1H), 7.85 (m, 3H), 8.61 (d, J=8.0 Hz, 1H), 8.65 (s, 1H), 9.93 (s, 1H).

Example 22

Preparation of Compound

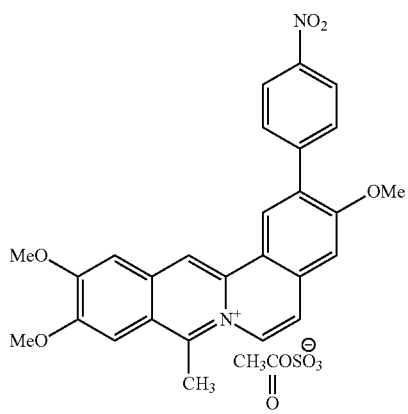

Fuming sulfuric acid (0.2 mL) was added to 0.8 mL freshly distilled acetic anhydride resulting in a vigorous exothermic reaction and the mixture becoming wine-red in color. This mixture was heated at 85-90° C. for 10 minutes. A solution of 7-(4-nitrophenyl)-6-methoxy-1-(3,4-dimethoxybenzyl) iso- quinoline (22 mg in 1.0 mL) of Ac$_2$O was added under nitrogen to the wine red sulfuric acid solution and the resulting mixture was heated at 85-90° C. for 1 h. The reaction mixture was cooled to room temperature and methanol was added. The solution was then chilled and ether was added until a solid precipitated. The solid was then filtered off, washed with small amount of methanol and ether to furnish a yellow solid in quantitative yield in high purity as a yellow solid, 17 mg, 44% yield. $^1$H NMR (DMSO) δ 10.10 (s, 1H), 9.75 (s, 1H), 8.96 (d, 2H, J=8 Hz), 8.85 (s, 1H), 8.06 (d, 1H, J=8 Hz), 7.84 (s, 1H), 7.78 (d, 1H, J=12 Hz), 7.74 (d, 1H, J=8 Hz), 7.67 (d, 1H, J=8 Hz), 4.12 (s, 3H), 4.08 (s, 3H), 4.02 (s, 3H), 2.11 (s, 3H).

The intermediate 7-(4-nitrophenyl)-6-methoxy-1-(3,4-dimethoxybenzyl-5,6-dimethoxyisoquinoline was prepared as follows.

a. Preparation of Compound

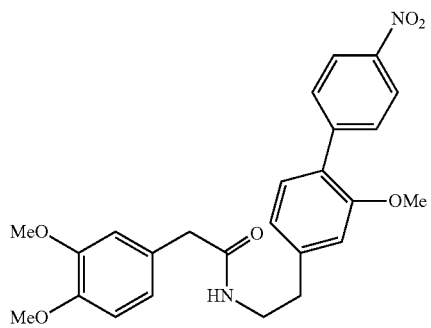 [SMILES: COc1ccc(CC(=O)NCCc2ccc(-c3ccc([N+](=O)[O-])cc3)c(OC)c2)cc1OC]

To a degassed mixture of N-(4-bromo-3-methoxyphen-ethyl)-2-(3,4-dimethoxyphenyl)acetamide (200 mg, 0.489 mmol) and 4,4,5,5-tetramethyl-2-(4-nitrophenyl)-1,3,2-dioxaborolane (180 mg, 0.73 mmol) in DMF (5 ml) was added K$_3$PO$_4$ (310 mg, 1.5 mmol), followed by addition of tetrakis(triphenylphosphine)-palladium (18 mg, 0.016 mmol). The resulting mixture was stirred at 85° C. under nitrogen overnight. The reaction mixture was diluted with EtOAc to 60 mL and washed with aq NaHCO$_3$ solution twice and 10% lithium chloride solution once. The EtOAc solution was dried over Na$_2$SO$_4$ and concentrated under reduced pressure and the reaction mixture was purified on silica gel eluting with 10-90% EtOAc/hexane to give the title compound as a solid (180 mg, 82%). $^1$H NMR (CDCl$_3$) δ 8.18 (d, 2H, J=8 Hz), 7.60 (d, 2H, J=8 Hz), 7.12 (d, 1H, J=8 Hz), 6.70 (d, 1H, J=8 Hz), 6.67-6.64 (m, 4H), 5.43-5.38 (m, 1H), 3.76 (s, 3H), 3.75 (s, 3H), 3.71 (s, 3H), 3.44 (t, 2H, J=8 Hz), 3.43 (s, 2H), 2.73 (t, 2H, J=8 Hz).

b. Preparation of Compound

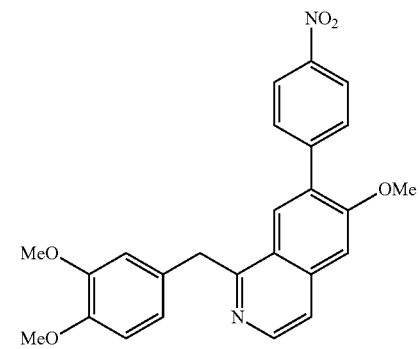

A mixture of N-[3-methoxy-(4-nitrophenyl)phenethyl]-2-(3,4-dimethoxyphenyl)acetamide (0.18 g, 0.40 mmol) and POCl$_3$ (0.15 ml, 1.6 mmol; 4 equiv) in dry acetonitrile was heated at reflux for 1 hour. After the reaction was finished, the reaction mixture was diluted with H$_2$O, made basic (10% aqueous NH$_4$OH), and extracted with dichloromethane. The organic solution was washed with H$_2$O, dried with anhydrous sodium sulfate, and concentrated to give the dihydroisoquinoline, which was used for the next step without further purification (quantitative yield).

The dihydroisoquinoline is heated at reflux with 10% Pd/C catalyst and tetralin (purged with nitrogen for 30 minutes prior to use) until the reaction is complete as judged by TLC. The catalyst is filtered from the cooled reaction mixture and washed with dichloromethane. Removal of tetralin by vacuum distillation affords the crude product which was then purified by flash column chromatography on silica to give 48 mg of the pure compound in 28% yield as an off-white solid. $^1$H NMR (CDCl$_3$) δ 8.34 (d, 1H, J=8 Hz), 7.98 (s, 1H), 7.37 (d, 2H, J=8 Hz), 7.24 (d, 1H, J=8 Hz), 7.03 (s, 1H), 6.81 (d, 1H, J=4 Hz), 6.76-6.71 (m, 1H), 6.68 (s, 1H), 6.65 (s, 1H), 4.43 (s, 2H), 3.86 (s, 3H), 3.74 (s, 3H), 3.72 (s, 3H).

Example 23

Preparation of Compound

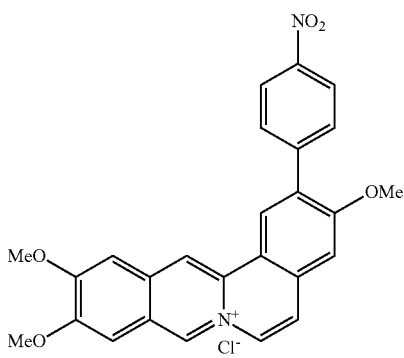 [SMILES: COc1cc2cc3c4cc(-c5ccc([N+](=O)[O-])cc5)c(OC)cc4cc[n+]3cc2cc1OC ; [Cl-]]

Phosphorus oxychloride (0.2 mL) was added dropwise to chilled (0° C.) DMF (1.0 mL) under nitrogen. The reaction mixture was stirred for 15 minutes at 0° C. A solution of 1-(3,4-dimethoxybenzyl)-6-methoxy-7-(p-nitrophenyl)isoquinoline (20 mg, 0.40 mmol) in 1 mL of DMF was added and allowed to stir at 0° C. for 1 hour. The reaction mixture was subsequently heated at 100° C. for 1 hour. After 1 h at 100° C., the reaction mixture was cooled down and was added to a flask containing some cubes of ice and 0.5 mL of 6N HCl. The solid thus formed was filtered off, washed with a small amount of methanol and ether to afford 13 mg of a yellow solid in 60% yield in high purity. $^1$H NMR (DMSO) δ 10.09 (s, 1H), 9.88 (s, 1H), 8.98 (s, 1H), 8.91 (d, 2H, J 8 Hz), 8.12 (d, 1H, J=8 Hz), 7.90-7.84 (m, 4H), 7.77 (s, 1H), 7.71 (m, 2H), 4.17 (s, 3H), 4.13 (s, 3H), 4.09 (s, 3H).

Example 24

Preparation of Compound

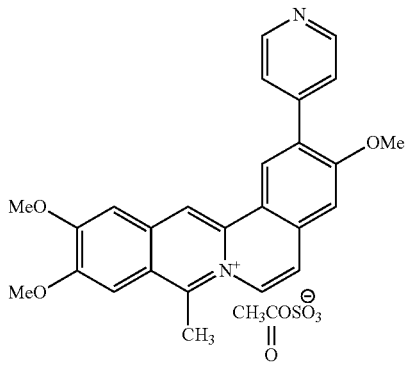

Fuming sulfuric acid (0.2 mL) was added to 0.8 mL freshly distilled acetic anhydride resulting in a vigorous exothermic reaction and the mixture becoming wine-red in color. This mixture was heated at 85-90° C. for 10 minutes. A solution of 1-(3,4-dimethoxybenzyl)-6-methoxy-7-(4-pyridyl)isoquinoline (28 mg, 0.065 mol) in 1 mL of Ac$_2$O was added under nitrogen to the wine red sulfuric acid solution and the resulting mixture was heated at 85-90° C. for 1 h. The reaction mixture was cooled to room temperature and methanol was added. The solution was then chilled and ether was added until a solid precipitated. The solid was then filtered off, washed with small amount of methanol and ether to furnish 17 mg of a yellow solid in 60% yield. $^1$H NMR (DMSO) δ 9.78 (s, 1H), 9.08 (s, 1H), 9.03 (d, 1H, J=8 Hz), 8.92 (d, 2H, J=8 Hz), 8.13 (d, 2H, J=8 Hz), 8.07 (d, 1H, J=8 Hz), 7.93 (s, 1H), 7.89 (s, 1H), 7.73 (s, 1H), 4.13 (s, 3H), 4.11 (s, 3H), 4.07 (s, 3H), 3.45 (s, 3H).

The intermediate 1-(3,4-dimethoxybenzyl)-6-methoxy-7-(4-pyridyl)isoquinoline was prepared as follows.

a. Preparation of Compound

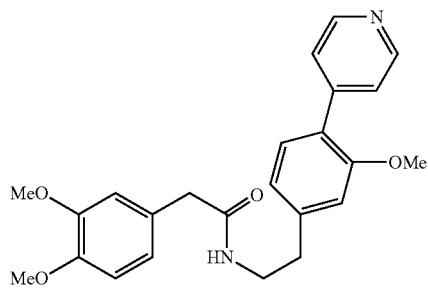 [SMILES: COc1ccc(CC(=O)NCCc2ccc(-c3ccncc3)c(OC)c2)cc1OC]

To a mixture of N-(4-bromo-3-methoxyphenethyl)-2-(3,4-dimethoxyphenyl)acetamide (200 mg, 0.489 mmol), 4-pyridyl boronic acid (90 mg, 0.732 mmol) in 10% H$_2$O/DMF (3 ml) was added Na$_2$CO$_3$ (100 mg, 0.94 mmol), followed by addition of tetrakis(triphenylphosphine)palladium (22 mg, 0.019 mmol). The resulting mixture was stirred at 80° C. under nitrogen overnight. The reaction mixture was diluted with EtOAc to 60 mL and washed with aq NaHCO$_3$ solution and 10% lithium chloride solution. The EtOAc solution was dried over Na$_2$SO$_4$ and concentrated under reduced pressure and the reaction mixture was purified on silica gel eluting with 10-90% EtOAc/hexane to give the title compound as a solid (120 mg, 60%). $^1$H NMR (CDCl$_3$), δ, 8.54 (d, 2H, J=4 Hz), 7.37 (d, 2H, J=8 Hz), 7.12 (d, 1H, J=8 Hz), 6.72 (d, 1H, J=8 Hz), 6.69-6.54 (m, 4H), 5.39 (bs, 1H), 3.76 (s, 3H), 3.75 (s, 3H), 3.71 (s, 3H), 3.45 (t, 2H, J=8 Hz), 3.43 (s, 2H), 2.73 (t, 2H, J=8 Hz).

b. Preparation of Compound

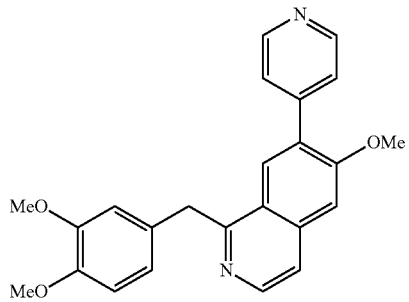 [SMILES: COc1ccc(Cc2nccc3cc(OC)c(-c4ccncc4)cc23)cc1OC]

A mixture of N-(4-(4-pyridyl)-3-methoxyphenethyl)-2-(3,4-dimethoxyphenyl)acetamide (0.100 g, 0.25 mol) and POCl$_3$ (0.09 ml, 0.97 mmol; 4 equiv) in dry acetonitrile was heated at reflux for 1 hour. After the reaction is finished, the reaction mixture was diluted with H$_2$O, made basic (10% aqueous NH$_4$OH), and extracted with dichloromethane. The organic solution was washed with H$_2$O, dried with anhydrous sodium sulfate, and concentrated to give the dihydroisoquinoline, which was used for the next step without further purification (quantitative yield).

The dihydroisoquinoline is heated at reflux with 10% Pd/C catalyst and tetralin (purged with nitrogen for 30 minutes prior to use) until the reaction is complete as judged by TLC. The catalyst is filtered from the cooled reaction mixture and washed with dichloromethane. Removal of tetralin by vacuum distillation affords the crude product which was then purified by flash column chromatography on silica to give 60 mg, 60% yield of the pure compound as a white solid. $^1$H NMR (CDCl$_3$) δ 8.64 (d, 2H, J=8 Hz), 8.48 (d, 1H, J=8 Hz), 8.06 (s, 1H), 7.42 (d, 1H, J=8 Hz), 7.34 (d, 2H, J=8 Hz), 7.09 (s, 1H), 6.79 (s, 1H), 6.71-6.68 (m, 2H), 4.49 (s, 2H), 3.88 (s, 3H), 3.75 (s, 3H), 3.70 (s, 3H).

Example 25

Preparation of Compound

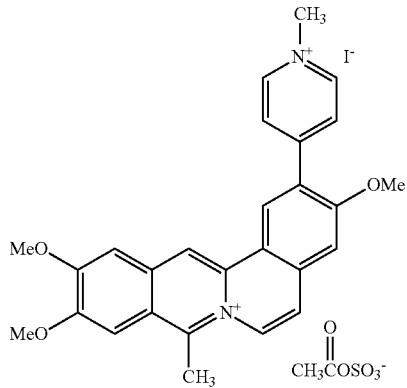

To a stirred mixture of Example 28 (8 mg, 0.015 mmol) in DMF (5 mL) was added iodomethane (1 mL) under nitrogen at room temperature. The reaction mixture was stirred at r.t overnight. The cloudy reaction mixture was added with Et$_2$O and a solid was collected and washed with Et$_2$O to give a yellowish brown solid as the desired product (7 mg, 70%). $^1$H NMR (DMSO) δ 9.82 (s, 1H), 9.21 (s, 1H), 9.15 (d, 2H, J=8 Hz), 9.08 (d, 1H, J=8 Hz), 8.59 (d, 2H, J=8 Hz), 8.09 (d, 1H, J=8 Hz), 8.01 (s, 1H), 7.96-7.93 (m, 1H), 7.73 (s, 1H), 4.45 (s, 3H), 4.14 (s, 6H), 4.11 (s, 3H), 3.47 (s, 3H).

Example 26

Preparation of Compound

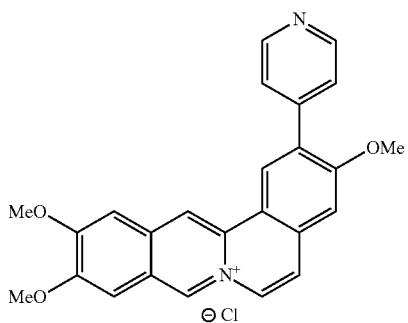 [SMILES: COc1cc2cc3c4cc(-c5ccncc5)c(OC)cc4cc[n+]3cc2cc1OC ; [Cl-]]

Phosphorus oxychloride (0.2 mL) was added dropwise to chilled (0° C.) DMF (1.0 mL) under nitrogen. The reaction mixture was stirred for 15 minutes at 0° C. A solution of 1-(3,4-dimethoxybenzyl)-6-methoxy-7-(4-pyridyl)isoquinoline (20 mg, 0.052 mmol) in 1 mL of DMF was added and allowed to stir at 0° C. for 1 hour. The reaction mixture was subsequently heated at 100° C. for 1 hour. After 1 h at 100° C., the reaction mixture was cooled down and was added to a flask containing some cubes of ice and 0.5 mL of 6N HCl. The solid thus formed was filtered off, washed with a small amount of methanol and ether to afford 14 mg of a yellow solid in 64% yield. $^1$H NMR (DMSO) δ 10.00 (s, 1H), 9.82 (s, 1H), 9.01 (s, 1H), 8.87 (d, 1H, J 4 Hz), 8.83 (d, 2H, J=4 Hz), 8.06 (d, 1H, J=8 Hz), 7.90 (m, 3H), 7.80 (s, 1H), 7.69 (s, 1H), 4.13 (s, 3H), 4.08 (s, 3H), 4.07 (s, 3H).

Example 27

Preparation of Compound

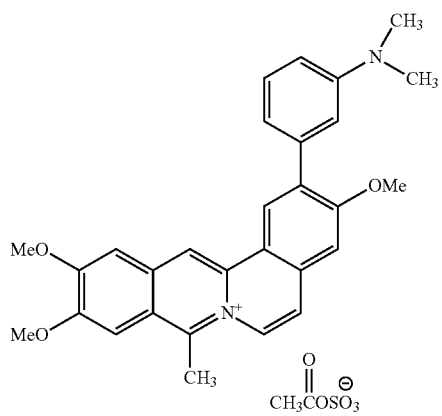

Fuming sulfuric acid (0.2 mL) was added to 0.8 mL freshly distilled acetic anhydride resulting in a vigorous exothermic reaction and the mixture becoming wine-red in color. This mixture was heated at 85-90° C. for 10 minutes. A solution of 1-(3,4-dimethoxybenzyl)-6-methoxy-7-(3-(N,N-dimethylaminophenyl))isoquinoline (33 mg, 0.07 mol) in 1 mL of Ac₂O was added under nitrogen to the wine red sulfuric acid solution and the resulting mixture was heated at 85-90° C. for 1 h. The reaction mixture was cooled to room temperature and methanol was added. The solution was then chilled and ether was added until a solid precipitated. The solid was then filtered off, washed with small amount of methanol and ether to furnish 23 mg of a yellow solid (55% yield). $^1$H NMR (DMSO) δ 9.79 (s, 1H), 8.98 (d, 1H, J=8 Hz), 8.90 (s, 1H), 8.07 (d, 2H, J=8 Hz), 7.86 (s, 1H), 7.83 (s, 1H), 7.93 (s, 1H), 7.78 (s, 1H), 7.41 (m, 1H), 7.30-7.01 (m, 3H), 4.12 (s, 3H), 4.10 (s, 3H), 4.02 (s, 3H), 3.57 (s, 3H), 3.45 (s, 3H), 3.44 (s, 3H).

The intermediate 1-(3,4-dimethoxybenzyl)-6-methoxy-7-(3-(N,N-dimethylaminophenyl))isoquinoline was prepared as follows.

a. Preparation of Compound

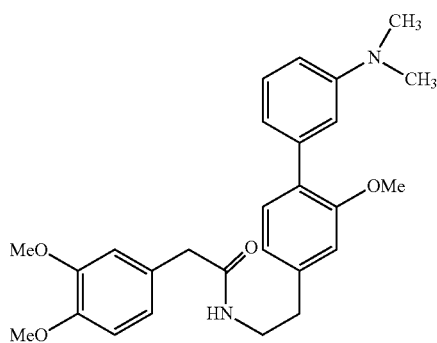 [SMILES: COc1ccc(CC(=O)NCCc2ccc(-c3cccc(N(C)C)c3)c(OC)c2)cc1OC]

To a mixture of N-(4-bromo-3-methoxyphenethyl)-2-(3,4-dimethoxyphenyl)acetamide (200 mg, 0.489 mmol), 3-dimethylaminophenyl boronic acid (100 mg, 0.61 mmol) in H₂O/dioxane (0.2/8 ml) was added K₂CO₃ (200 mg, 1.45 mmol), followed by addition of [1,1'-bis(diphenylphosphino)-ferrocene]dichloropalladium.CH₂Cl₂ (26 mg, 0.032 mmol). The resulting mixture was stirred at 86° C. under nitrogen overnight. The reaction mixture was dried over Na₂SO₄, filtered and concentrated under reduced pressure. The reaction mixture was purified on silica gel eluting with 10-90% EtOAc/hexane to give the title compound as a solid (140 mg, 64%). $^1$H NMR (CDCl₃) δ 8.54 (d, 2H, J=4 Hz), 7.37 (d, 2H, J=8 Hz), 7.12 (d, 1H, J=8 Hz), 6.72 (d, 1H, J=8 Hz), 6.69-6.54 (m, 4H), 5.42 (bs, 1H), 3.75 (ds, 6H), 3.68 (s, 3H), 3.45 (t, 2H, J=8 Hz), 3.42 (s, 2H), 2.90 (s, 6H), 2.73 (t, 2H, J=8 Hz).

b. Preparation of Compound

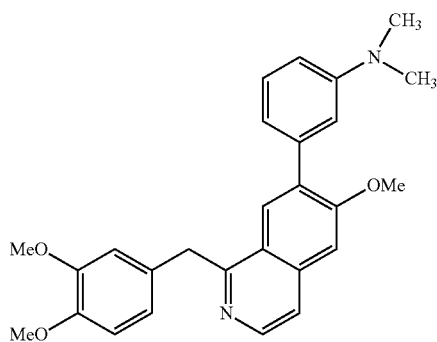 [SMILES: COc1ccc(Cc2nccc3cc(OC)c(-c4cccc(N(C)C)c4)cc23)cc1OC]

A mixture of N-[4-(3-N,N-dimethylaminophenyl)]-3-methoxyphenethyl)-2-(3,4-dimethoxyphenyl)acetamide (0.12 ml, 1.29 mmol) and POCl₃ (4 equiv) in dry acetonitrile was heated at reflux for 1 hour. After the reaction is finished, the reaction mixture was diluted with H₂O, made basic (10% aqueous NH₄OH), and extracted with dichloromethane. The organic solution was washed with H₂O, dried with anhydrous sodium sulfate, and concentrated to give the dihydroisoquinoline, which was used for the next step without further purification.

The dihydroisoquinoline is heated at reflux with 10% Pd/C catalyst and tetralin (purged with nitrogen for 30 minutes prior to use) until the reaction is complete as judged by TLC. The catalyst is filtered from the cooled reaction mixture and washed with dichloromethane. Removal of tetralin by vacuum distillation affords the crude product which was then purified by flash column chromatography on silica to give 60 mg, 60% yield of the pure compound as a white solid. $^1$H NMR (CDCl₃) δ 8.34 (d, 1H, J=4 Hz), 8.05 (s, 1H), 7.40 (d, 1H, J=4 Hz), 7.24 (m, 1H), 7.06 (s, 1H), 6.74 (m, 2H), 6.71-6.60 (m, 4H), 4.47 (s, 2H), 3.86 (s, 3H), 3.73 (s, 3H), 3.70 (s, 3H), 2.90 (s, 6H).

Example 28

Preparation of Compound

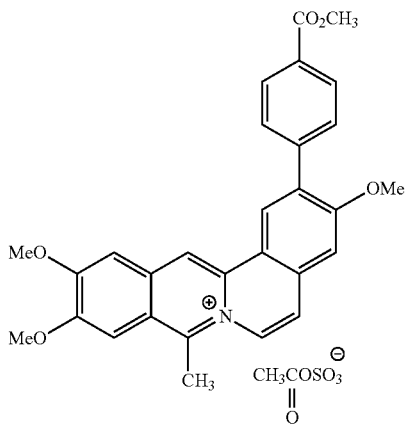

Fuming sulfuric acid (0.2 mL) was added to 0.8 mL freshly distilled acetic anhydride resulting in a vigorous exothermic reaction and the mixture becoming wine-red in color. This mixture was heated at 85-90° C. for 10 minutes. A solution of 1-(3,4-dimethoxybenzyl)-6-methoxy-7-[4-(methoxycarbonyl)phenyl]isoquinoline (81 mg, 0.18 mmol) in 1 mL of Ac₂O was added under nitrogen to the wine red sulfuric acid solution and the resulting mixture was heated at 85-90° C. for 1 h. The reaction mixture was cooled to room temperature and methanol was added. The solution was then chilled and ether was added until a solid precipitated. The solid was then filtered off, washed with small amount of methanol and ether to furnish 25 mg of a yellow solid, 73% yield. $^1$H NMR (DMSO) δ 9.81 (s, 1H), 9.01 (d, 1H, J=8 Hz), 8.97 (s, 1H), 8.14 (d, 2H, J=8 Hz), 8.09 (d, 1H, J=8 Hz), 7.90-7.87 (m, 4H), 7.74 (s, 1H), 4.13 (s, 3H), 4.10 (s, 3H), 4.02 (s, 3H), 3.93 (s, 3H), 3.45 (s, 3H).

The intermediate 1-(3,4-dimethoxybenzyl)-6-methoxy-7-[4-(methoxycarbonyl)phenyl]-isoquinoline was prepared as follows.

a. Preparation of Compound

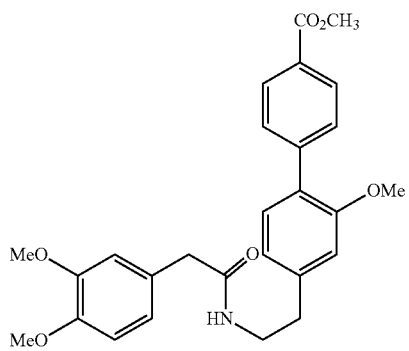 [SMILES: COC(=O)c1ccc(-c2ccc(CCNC(=O)Cc3ccc(OC)c(OC)c3)cc2OC)cc1]

To a mixture of N-(4-bromo-3-methoxyphenethyl)-2-(3,4-dimethoxyphenyl)acetamide (500 mg, 1.22 mmol), 4-methoxycarbonylphenyl boronic acid (250 mg, 1.39 mmol) in H$_2$O/dioxane (0.5/15 ml) was added K$_2$CO$_3$ (500 mg, 3.62 mmol), followed by addition of [1,1'-bis(diphenylphosphino)-ferrocene]dichloropalladium.CH$_2$Cl$_2$ (50 mg, 0.06 mmol). The resulting mixture was stirred at 86° C. under nitrogen overnight. The reaction mixture was dried over Na$_2$SO$_4$, filtered and concentrated under reduced pressure. The reaction mixture was purified on silica gel eluting with 10-90% EtOAc/hexane to give the title compound as a solid (430 mg, 76%). $^1$H NMR (CDCl$_3$) δ 7.99 (d, 2H, J=4 Hz), 7.51 (d, 2H, J=8 Hz), 7.12 (d, 1H, J=8 Hz), 6.70 (d, 1H, J=8 Hz), 6.66-6.62 (m, 4H), 5.40 (bs, 1H), 3.86 (s, 3H), 3.74 (s, 6H), 3.69 (s, 3H), 3.44 (t, 2H, J=8 Hz), 3.45 (s, 2H), 2.73 (t, 2H, J=8 Hz).

b. Preparation of Compound

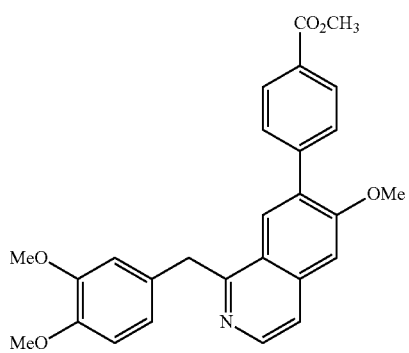 [SMILES: COC(=O)c1ccc(-c2cc3c(Cc4ccc(OC)c(OC)c4)nccc3cc2OC)cc1]

A mixture of N-[4-(4-methoxycarbonyl)phenyl]-3-methoxyphenethyl)-2-(3,4-dimethoxyphenyl)acetamide (0.20 g, 0.43 mmol) and POCl$_3$ (0.16 ml, 1.73 mmol; 4 equiv) in dry acetonitrile was heated at reflux for 1 hour. After the reaction is finished, the reaction mixture was diluted with H$_2$O, made basic (10% aqueous NH$_4$OH), and extracted with dichloromethane. The organic solution was washed with H$_2$O, dried with anhydrous sodium sulfate, and concentrated to give the dihydroisoquinoline, which was used for the next step without further purification.

The dihydroisoquinoline is heated at reflux with 10% Pd/C catalyst and tetralin (purged with nitrogen for 30 minutes prior to use) until the reaction is complete as judged by TLC. The catalyst is filtered from the cooled reaction mixture and washed with dichloromethane. Removal of tetralin by vacuum distillation affords the crude product which was then purified by flash column chromatography on silica to give 0.16 g, 83% yield of the pure compound as a white solid. $^1$H NMR (CDCl$_3$) δ 8.37 (d, 1H, J=4 Hz), 8.04 (s, 1H), 8.03 (d, 1H, J=8 Hz), 7.48 (d, 2H, J=8 Hz), 7.42 (d, 1H, J=4 Hz), 7.08 (s, 1H), 6.79 (d, 1H, J=4 Hz), 6.74-6.67 (m, 2H), 4.49 (s, 2H), 3.89 (s, 3H), 3.87 (s, 3H), 3.75 (s, 3H), 3.71 (s, 3H).

Example 29

Preparation of Compound

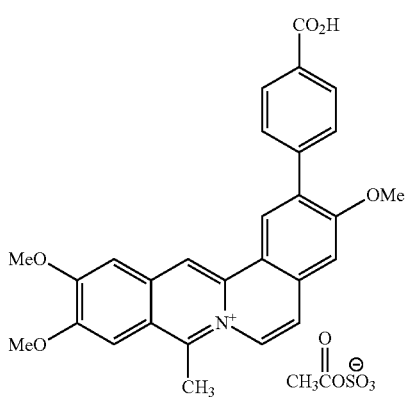

Fuming sulfuric acid (0.2 mL) was added to 0.8 mL freshly distilled acetic anhydride resulting in a vigorous exothermic reaction and the mixture becoming wine-red in color. This mixture was heated at 85-90° C. for 10 minutes. A solution of 1-(3,4-dimethoxybenzyl)-6-methoxy-7-(4-carboxyphenyl) isoquinoline (25 mg) in 1 mL of Ac$_2$O was added under nitrogen to the wine red sulfuric acid solution and the resulting mixture was heated at 85-90° C. for 1 h. The reaction mixture was cooled to room temperature and methanol was added. The solution was then chilled and ether was added until a solid precipitated. The solid was then filtered off, washed with small amount of methanol and ether to furnish 25 mg of a yellow solid, 72% yield. $^1$H NMR (DMSO-d$_6$) 9.56 (s, 1H), 8.78 (d, 1H, J=8 Hz), 8.72 (s, 1H), 7.90 (d, 2H, J=8 Hz), 7.85 (d, 2H, J=8 Hz), 7.65-7.62 (m, 4H), 7.50 (s, 1H), 3.90 (s, 3H), 3.87 (s, 3H), 3.81 (s, 3H), 3.22 (s, 3H).

a. Preparation of Compound

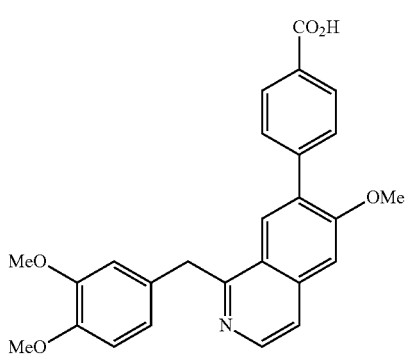 [SMILES: COc1ccc(Cc2nccc3cc(OC)c(-c4ccc(C(=O)O)cc4)cc23)cc1OC]

A mixture of methyl 4-(1-(3,4-dimethoxybenzyl)-6-methoxyisoquinolin-7-yl)benzoate (81 mg, 0.18 mmol) and 1N NaOH (0.35 mL, 0.35 mmol) in MeOH (6 mL) was heated at 70° C. for 2 hours. All of the methanol was removed and the residue was acidified with aq HCl. A white solid was collected and washed with water and dried to give the desired product (31 mg). The filtrate was extracted with EtOAc. The EtOAc was dried over Na$_2$SO$_4$ and concentrated to a white solid as the desired product (40 mg, total 71 mg, 92%). $^1$H NMR (DMSO) δ 8.39 (d, 2H, J=4 Hz), 8.26 (s, 1H), 8.02 (d, 2H, J=8 Hz), 7.67 (d, 1H, J=4 Hz), 7.64 (d, 2H, J=8 Hz), 7.51 (s, 1H), 7.01 (d, 1H, J=4 Hz), 6.82 (d, 1H, J=8 Hz), 6.72 (d, 1H, J=8 Hz), 4.56 (s, 2H), 3.93 (s, 3H), 3.67 (s, 6H).

Example 30

Preparation of Compound

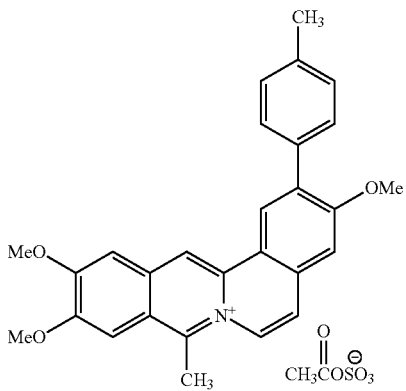

Fuming sulfuric acid (0.2 mL) was added to 0.8 mL freshly distilled acetic anhydride resulting in a vigorous exothermic reaction and the mixture becoming wine-red in color. This mixture was heated at 85-90° C. for 10 minutes. A solution of 1-(3,4-dimethoxybenzyl)-6-methoxy-7-(4-methylphenyl) isoquinoline (20 mg) in 1 mL of Ac$_2$O was added under nitrogen to the wine red sulfuric acid solution and the resulting mixture was heated at 85-90° C. for 1 hour. The reaction mixture was cooled to room temperature and methanol was added. The solution was then chilled and ether was added until a solid precipitated. The solid was then filtered off, washed with small amount of methanol and ether to furnish 18 mg of a yellow solid. $^1$H NMR (400 MHz) (DMSO-d$_6$) δ 3.47 (s, 3H), 3.96 (s, 3H), 4.06 (s, 3H), 4.09 (s, 3H), 7.36 (d, J=8.0 Hz, 2H), 7.59 (d, J=8.0 Hz, 2H), 7.66 (s, 1H), 7.77 (s, 1H), 7.99 (d, J=8.0 Hz, 1H), 8.77 (s, 1H), 8.90 (d, J=8.0 Hz, 1H), 9.63 (s, 1H).

The intermediate 1-(3,4-dimethoxybenzyl)-6-methoxy-7-(4-methylphenyl)isoquinoline was prepared as follows.

a. Preparation of Compound

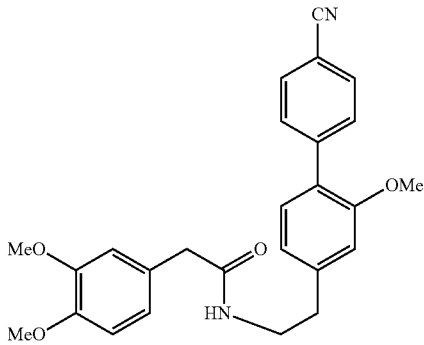 [SMILES: COc1ccc(CC(=O)NCCc2ccc(-c3ccc(C#N)cc3)c(OC)c2)cc1OC]

To a mixture of N-(4-bromo-3-methoxyphenethyl)-2-(3,4-dimethoxyphenyl)acetamide (200 mg), was added 4-cyanophenyl boronic acid (2 equivalents), Pd(PPh$_3$)$_2$Cl$_2$ (0.05 equivalents), and triphenylphosphine (0.1 equivalents) in a 2-neck round bottom flask and 8 mL of toluene/water mixture (4:1) and 2 M Na$_2$CO$_3$ (2 equivalents) were then added to the flask and reaction was refluxed at 90° C. overnight. Reaction mixture was cooled to room temperature and catalyst was filtered out. Organic layer was then washed with saturated NaHCO$_3$ solution, dried over sodium sulfate, and concentrated under vacuum. The compound was purified by chromatography on silica using 70% ethyl acetate/hexane to yield product as a white solid in 65% yield. $^1$H NMR (400 MHz) (CDCl$_3$) δ 2.81 (m, 2H), 3.52 (m, 4H), 3.79 (s, 3H), 3.84 (s, 6H), 5.52 (m, 1H), 6.73-6.82 (m, 5H), 7.18 (d, J=8.0 Hz, 1H), 7.63 (d, J=8.0 Hz, 2H), 7.69 (d, J=8.0 Hz, 2H).

b. Preparation of Compound

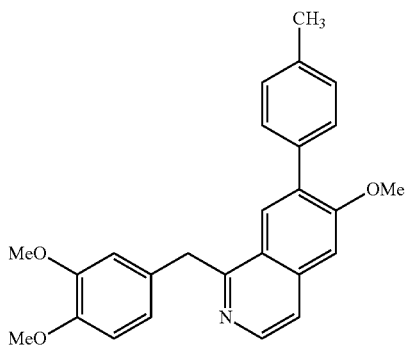 [SMILES: COc1ccc(Cc2nccc3cc(OC)c(-c4ccc(C)cc4)cc23)cc1OC]

A mixture of N-4-[4-cyanophenyl]-3-methoxyphenethyl)-2-(3,4-dimethoxyphenyl)acetamide and POCl$_3$ (4 equiv) in dry acetonitrile was heated at reflux for 1 hour. After the reaction is finished, the reaction mixture was diluted with H$_2$O, made basic (10% aqueous NH$_4$OH), and extracted with dichloromethane. The organic solution was washed with H$_2$O, dried with anhydrous sodium sulfate, and concentrated to give the dihydroisoquinoline, which was used for the next step without further purification.

The dihydroisoquinoline is heated at reflux with 10% Pd/C catalyst and tetralin (purged with nitrogen for 30 minutes prior to use) until the reaction is complete as judged by TLC. The catalyst is filtered from the cooled reaction mixture and washed with dichloromethane. Removal of tetralin by vacuum distillation affords the crude methyl derivative which was then purified by flash column chromatography on silica to give 70% yield of the pure compound as a white solid, wherein the cyano group was converted to a methyl group under these specific reaction conditions. $^1$H NMR (400 MHz) (CDCl$_3$) δ 2.35 (s, 3H), 3.72 (s, 3H), 3.74 (s, 3H), 3.86 (s, 3H), 4.47 (s, 2H), 6.67-6.73 (m, 2H), 6.80 (s, 1H), 7.05 (s, 1H), 7.19 (d, J=8.0 Hz, 2H), 7.31 (d, J=8.0 Hz, 2H), 7.40 (d, J=8.0 Hz, 1H), 8.02 (s, 1H), 8.35 (d, J=8.0 Hz, 1H).

Example 31

Preparation of Compound

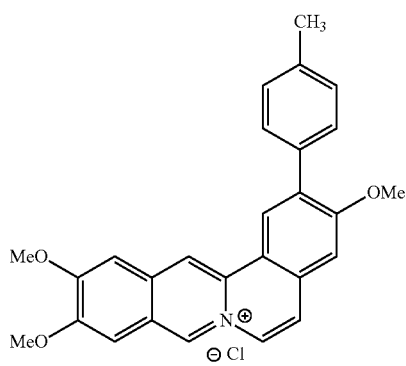 [SMILES: COc1cc2cc3c4cc(-c5ccc(C)cc5)c(OC)cc4cc[n+]3cc2cc1OC ; [Cl-]]

Phosphorus oxychloride (0.2 mL) was added dropwise to chilled (0° C.) DMF (1.0 mL) under nitrogen. The reaction mixture was stirred for 15 minutes at 0° C. A solution of 1-(3,4-dimethoxybenzyl)-6-methoxy-7-(4-methylphenyl) isoquinoline (20 mg) in 1 mL of DMF was added and allowed to stir at 0° C. for 1 hour. The reaction mixture was subsequently heated at 100° C. for 1 hour. After 1 h at 100° C., the reaction mixture was cooled down and was added to a flask containing some cubes of ice and 0.5 mL of 6N HCl. The solid thus formed was filtered off, washed with a small amount of methanol and ether to afford 18 mg of a yellow solid. $^1$H NMR (400 MHz) (DMSO-$d_6$) δ 4.00 (s, 3H), 4.04 (s, 3H), 4.08 (s, 3H), 7.36 (d, J=8.0 Hz, 2H), 7.59 (d, J=8.0 Hz, 2H), 7.66 (s, 1H), 7.70 (s, 1H), 7.75 (s, 1H), 7.99 (d, J=8.0 Hz, 1H), 8.77 (s, 1H), 8.81 (d, J=8.0 Hz, 1H), 9.69 (s, 1H), 9.95 (s, 1H).

Example 32

Preparation of Compound

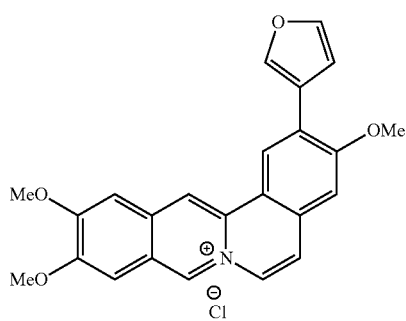 [SMILES: COc1cc2cc3c4cc(-c5ccoc5)c(OC)cc4cc[n+]3cc2cc1OC ; [Cl-]]

Phosphorus oxychloride (0.2 mL) was added dropwise to chilled (0° C.) DMF (1.0 mL) under nitrogen. The reaction mixture was stirred for 15 minutes at 0° C. A solution of 1-(3,4-dimethoxybenzyl)-6-methoxy-7-(furan-3-yl)isoquinoline (9.0 mg) in 1 mL of DMF was added and allowed to stir at 0° C. for 1 hour. The reaction mixture was subsequently heated at 100° C. for 1 hour. After 1 h at 100° C., the reaction mixture was cooled down and was added to a flask containing some cubes of ice and 0.5 mL of 6N HCl. The solid thus formed was filtered off, washed with a small amount of methanol and ether to afford 6.7 mg of a yellow solid. $^1$H NMR (400 MHz) (DMSO-$d_6$) δ 4.04 (s, 3H), 4.06 (s, 3H), 4.12 (s, 3H), 7.12 (s, 1H), 7.65 (s, 1H), 7.79 (s, 1H), 7.87 (s, 1H), 8.05 (d, J=8.0 Hz, 1H), 8.26 (s, 1H), 8.90 (d, J=8.0 Hz, 1H), 9.08 (s, 1H), 9.66 (s, 1H), 9.79 (s, 1H), 10.07 (s, 1H).

The intermediate 1-(3,4-dimethoxybenzyl)-6-methoxy-7-(furan-3-yl)isoquinoline was prepared as follows.

a. Preparation of Compound

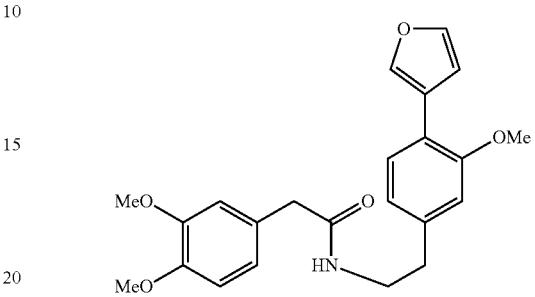

To a solution of N-(4-bromo-3-methoxyphenethyl)-2-(3,4-dimethoxyphenyl)acetamide (0.5 mmol) in 3 mL of dioxane was added 3-furanyl boronic acid (1.0 mmol), Pd(PPh$_3$)$_2$Cl$_2$ (10 mol %) and Cs$_2$CO$_3$ (1.5 mmol). The mixture was irradiated at 120° C. for 10 minutes using a microwave reactor and cooled to room temperature. The mixture was diluted with ethyl acetate and filtered through a short Celite pad. The solution was concentrated in vacuo and purified by flash column chromatography on silica using ethyl acetate:hexane solvent system to provide the desired compound in 60% yield. $^1$H NMR (400 MHz) (CDCl$_3$) δ 2.66 (m, 2H), 3.40 (m, 4H), 3.72 (s, 3H), 3.76 (s, 3H), 3.79 (s, 5.35 (m, 1H), 6.58 (m, 2H), 6.67 (m, 2H), 7.29 (m, 2H), 7.38 (m, 1H), 7.89 (s, 1H).

b. Preparation of Compound

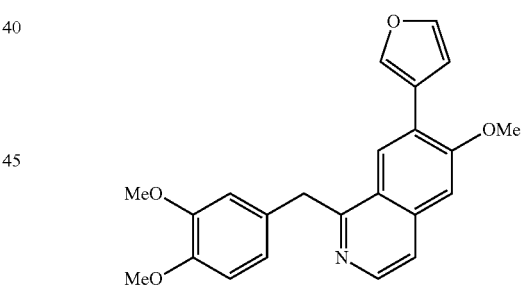

A mixture of N-4-[4-(3-furanyl)]-3-methoxyphenethyl)-2-(3,4-dimethoxyphenyl)acetamide and POCl$_3$ (4 equiv) in dry acetonitrile was heated at reflux for 1 hour. After the reaction is finished, the reaction mixture was diluted with H$_2$O, made basic (10% aqueous NH$_4$OH), and extracted with dichloromethane. The organic solution was washed with H$_2$O, dried with anhydrous sodium sulfate, and concentrated to give the dihydroisoquinoline, which was used for the next step without further purification.

The dihydroisoquinoline is heated at reflux with 10% Pd/C catalyst and tetralin (purged with nitrogen for 30 minutes prior to use) until the reaction is complete as judged by TLC. The catalyst is filtered from the cooled reaction mixture and washed with dichloromethane. Removal of tetralin by vacuum distillation affords the crude product which was then purified by flash column chromatography on silica to give 15% yield of the pure compound as a white solid. ¹H NMR (400 MHz) (CDCl₃) δ 3.71 (s, 3H), 3.74 (s, 3H), 3.96 (s, 3H), 4.51 (s, 2H), 6.67-6.71 (m, 2H), 6.78 (m, 2H), 7.05 (s, 1H), 7.37 (d, J=8.0 Hz, 1H), 7.42 (m, 1H), 7.92 (s, 1H), 8.17 (s, 1H), 8.31 (d, J=8.0 Hz, 1H).

Example 33

Preparation of Compound

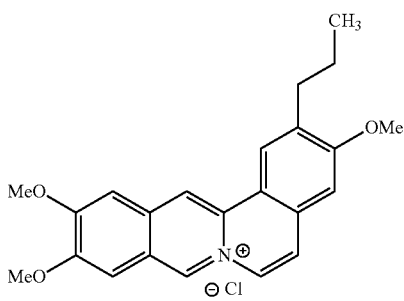 [SMILES: CCCc1cc2c(cc[n+]3cc4cc(OC)c(OC)cc4cc23)cc1OC ; [Cl-]]

Phosphorus oxychloride (0.2 mL) was added dropwise to chilled (0° C.) DMF (1.0 mL) under nitrogen. The reaction mixture was stirred for 15 minutes at 0° C. A solution of 1-(3,4-dimethoxybenzyl)-6-methoxy-7-(n-propyl)isoquinoline (13 mg in 1.0 mL) of DMF was added and allowed to stir at 0° C. for 1 hour. The reaction mixture was subsequently heated at 100° C. for 1 hour. After 1 h at 100° C., the reaction mixture was cooled down and was added to a flask containing some cubes of ice and 0.5 mL of 6N HCl. The solid thus formed was filtered off, washed with small amount of methanol and ether to afford 7.9 mg of a yellow solid. ¹H NMR (400 MHz) (DMSO-d₆) δ 0.86 (t, 3H) 1.57 (m, 2H) 22.63 (t, 2H) 4.04 (s, 3H), 4.06 (s, 3H) 4.13 (s 3H), 7.66 (s, 1H), 7.74 (s, 1H), 6.01 (d, J=8.0 Hz, 1H), 8.22 (s, 1H), 8.76 (s, 1H), 8.82 (d, J=8.0 Hz, 1H), 9.69 (s, 1H), 10.01 (s, 1H).

The intermediate 1-(3,4-dimethoxybenzyl)-6-methoxy-7-(n-propyl)isoquinoline was prepared as follows.
a. Preparation of Compound

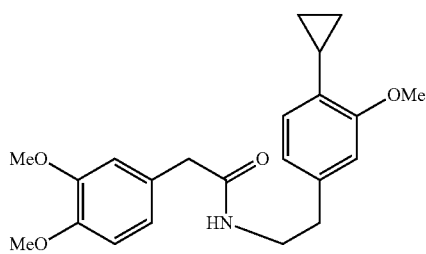 [SMILES: COc1ccc(CC(=O)NCCc2ccc(C3CC3)c(OC)c2)cc1OC]

To a mixture of N-(4-bromo-3-methoxyphenethyl)-2-(3,4-dimethoxyphenyl)acetamide (100 mg), cyclopropyl boronic acid (2 equivalents), palladium acetate (0.05 equivalents), potassium phosphate (3.5 equivalents), and tricyclohexylphospine (0.1 equivalents) were combined in a 2-neck round bottom flask and degassed for 1 hour under vacuum. A solution of toluene/water, 3 mL, (20:1) was then added to the flask, and the reaction mixed was refluxed at 100° C. under nitrogen for 3 hours. Reaction mixture was then cooled to room temperature and catalyst was filtered out. Organic layer was then washed with saturated NaHCO₃ solution, dried over sodium sulfate, and concentrated under vacuum. Separation obtained with chromatography on silica using 70% ethyl acetate/hexane to yield product as a white solid in 75% yield. ¹H NMR (400 MHz) (CDCl₃) δ 0.63 (m, 2H), 0.92 (m, 2H), 2.13 (m, 1H), 2.71 (t, J=4.0 Hz, 2H), 3.48 (m, 4H), 3.82 (s, 3H), 3.84 (s, 3H), 3.90 (s, 3H), 5.47 (bs, 1H), 6.53 (d, J=8.0 Hz, 1H), 6.59 (s, 1H), 6.70 (m, 3H), 6.80 (m, 1H).
b. Preparation of Compound

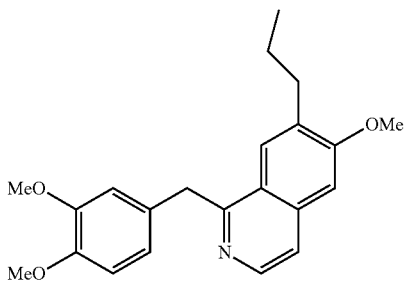 [SMILES: CCCc1cc2c(Cc3ccc(OC)c(OC)c3)nccc2cc1OC]

A mixture of N-4-[4-(cyclopropyl)]-3-methoxyphenethyl)-2-(3,4-dimethoxyphenyl)acetamide and POCl₃ (4 equiv) in dry acetonitrile was heated at reflux for 1 hour. After the reaction is finished, the reaction mixture was diluted with H₂O, made basic (10% aqueous NH₄OH), and extracted with dichloromethane. The organic solution was washed with H₂O, dried with anhydrous sodium sulfate, and concentrated to give the dihydroisoquinoline, which was used for the next step without further purification.

The dihydroisoquinoline is heated at reflux with 10% Pd/C catalyst and tetralin (purged with nitrogen for 30 minutes prior to use) until the reaction is complete as judged by TLC. The catalyst is filtered from the cooled reaction mixture and washed with dichloromethane. Removal of tetralin by vacuum distillation affords the crude product n-propyl derivative which was then purified by flash column chromatography on silica to give the pure compound as a white solid in 50% yield, wherein the cyclopropyl was converted to an n-propyl group under these reaction conditions. ¹H NMR (400 MHz) (CDCl₃) δ 0.86 (t, 3H), 1.56 (m, 2H), 2.62 (t, 2H), 3.71 (s, 3H), 3.73 (s, 3H), 3.86 (s, 3H), 4.46 (s, 2H), 6.66-6.78 (m, 3H), 6.93 (s, 1H), 7.35 (d, J=8.0 Hz, 1H), 7.81 (s, 1H), 8.29 (d, J=8.0 Hz, 1H).

Example 34

Preparation of Compound

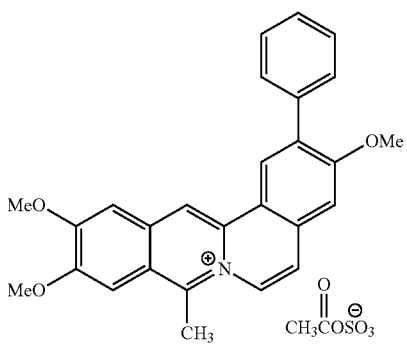

Fuming sulfuric acid (0.2 mL) was added to 0.8 mL freshly distilled acetic anhydride resulting in a vigorous exothermic reaction and the mixture becoming wine-red in color. This mixture was heated at 85-90° C. for 10 minutes. A solution of 1-(3,4-dimethoxybenzyl)-6-methoxy-7-(phenyl)isoquinoline (23 mg) in 1 mL of Ac$_2$O was added under nitrogen to the wine red sulfuric acid solution and the resulting mixture was heated at 85-90° C. for 1 h. The reaction mixture was cooled to room temperature and methanol was added. The solution was then chilled and ether was added until a solid precipitated. The solid was then filtered off, washed with small amount of methanol and ether to furnish 17 mg of a yellow solid. $^1$H NMR (400 MHz) (DMSO-d$_6$) δ 3.40 (s, 3H), 3.98 (s, 3H), 4.03 (s, 3H), 4.07 (s, 3H), 7.48 (d, J=8.0 Hz, 1H), 7.54 (t, J=8.0 Hz, 2H), 7.63 (s, 1H), 7.68-7.73 (m, 4H), 7.95 (d, J=8.0 Hz, 1H), 8.75 (s, 1H), 8.86 (d, J=8.0 Hz, 1H), 9.60 (s, 1H).

The intermediate 1-(3,4-dimethoxybenzyl)-6-methoxy-7-(phenyl)isoquinoline was prepared as follows.

a. Preparation of Compound

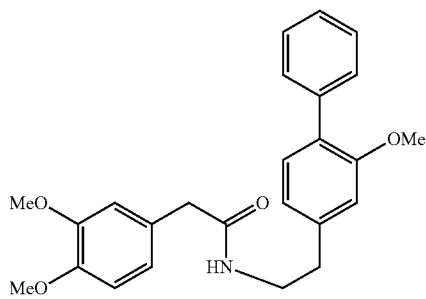 [SMILES: COc1ccc(CC(=O)NCCc2ccc(-c3ccccc3)c(OC)c2)cc1OC]

To a solution of N-(4-bromo-3-methoxyphenethyl)-2-(3,4-dimethoxyphenyl)acetamide (0.5 mmol) in 3 mL of dioxane was added phenyl boronic acid (1.0 mmol), Pd(PPh$_3$)$_2$Cl$_2$ (10 mol %) and Cs$_2$CO$_3$ (1.5 mmol). The mixture was irradiated at 120° C. for 10 minutes using a microwave reactor and cooled to room temperature. The mixture was diluted with ethyl acetate and filtered through a short Celite pad. The solution was concentrated in vacuo and purified by flash column chromatography on silica using ethyl acetate:hexane solvent system to provide the desired compound in 90% yield. $^1$H NMR (400 MHz) (CDCl$_3$) δ 2.81 (t, J=8 Hz 2H), 3.53 (m, 4H), 3.78 (s, 3H), 3.83 (s, 3H), 3.85 (s, 3H), 5.5 (m, 1H), 6.70-6.74 (m 4H), 6.80 (d, J=8.0 Hz, 1H), 7.20 (d, J=8.0 Hz, 1H) 7.34 (m, 1H) 7.40-7.44 (m, 2H), 7.51-7.54 (m, 2H).

b. Preparation of Compound

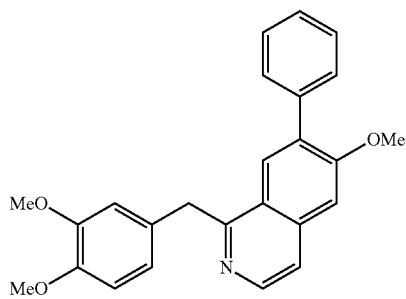 [SMILES: COc1ccc(Cc2nccc3cc(OC)c(-c4ccccc4)cc23)cc1OC]

A mixture of 2-(3,4-dimethoxyphenyl)-N-(2-(2-methoxybiphenyl-4-yl)ethyl)acetamide and POCl$_3$ (4 equiv) in dry acetonitrile was heated at reflux for 1 hour. After the reaction is finished, the reaction mixture was diluted with H$_2$O, made basic (10% aqueous NH$_4$OH), and extracted with dichloromethane. The organic solution was washed with H$_2$O, dried with anhydrous sodium sulfate, and concentrated to give the dihydroisoquinoline, which was used for the next step without further purification.

The dihydroisoquinoline is heated at reflux with 10% Pd/C catalyst and tetralin (purged with nitrogen for 30 minutes prior to use) until the reaction is complete as judged by TLC. The catalyst is filtered from the cooled reaction mixture and washed with dichloromethane. Removal of tetralin by vacuum distillation affords the crude product which was then purified by flash column chromatography on silica to give an 89% yield of the pure compound as a white solid. $^1$H NMR (400 MHz) (CDCl$_3$) δ 3.82 (s, 3H), 3.84 (s, 3H), 3.97 (s, 3H), 4.61 (s, 2H), 6.78 (d, J=8.0 Hz, 1H), 6.84 (dd, J=8.0 Hz, 4.0 Hz, 1H), 6.94 (s, 1H), 7.18 (s, 1H), 7.45-7.54 (m, 6H), 8.15 (s, 1H), 8.45 (d, J=8.0 Hz, 1H).

Example 35

Preparation of Compound

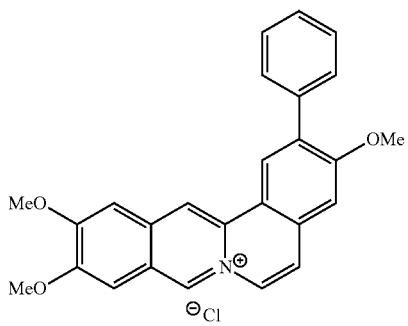 [SMILES: COc1cc2cc3c4cc(-c5ccccc5)c(OC)cc4cc[n+]3cc2cc1OC ; [Cl-]]

Phosphorus oxychloride (0.2 mL) was added dropwise to chilled (0° C.) DMF (1.0 mL) under nitrogen. The reaction mixture was stirred for 15 minutes at 0° C. A solution of 1-(3,4-dimethoxybenzyl)-6-methoxy-7-phenylisoquinoline (21 mg) in 1 mL of DMF was added and allowed to stir at 0° C. for 1 hour. The reaction mixture was subsequently heated at 100° C. for 1 hour. After 1 h at 100° C., the reaction mixture was cooled down and was added to a flask containing some cubes of ice and 0.5 mL of 6N HCl. The solid thus formed was filtered off, washed with a small amount of methanol and ether to afford 20 mg of a yellow solid. $^1$H NMR (400 MHz) (DMSO-d$_6$) δ 4.02 (s, 3H), 4.06 (s, 3H), 4.09 (s, 3H), 7.50 (d, J=8.0 Hz, 1H), 7.56 (t, J=8.0 Hz, 2H), 7.70 (m, 4H), 7.80 (s, 1H), 8.04 (d, J=8.0 Hz, 1H), 8.83 (s, 1H), 8.85 (d, J=8.0 Hz, 1H), 9.75 (s, 1H), 10.01 (s, 1H).

Example 36

The following can illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |

-continued

| | |
|---|---|
| Magnesium stearate | 3.0 |
| | 300.0 |
| (ii) Tablet 2 | mg/tablet |
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |
| (iii) Capsule | mg/capsule |
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |
| (iv) Injection 1 (1 mg/ml) | mg/ml |
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (v) Injection 2 (10 mg/ml) | mg/ml |
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |
| (vi) Aerosol | mg/can |
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

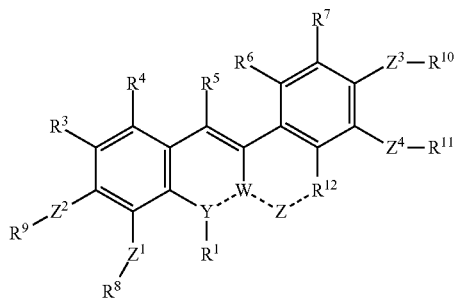

wherein:
the dashed line between Y and W represents a single or double bond;

when Y is —$CR^2$—, Z is —$(CR^{13}_2)_2$— or —$CR^{14}$=$CR^{14}$— and $R^{12}$ is a bond; W is N or $(NR^a)^+$ $X^-$;

when Y is —C=, Z is —$(CR^{13}_2)_2$— or —$CR^{14}$=$CR^{14}$— and $R^{12}$ is a bond; W is $N^+X^-$; or $X^-$ is a pharmaceutically suitable counterion;

$Z^1$, $Z^2$, $Z^3$ and $Z^4$ are each independently O, S or $NR^e$; or $R^8$—$Z^1$—, $R^9$—$Z^2$—, $R^{10}$—$Z^3$—, and $R^{11}$—$Z^4$— can each independently be H, optionally substituted aryl or optionally substituted heteroaryl;

$R^1$ is H, ($C_1$-$C_6$)alkyl, ($C_1$-$C_6$)alkoxy, ($C_1$-$C_6$)alkylthio, aryloxy or arylthio; and $R^2$ is H or ($C_1$-$C_6$)alkyl, wherein any ($C_1$-$C_6$)alkyl, ($C_1$-$C_6$)alkoxy, and ($C_1$-$C_6$)alkylthio of $R^1$ and $R^2$ is optionally substituted with one or more groups selected from halo, cyano, oxo (=O), ($C_1$-$C_6$)alkyl, ($C_3$-$C_6$)cycloalkyl, carboxy, $NO_2$, hydroxy, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —$NR^hR^i$, and wherein any aryloxy, or arylthio of $R^1$ and $R^2$ is optionally substituted with one or more groups selected from halo, cyano, ($C_1$-$C_6$)alkyl, ($C_3$-$C_6$)cycloalkyl, carboxy, $NO_2$, hydroxy, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —$NR^hR^i$;

at least one of $R^3$, $R^4$, $R^5$, $R^6$ and $R^7$ is aryl, heteroaryl, aryl($C_1$-$C_6$)alkyl, heteroaryl($C_1$-$C_6$)alkyl, aryl($C_1$-$C_6$)alkanoyl or heteroaryl($C_1$-$C_6$)alkanoyl and the remainder of $R^3$, $R^4$, $R^5$, $R^6$ and $R^7$ are independently H, halo, nitro, sulfo, —$S(O)_2NR''R^p$, —$N(R'')$ $S(O)_2R^p$, —$NR^hR^i$ optionally substituted alkyl, optionally substituted arylalkyl, optionally substituted heteroarylalkyl, optionally substituted aryl, or optionally substituted heteroaryl; or $R^3$ is —$Z^{13}R^{13'}$ wherein $Z^{13}$ is O, S or $NR^e$ and $R^{13'}$ is ($C_1$-$C_6$)alkyl, substituted ($C_1$-$C_6$)alkyl, ($C_1$-$C_6$)alkanoyl or —C(=O)$NR^fR^g$ or $R^{13'}$ and $R^9$ together with the atoms to which they are attached form a 5 to 7 membered ring; or $R^6$ and $R^7$ together with the atoms to which are attached form a 5 to 6 membered heterocycle wherein the heterocycle is optionally fused with an optionally substituted aryl;

$R^8$ and $R^9$ are each independently, ($C_1$-$C_6$)alkyl, ($C_1$-$C_6$) alkanoyl or —C(=O)$NR^fR^g$ or $R^8$ and $R^9$ together with the atoms to which they are attached form a 5 to 7 membered ring; or R⁸—Z¹— and R⁹—Z²— can each independently be H;

R¹⁰ and R¹¹ are each independently, $(C_1-C_6)$alkyl, $(C_1-C_6)$alkanoyl or —C(=O)NR$^f$R$^g$ or R¹⁰ and R¹¹ together with the atoms to which they are attached form a 5 to 7 membered ring; or R¹⁰—Z³—, and R¹¹—Z⁴— can each independently be H;

each R¹³ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of R¹³ is optionally substituted with one or more groups selected from halo, cyano, oxo (=O), $(C_1-C_6)$alkyl, $(C_3-C_6)$cycloalkyl, carboxy, NO₂, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^h$R$^i$, and wherein any aryloxy, or arylthio of R¹³ is optionally substituted with one or more groups selected from halo, cyano, $(C_1-C_6)$alkyl, $(C_3-C_6)$cycloalkyl, carboxy, NO₂, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^h$R$^i$;

each R¹⁴ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of R¹⁴ is optionally substituted with one or more groups selected from halo, cyano, oxo (=O), $(C_1-C_6)$alkyl, $(C_3-C_6)$cycloalkyl, carboxy, NO₂, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^h$R$^i$, and wherein any aryloxy, or arylthio of R¹⁴ is optionally substituted with one or more groups selected from halo, cyano, $(C_1-C_6)$alkyl, $(C_3-C_6)$cycloalkyl, carboxy, NO₂, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^h$R$^i$;

R$^a$ is $(C_1-C_6)$alkyl wherein $(C_1-C_6)$alkyl is optionally substituted with one or more groups independently selected from halo, cyano, oxo (=O), $(C_1-C_6)$alkyl, $(C_3-C_6)$cycloalkyl, carboxy, NO₂, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^h$R$^i$;

each R$^e$ is independently H or $(C_1-C_6)$alkyl wherein $(C_1-C_6)$alkyl is optionally substituted with one or more halo;

R$^f$ and R$^g$ are each independently H, $(C_1-C_6)$alkyl, aryl, heteroaryl, aryl$(C_1-C_6)$ alkyl or heteroaryl$(C_1-C_6)$ alkyl; or R$^f$ and R$^g$ together with the nitrogen to which they are attached form a morpholino, piperazino, pyrrolidino or piperidino;

R$^h$ and R$^i$ are each independently H, $(C_1-C_6)$alkyl, aryl, heteroaryl, aryl$(C_1-C_6)$ alkyl or heteroaryl$(C_1-C_6)$ alkyl; or R$^h$ and R$^i$ together with the nitrogen to which they are attached form a morpholino, piperazino, pyrrolidino or piperidino; and wherein R$^n$ and R$^p$ may be the same or different and are chosen from hydrogen, alkyl, arylalkyl, heteroarylalkyl, cycloalkyl, substituted cycloalkyl, aryl, heteroaryl and heterocyclic;

or a salt or prodrug thereof, which is a compound of the following formula:

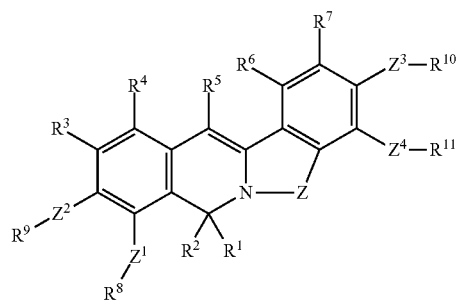

or a salt thereof.

2. A compound of formula I:

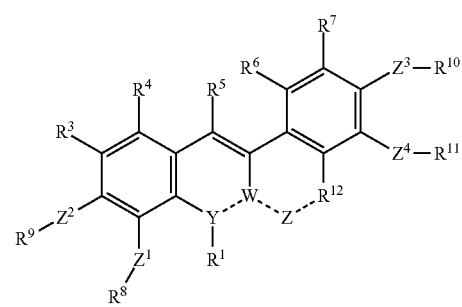

wherein:
the dashed line between Y and W represents a single or double bond;
when Y is —CR²—, Z is —(CR¹³₂)₂— or —CR¹⁴=CR¹⁴— and R¹² is a bond; W is N or (NR$^a$)⁺ X⁻;
when Y is —C=, Z is —(CR¹³₂)₂— or —CR¹⁴=CR¹⁴— and R¹² is a bond; W is N⁺X⁻; or
X⁻ is a pharmaceutically suitable counterion;
Z¹, Z², Z³ and Z⁴ are each independently O, S or NR$^e$; or R⁸—Z¹—, R⁹—Z²—, R¹⁰—Z³—, and R¹¹—Z⁴— can each independently be H, optionally substituted aryl or optionally substituted heteroaryl;
R¹ is H, $(C_1-C_6)$alkyl, $(C_1-C_6)$alkoxy, $(C_1-C_6)$alkylthio, aryloxy or arylthio; and R² is H or $(C_1-C_6)$alkyl, wherein any $(C_1-C_6)$alkyl, $(C_1-C_6)$alkoxy, and $(C_1-C_6)$alkylthio of R¹ and R² is optionally substituted with one or more groups selected from halo, cyano, oxo (=O), $(C_1-C_6)$alkyl, $(C_3-C_6)$cycloalkyl, carboxy, NO₂, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^h$R$^i$, and wherein any aryloxy, or arylthio of R¹ and R² is optionally substituted with one or more groups selected from halo, cyano, $(C_1-C_6)$alkyl, $(C_3-C_6)$cycloalkyl, carboxy, NO₂, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^h$R$^i$;
at least one of R³, R⁴, R⁵, R⁶ and R⁷ is aryl, heteroaryl, aryl$(C_1-C_6)$alkyl, heteroaryl$(C_1-C_6)$alkyl, aryl$(C_1-C_6)$alkanoyl or heteroaryl$(C_1-C_6)$alkanoyl and the remainder of R³, R⁴, R⁵, R⁶ and R⁷ are independently H, halo, nitro, sulfo, —S(O)₂NR$^n$R$^p$, —N(R$^n$)S(O)₂R$^p$, —NR$^h$R$^i$ optionally substituted alkyl, optionally substituted arylalkyl, optionally substituted heteroarylalkyl, optionally substituted aryl, or optionally substituted heteroaryl; or $R^3$ is —$Z^{13}R^{13'}$ wherein $Z^{13}$ is O, S or $NR^e$ and $R^{13'}$ is $(C_1-C_6)$alkyl, substituted $(C_1-C_6)$alkyl, $(C_1-C_6)$alkanoyl or —C(=O)$NR^fR^g$ or $R^{13'}$ and $R^9$ together with the atoms to which they are attached form a 5 to 7 membered ring; or $R^6$ and $R^7$ together with the atoms to which they are attached form a 5 to 6 membered heterocycle wherein the heterocycle is optionally fused with an optionally substituted aryl;

$R^8$ and $R^9$ are each independently, $(C_1-C_6)$alkyl, $(C_1-C_6)$alkanoyl or —C(=O)$NR^fR^g$ or $R^8$ and $R^9$ together with the atoms to which they are attached form a 5 to 7 membered ring; or $R^8$—$Z^1$— and $R^9$—$Z^2$— can each independently be H;

$R^{10}$ and $R^{11}$ are each independently, $(C_1-C_6)$alkyl, $(C_1-C_6)$alkanoyl or —C(=O)$NR^fR^g$ or $R^{10}$ and $R^{11}$ together with the atoms to which they are attached form a 5 to 7 membered ring; or $R^{10}$—$Z^3$—, and $R^{11}$—$Z^4$— can each independently be H;

each $R^{13}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{13}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^{13}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;

each $R^{14}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{14}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^{14}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;

$R^a$ is $(C_1-C_6)$alkyl wherein $(C_1-C_6)$alkyl is optionally substituted with one or more groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;

each $R^e$ is independently H or $(C_1-C_6)$alkyl wherein $(C_1-C_6)$alkyl is optionally substituted with one or more halo;

$R^f$ and $R^g$ are each independently H, $(C_1-C_6)$alkyl, aryl, heteroaryl, aryl$(C_1-C_6)$ alkyl or heteroaryl$(C_1-C_6)$ alkyl; or $R^f$ and $R^g$ together with the nitrogen to which they are attached form a morpholino, piperazino, pyrrolidino or piperidino;

$R^h$ and $R^i$ are each independently H, $(C_1-C_6)$alkyl, aryl, heteroaryl, aryl$(C_1-C_6)$ alkyl or heteroaryl$(C_1-C_6)$ alkyl; or $R^h$ and $R^i$ together with the nitrogen to which they are attached form a morpholino, piperazino, pyrrolidino or piperidino; and wherein $R^n$ and $R^p$ may be the same or different and are chosen from hydrogen, alkyl, arylalkyl, heteroarylalkyl, cycloalkyl, substituted cycloalkyl, aryl, heteroaryl and heterocyclic;

or a salt or prodrug thereof, which is a compound of the following formula:

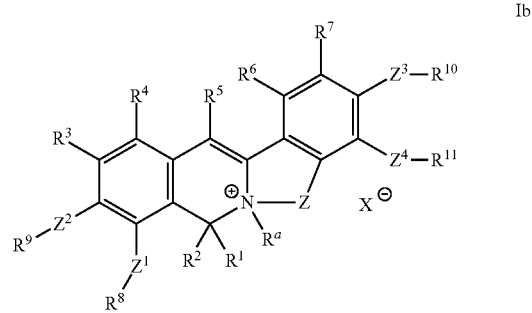

or a salt thereof.

3. A compound of formula I:

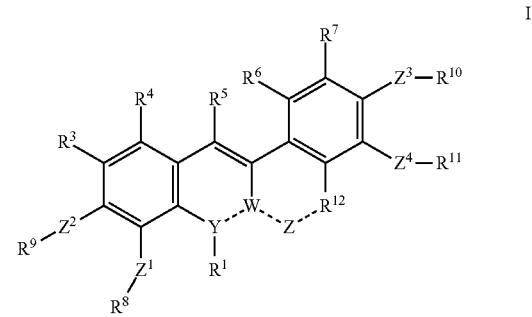

wherein:
the dashed line between Y and W represents a single or double bond;

when Y is —$CR^2$—, Z is —$(CR^{13}_2)_2$— or —$CR^{14}$=$CR^{14}$— and $R^{12}$ is a bond; W is N or $(NR^a)^+$ $X^-$;

when Y is —C=, Z is —$(CR^{13}_2)_2$— or —$CR^{14}$=$CR^{14}$— and $R^{12}$ is a bond; W is $N^+X^-$; or $X^-$ is a pharmaceutically suitable counterion;

$Z^1$, $Z^2$, $Z^3$ and $Z^4$ are each independently O, S or $NR^e$; or $R^8$—$Z^1$—, $R^9$—$Z^2$—, $R^{10}$—$Z^3$—, and $R^{11}$—$Z^4$— can each independently be H, optionally substituted aryl or optionally substituted heteroaryl;

$R^1$ is H, $(C_1-C_6)$alkyl, $(C_1-C_6)$alkoxy, $(C_1-C_6)$alkylthio, aryloxy or arylthio; and $R^2$ is H or $(C_1-C_6)$alkyl, wherein any $(C_1-C_6)$alkyl, $(C_1-C_6)$alkoxy, and $(C_1-C_6)$alkylthio of $R^1$ and $R^2$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^1$ and $R^2$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;

at least one of $R^3$, $R^4$, $R^5$, $R^6$ and $R^7$ is aryl, heteroaryl, aryl$(C_1-C_6)$alkyl, heteroaryl$(C_1-C_6)$alkyl, aryl$(C_1-C_6)$alkanoyl or heteroaryl$(C_1-C_6)$alkanoyl and the remainder of $R^3$, $R^4$, $R^5$, $R^6$ and $R^7$ are independently H, halo, nitro, sulfo, —$S(O)_2NR''R^p$, —$N(R'')S(O)_2R^p$, —$NR^hR^i$ optionally substituted alkyl, optionally substituted arylalkyl, optionally substituted heteroarylalkyl, optionally substituted aryl, or optionally substituted heteroaryl; or $R^3$ is —$Z^{13}R^{13'}$ wherein $Z^{13}$ is O, S or $NR^e$ and $R^{13'}$ is $(C_1-C_6)$alkyl, substituted $(C_1-C_6)$alkyl, $(C_1-C_6)$alkanoyl or —$C(=O)NR^fR^g$ or $R^{13'}$ and $R^9$ together with the atoms to which they are attached form a 5 to 7 membered ring; or $R^6$ and $R^7$ together with the atoms to which they are attached form a 5 to 6 membered heterocycle wherein the heterocycle is optionally fused with an optionally substituted aryl;

$R^8$ and $R^9$ are each independently, $(C_1-C_6)$alkyl, $(C_1-C_6)$alkanoyl or —$C(=O)NR^fR^g$ or $R^8$ and $R^9$ together with the atoms to which they are attached form a 5 to 7 membered ring; or $R^8$—$Z^1$— and $R^9$—$Z^2$— can each independently be H;

$R^{10}$ and $R^{11}$ are each independently, $(C_1-C_6)$alkyl, $(C_1-C_6)$alkanoyl or —$C(=O)NR^fR^g$ or $R^{10}$ and $R^{11}$ together with the atoms to which they are attached form a 5 to 7 membered ring; or $R^{10}$—$Z^3$—, and $R^{11}$—$Z^4$— can each independently be H;

each $R^{13}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{13}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^{13}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;

each $R^{14}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{14}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^{14}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;

$R^a$ is $(C_1-C_6)$alkyl wherein $(C_1-C_6)$alkyl is optionally substituted with one or more groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;

each $R^e$ is independently H or $(C_1-C_6)$alkyl wherein $(C_1-C_6)$alkyl is optionally substituted with one or more halo;

$R^f$ and $R^g$ are each independently H, $(C_1-C_6)$alkyl, aryl, heteroaryl, aryl$(C_1-C_6)$ alkyl or heteroaryl$(C_1-C_6)$ alkyl; or $R^f$ and $R^g$ together with the nitrogen to which they are attached form a morpholino, piperazino, pyrrolidino or piperidino;

$R^h$ and $R^i$ are each independently H, $(C_1-C_6)$alkyl, aryl, heteroaryl, aryl$(C_1-C_6)$ alkyl or heteroaryl$(C_1-C_6)$ alkyl; or $R^h$ and $R^i$ together with the nitrogen to which they are attached form a morpholino, piperazino, pyrrolidino or piperidino; and wherein $R^n$ and $R^p$ may be the same or different and are chosen from hydrogen, alkyl, arylalkyl, heteroarylalkyl, cycloalkyl, substituted cycloalkyl, aryl, heteroaryl and heterocyclic;

or a salt or prodrug thereof, which is a compound of formula Ih:

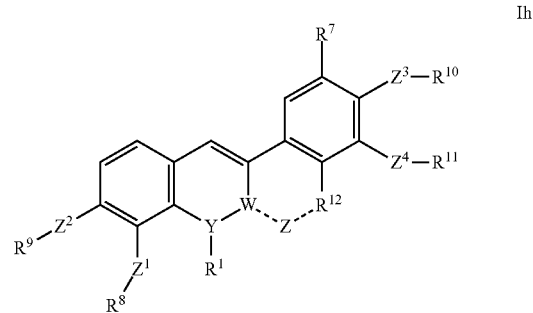

Ih or a salt thereof.

4. A compound of formula I:

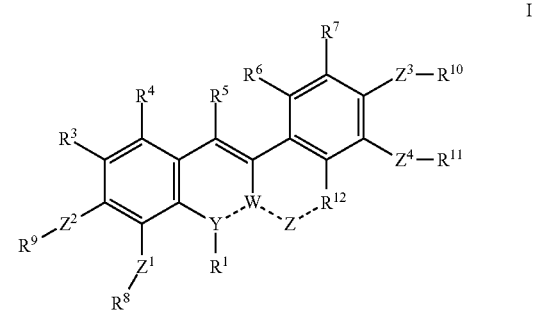

I wherein:
the dashed line between Y and W represents a single or double bond;
when Y is —$CR^2$—, Z is —$(CR^{13}_2)_2$— or —$CR^{14}$=$CR^{14}$— and $R^{12}$ is a bond; W is N or $(NR^a)^+X^-$;
when Y is —C=, Z is —$(CR^{13}_2)_2$— or —$CR^{14}$=$CR^{14}$— and $R^{12}$ is a bond; W is $N^+X^-$; or $X^-$ is a pharmaceutically suitable counterion;
$Z^1$, $Z^2$, $Z^3$ and $Z^4$ are each independently O, S or $NR^e$; or $R^8$—$Z^1$—, $R^9$—$Z^2$—, $R^{10}$—$Z^3$—, and $R^{11}$—$Z^4$— can each independently be H, optionally substituted aryl or optionally substituted heteroaryl;
$R^1$ is H, $(C_1-C_6)$alkyl, $(C_1-C_6)$alkoxy, $(C_1-C_6)$alkylthio, aryloxy or arylthio; and $R^2$ is H or $(C_1-C_6)$alkyl, wherein any (C₁-C₆)alkyl, (C₁-C₆)alkoxy, and (C₁-C₆)alkylthio of R¹ and R² is optionally substituted with one or more groups selected from halo, cyano, oxo (=O), (C₁-C₆)alkyl, (C₃-C₆)cycloalkyl, carboxy, NO₂, hydroxy, (C₁-C₆)alkoxy, (C₁-C₆)alkoxycarbonyl, (C₁-C₆)alkanoyloxy, aryl, heteroaryl, aryloxy, heteroaryloxy, and —NRʰRⁱ, and wherein any aryloxy, or arylthio of R¹ and R² is optionally substituted with one or more groups selected from halo, cyano, (C₁-C₆)alkyl, (C₃-C₆)cycloalkyl, carboxy, NO₂, hydroxy, (C₁-C₆)alkoxy, (C₁-C₆)alkoxycarbonyl, (C₁-C₆)alkanoyloxy, aryl, heteroaryl, aryloxy, heteroaryloxy, and —NRʰRⁱ;

at least one of R³, R⁴, R⁵, R⁶ and R⁷ is aryl, heteroaryl, aryl(C₁-C₆)alkyl, heteroaryl(C₁-C₆)alkyl, aryl(C₁-C₆)alkanoyl or heteroaryl(C₁-C₆)alkanoyl and the remainder of R³, R⁴, R⁵, R⁶ and R⁷ are independently H, halo, nitro, sulfo, —S(O)₂NR″Rᵖ, —N(R″)S(O)₂Rᵖ, —NRʰRⁱ optionally substituted alkyl, optionally substituted arylalkyl, optionally substituted heteroarylalkyl, optionally substituted aryl, or optionally substituted heteroaryl; or R³ is —Z¹³R¹³' wherein Z¹³ is O, S or NRᵉ and R¹³' is (C₁-C₆)alkyl, substituted (C₁-C₆)alkyl, (C₁-C₆)alkanoyl or —C(=O)NRᶠRᵍ or R¹³' and R⁹ together with the atoms to which they are attached form a 5 to 7 membered ring; or R⁶ and R⁷ together with the atoms to which they are attached form a 5 to 6 membered heterocycle wherein the heterocycle is optionally fused with an optionally substituted aryl;

R⁸ and R⁹ are each independently, (C₁-C₆)alkyl, (C₁-C₆)alkanoyl or —C(=O)NRᶠRᵍ or R⁸ and R⁹ together with the atoms to which they are attached form a 5 to 7 membered ring; or R⁸—Z¹— and R⁹—Z²— can each independently be H;

R¹⁰ and R¹¹ are each independently, (C₁-C₆)alkyl, (C₁-C₆)alkanoyl or —C(=O)NRᶠRᵍ or R¹⁰ and R¹¹ together with the atoms to which they are attached form a 5 to 7 membered ring; or R¹⁰—Z³—, and R¹¹—Z⁴— can each independently be H;

each R¹³ is independently H, (C₁-C₆)alkyl, (C₁-C₆)alkoxy, (C₁-C₆)alkylthio, aryloxy or arylthio wherein any (C₁-C₆)alkyl, (C₁-C₆)alkoxy, and (C₁-C₆)alkylthio of R¹³ is optionally substituted with one or more groups selected from halo, cyano, oxo (=O), (C₁-C₆)alkyl, (C₃-C₆)cycloalkyl, carboxy, NO₂, hydroxy, (C₁-C₆)alkoxy, (C₁-C₆)alkoxycarbonyl, (C₁-C₆)alkanoyloxy, aryl, heteroaryl, aryloxy, heteroaryloxy, and —NRʰRⁱ, and wherein any aryloxy, or arylthio of R¹³ is optionally substituted with one or more groups selected from halo, cyano, (C₁-C₆)alkyl, (C₃-C₆)cycloalkyl, carboxy, NO₂, hydroxy, (C₁-C₆)alkoxy, (C₁-C₆)alkoxycarbonyl, (C₁-C₆)alkanoyloxy, aryl, heteroaryl, aryloxy, heteroaryloxy, and —NRʰRⁱ;

each R¹⁴ is independently H, (C₁-C₆)alkyl, (C₁-C₆)alkoxy, (C₁-C₆)alkylthio, aryloxy or arylthio wherein any (C₁-C₆)alkyl, (C₁-C₆)alkoxy, and (C₁-C₆)alkylthio of R¹⁴ is optionally substituted with one or more groups selected from halo, cyano, oxo (=O), (C₁-C₆)alkyl, (C₃-C₆)cycloalkyl, carboxy, NO₂, hydroxy, (C₁-C₆)alkoxy, (C₁-C₆)alkoxycarbonyl, (C₁-C₆)alkanoyloxy, aryl, heteroaryl, aryloxy, heteroaryloxy, and —NRʰRⁱ, and wherein any aryloxy, or arylthio of R¹⁴ is optionally substituted with one or more groups selected from halo, cyano, (C₁-C₆)alkyl, (C₃-C₆)cycloalkyl, carboxy, NO₂, hydroxy, (C₁-C₆)alkoxy, (C₁-C₆)alkoxycarbonyl, (C₁-C₆)alkanoyloxy, aryl, heteroaryl, aryloxy, heteroaryloxy, and —NRʰRⁱ;

$R^a$ is (C₁-C₆)alkyl wherein (C₁-C₆)alkyl is optionally substituted with one or more groups independently selected from halo, cyano, oxo (=O), (C₁-C₆)alkyl, (C₃-C₆)cycloalkyl, carboxy, NO₂, hydroxy, (C₁-C₆)alkoxy, (C₁-C₆)alkoxycarbonyl, (C₁-C₆)alkanoyloxy, aryl, heteroaryl, aryloxy, heteroaryloxy, and —NRʰRⁱ;

each Rᵉ is independently H or (C₁-C₆)alkyl wherein (C₁-C₆)alkyl is optionally substituted with one or more halo;

Rᶠ and Rᵍ are each independently H, (C₁-C₆)alkyl, aryl, heteroaryl, aryl(C₁-C₆) alkyl or heteroaryl(C₁-C₆) alkyl; or Rᶠ and Rᵍ together with the nitrogen to which they are attached form a morpholino, piperazino, pyrrolidino or piperidino;

Rʰ and Rⁱ are each independently H, (C₁-C₆)alkyl, aryl, heteroaryl, aryl(C₁-C₆) alkyl or heteroaryl(C₁-C₆) alkyl; or Rʰ and Rⁱ together with the nitrogen to which they are attached form a morpholino, piperazino, pyrrolidino or piperidino; and wherein R″ and Rᵖ may be the same or different and are chosen from hydrogen, alkyl, arylalkyl, heteroarylalkyl, cycloalkyl, substituted cycloalkyl, aryl, heteroaryl and heterocyclic;

or a salt or prodrug thereof, which is a compound of formula Ij:

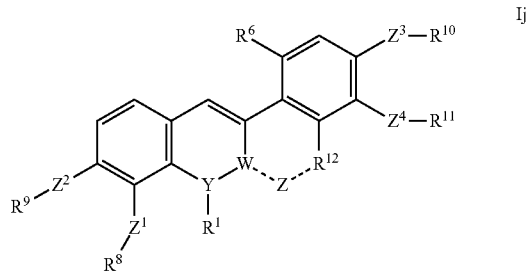

or a salt thereof.

5. A compound of formula I:

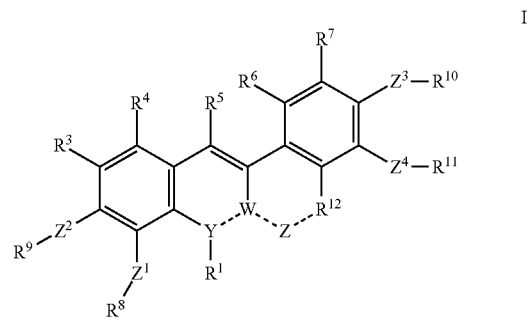

wherein:
the dashed line between Y and W represents a single or double bond;
when Y is —CR²—, Z is —(CR¹³₂)₂— or —CR¹⁴=CR¹⁴— and R¹² is a bond; W is N or (NRᵃ)⁺ X⁻;

when Y is —C═, Z is —(CR$^{13}{}_2$)$_2$— or —CR$^{14}$═CR$^{14}$— and R$^{12}$ is a bond; W is N$^+$X$^-$; or X$^-$ is a pharmaceutically suitable counterion;

Z$^1$, Z$^2$, Z$^3$ and Z$^4$ are each independently O, S or NR$^e$; or R$^8$—Z$^1$—, R$^9$—Z$^2$—, R$^{10}$—Z$^3$—, and R$^{11}$—Z$^4$— can each independently be H, optionally substituted aryl or optionally substituted heteroaryl;

R$^1$ is H, (C$_1$-C$_6$)alkyl, (C$_1$-C$_6$)alkoxy, (C$_1$-C$_6$)alkylthio, aryloxy or arylthio; and R$^2$ is H or (C$_1$-C$_6$)alkyl, wherein any (C$_1$-C$_6$)alkyl, (C$_1$-C$_6$)alkoxy, and (C$_1$-C$_6$)alkylthio of R$^1$ and R$^2$ is optionally substituted with one or more groups selected from halo, cyano, oxo (═O), (C$_1$-C$_6$)alkyl, (C$_3$-C$_6$)cycloalkyl, carboxy, NO$_2$, hydroxy, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, and —NR$^h$R$^i$, and wherein any aryloxy, or arylthio of R$^1$ and R$^2$ is optionally substituted with one or more groups selected from halo, cyano, (C$_1$-C$_6$)alkyl, (C$_3$-C$_6$)cycloalkyl, carboxy, NO$_2$, hydroxy, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, and —NR$^h$R$^i$;

at least one of R$^3$, R$^4$, R$^5$, R$^6$ and R$^7$ is aryl, heteroaryl, aryl(C$_1$-C$_6$)alkyl, heteroaryl(C$_1$-C$_6$)alkyl, aryl(C$_1$-C$_6$)alkanoyl or heteroaryl(C$_1$-C$_6$)alkanoyl and the remainder of R$^3$, R$^4$, R$^5$, R$^6$ and R$^7$ are independently H, halo, nitro, sulfo, —S(O)$_2$NR$^n$R$^p$, —N(R$^n$)S(O)$_2$R$^p$, —NR$^h$R$^i$ optionally substituted alkyl, optionally substituted arylalkyl, optionally substituted heteroarylalkyl, optionally substituted aryl, or optionally substituted heteroaryl; or R$^3$ is —Z$^{13}$R$^{13'}$ wherein Z$^{13}$ is O, S or NR$^e$ and R$^{13'}$ is (C$_1$-C$_6$)alkyl, substituted (C$_1$-C$_6$)alkyl, (C$_1$-C$_6$)alkanoyl or —C(═O)NR$^f$R$^g$ or R$^{13'}$ and R$^9$ together with the atoms to which they are attached form a 5 to 7 membered ring; or R$^6$ and R$^7$ together with the atoms to which they are attached form a 5 to 6 membered heterocycle wherein the heterocycle is optionally fused with an optionally substituted aryl;

R$^8$ and R$^9$ are each independently, (C$_1$-C$_6$)alkyl, (C$_1$-C$_6$)alkanoyl or —C(═O)NR$^f$R$^g$ or R$^8$ and R$^9$ together with the atoms to which they are attached form a 5 to 7 membered ring; or R$^8$—Z$^1$— and R$^9$—Z$^2$— can each independently be H;

R$^{10}$ and R$^{11}$ are each independently, (C$_1$-C$_6$)alkyl, (C$_1$-C$_6$)alkanoyl or —C(═O)NR$^f$R$^g$ or R$^{10}$ and R$^{11}$ together with the atoms to which they are attached form a 5 to 7 membered ring; or R$^{10}$—Z$^3$—, and R$^{11}$—Z$^4$— can each independently be H;

each R$^{13}$ is independently H, (C$_1$-C$_6$)alkyl, (C$_1$-C$_6$)alkoxy, (C$_1$-C$_6$)alkylthio, aryloxy or arylthio wherein any (C$_1$-C$_6$)alkyl, (C$_1$-C$_6$)alkoxy, and (C$_1$-C$_6$)alkylthio of R$^{13}$ is optionally substituted with one or more groups selected from halo, cyano, oxo (═O), (C$_1$-C$_6$)alkyl, (C$_3$-C$_6$)cycloalkyl, carboxy, NO$_2$, hydroxy, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, and —NR$^h$R$^i$, and wherein any aryloxy, or arylthio of R$^{13}$ is optionally substituted with one or more groups selected from halo, cyano, (C$_1$-C$_6$)alkyl, (C$_3$-C$_6$)cycloalkyl, carboxy, NO$_2$, hydroxy, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, and —NR$^h$R$^i$;

each R$^{14}$ is independently H, (C$_1$-C$_6$)alkyl, (C$_1$-C$_6$)alkoxy, (C$_1$-C$_6$)alkylthio, aryloxy or arylthio wherein any (C$_1$-C$_6$)alkyl, (C$_1$-C$_6$)alkoxy, and (C$_1$-C$_6$)alkylthio of R$^{14}$ is optionally substituted with one or more groups selected from halo, cyano, oxo (═O), (C$_1$-C$_6$)alkyl, (C$_3$-C$_6$)cycloalkyl, carboxy, NO$_2$, hydroxy, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, and —NR$^h$R$^i$, and wherein any aryloxy, or arylthio of R$^{14}$ is optionally substituted with one or more groups selected from halo, cyano, (C$_1$-C$_6$)alkyl, (C$_3$-C$_6$)cycloalkyl, carboxy, NO$_2$, hydroxy, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, and —NR$^h$R$^i$;

R$^a$ is (C$_1$-C$_6$)alkyl wherein (C$_1$-C$_6$)alkyl is optionally substituted with one or more groups independently selected from halo, cyano, oxo (═O), (C$_1$-C$_6$)alkyl, (C$_3$-C$_6$)cycloalkyl, carboxy, NO$_2$, hydroxy, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, and —NR$^h$R$^i$;

each R$^e$ is independently H or (C$_1$-C$_6$)alkyl wherein (C$_1$-C$_6$)alkyl is optionally substituted with one or more halo;

R$^f$ and R$^g$ are each independently H, (C$_1$-C$_6$)alkyl, aryl, heteroaryl, aryl(C$_1$-C$_6$) alkyl or heteroaryl(C$_1$-C$_6$) alkyl; or R$^f$ and R$^g$ together with the nitrogen to which they are attached form a morpholino, piperazino, pyrrolidino or piperidino;

R$^h$ and R$^i$ are each independently H, (C$_1$-C$_6$)alkyl, aryl, heteroaryl, aryl(C$_1$-C$_6$) alkyl or heteroaryl(C$_1$-C$_6$) alkyl; or R$^h$ and R$^i$ together with the nitrogen to which they are attached form a morpholino, piperazino, pyrrolidino or piperidino; and wherein R$^n$ and R$^p$ may be the same or different and are chosen from hydrogen, alkyl, arylalkyl, heteroarylalkyl, cycloalkyl, substituted cycloalkyl, aryl, heteroaryl and heterocyclic;

or a salt or prodrug thereof, which is a compound of the following formula:

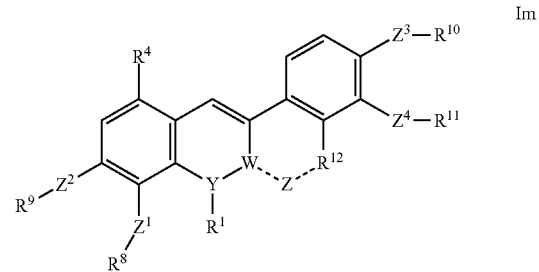

Im or a salt thereof.

6. A compound of formula I:

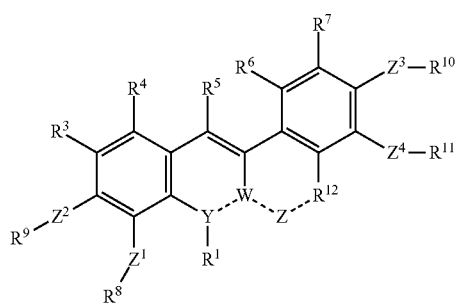

I wherein:
the dashed line between Y and W represents a single or double bond;
when Y is —$CR^2$—, Z is —$(CR^{13}{}_2)_2$— or —$CR^{14}$=$CR^{14}$— and $R^{12}$ is a bond; W is N or $(NR^a)^+$ $X^-$;
when Y is —C=, Z is —$(CR^{13}{}_2)_2$— or —$CR^{14}$=$CR^{14}$— and $R^{12}$ is a bond; W is $N^+X^-$; or
$X^-$ is a pharmaceutically suitable counterion;
$Z^1$, $Z^2$, $Z^3$ and $Z^4$ are each independently O, S or $NR^e$; or $R^8$—$Z^1$—, $R^9$—$Z^2$—, $R^{10}$—$Z^3$—, and $R^{11}$—$Z^4$— can each independently be H, optionally substituted aryl or optionally substituted heteroaryl;
$R^1$ is H, $(C_1$-$C_6)$alkyl, $(C_1$-$C_6)$alkoxy, $(C_1$-$C_6)$alkylthio, aryloxy or arylthio; and $R^2$ is H or $(C_1$-$C_6)$alkyl, wherein any $(C_1$-$C_6)$alkyl, $(C_1$-$C_6)$alkoxy, and $(C_1$-$C_6)$alkylthio of $R^1$ and $R^2$ is optionally substituted with one or more groups selected from halo, cyano, oxo (=O), $(C_1$-$C_6)$alkyl, $(C_3$-$C_6)$cycloalkyl, carboxy, $NO_2$, hydroxy, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^hR^i$, and wherein any aryloxy, or arylthio of $R^1$ and $R^2$ is optionally substituted with one or more groups selected from halo, cyano, $(C_1$-$C_6)$alkyl, $(C_3$-$C_6)$cycloalkyl, carboxy, $NO_2$, hydroxy, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^hR^i$;
at least one of $R^3$, $R^4$, $R^5$, $R^6$ and $R^7$ is aryl, heteroaryl, aryl$(C_1$-$C_6)$alkyl, heteroaryl$(C_1$-$C_6)$alkyl, aryl$(C_1$-$C_6)$alkanoyl or heteroaryl$(C_1$-$C_6)$alkanoyl and the remainder of $R^3$, $R^4$, $R^5$, $R^6$ and $R^7$ are independently H, halo, nitro, sulfo, —$S(O)_2NR^nR^p$, —$N(R^n)S(O)_2R^p$, —$NR^hR^i$ optionally substituted alkyl, optionally substituted arylalkyl, optionally substituted heteroarylalkyl, optionally substituted aryl, or optionally substituted heteroaryl; or $R^3$ is —$Z^{13}R^{13'}$ wherein $Z^{13}$ is O, S or $NR^e$ and $R^{13'}$ is $(C_1$-$C_6)$alkyl, substituted $(C_1$-$C_6)$alkyl, $(C_1$-$C_6)$alkanoyl or —C(=O)$NR^fR^g$ or $R^{13'}$ and $R^9$ together with the atoms to which they are attached form a 5 to 7 membered ring; or $R^6$ and $R^7$ together with the atoms to which they are attached form a 5 to 6 membered heterocycle wherein the heterocycle is optionally fused with an optionally substituted aryl;
$R^8$ and $R^9$ are each independently, $(C_1$-$C_6)$alkyl, $(C_1$-$C_6)$alkanoyl or —C(=O)$NR^fR^g$ or $R^8$ and $R^9$ together with the atoms to which they are attached form a 5 to 7 membered ring; or $R^8$—$Z^1$— and $R^9$—$Z^2$— can each independently be H;
$R^{10}$ and $R^{11}$ are each independently, $(C_1$-$C_6)$alkyl, $(C_1$-$C_6)$alkanoyl or —C(=O)$NR^fR^g$ or $R^{10}$ and $R^{11}$ together with the atoms to which they are attached form a 5 to 7 membered ring; or $R^{10}$—$Z^3$—, and $R^{11}$—$Z^4$— can each independently be H;
each $R^{13}$ is independently H, $(C_1$-$C_6)$alkyl, $(C_1$-$C_6)$alkoxy, $(C_1$-$C_6)$alkylthio, aryloxy or arylthio wherein any $(C_1$-$C_6)$alkyl, $(C_1$-$C_6)$alkoxy, and $(C_1$-$C_6)$alkylthio of $R^{13}$ is optionally substituted with one or more groups selected from halo, cyano, oxo (=O), $(C_1$-$C_6)$alkyl, $(C_3$-$C_6)$cycloalkyl, carboxy, $NO_2$, hydroxy, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^hR^i$, and wherein any aryloxy, or arylthio of $R^{13}$ is optionally substituted with one or more groups selected from halo, cyano, $(C_1$-$C_6)$alkyl, $(C_3$-$C_6)$cycloalkyl, carboxy, $NO_2$, hydroxy, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^hR^i$;
each $R^{14}$ is independently H, $(C_1$-$C_6)$alkyl, $(C_1$-$C_6)$alkoxy, $(C_1$-$C_6)$alkylthio, aryloxy or arylthio wherein any $(C_1$-$C_6)$alkyl, $(C_1$-$C_6)$alkoxy, and $(C_1$-$C_6)$alkylthio of $R^{14}$ is optionally substituted with one or more groups selected from halo, cyano, oxo (=O), $(C_1$-$C_6)$alkyl, $(C_3$-$C_6)$cycloalkyl, carboxy, $NO_2$, hydroxy, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^hR^i$, and wherein any aryloxy, or arylthio of $R^{14}$ is optionally substituted with one or more groups selected from halo, cyano, $(C_1$-$C_6)$alkyl, $(C_3$-$C_6)$cycloalkyl, carboxy, $NO_2$, hydroxy, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^hR^i$;
$R^a$ is $(C_1$-$C_6)$alkyl wherein $(C_1$-$C_6)$alkyl is optionally substituted with one or more groups independently selected from halo, cyano, oxo (=O), $(C_1$-$C_6)$alkyl, $(C_3$-$C_6)$cycloalkyl, carboxy, $NO_2$, hydroxy, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^hR^i$;
each $R^e$ is independently H or $(C_1$-$C_6)$alkyl wherein $(C_1$-$C_6)$alkyl is optionally substituted with one or more halo;
$R^f$ and $R^g$ are each independently H, $(C_1$-$C_6)$alkyl, aryl, heteroaryl, aryl$(C_1$-$C_6)$ alkyl or heteroaryl$(C_1$-$C_6)$ alkyl; or $R^f$ and $R^g$ together with the nitrogen to which they are attached form a morpholino, piperazino, pyrrolidino or piperidino;
$R^h$ and $R^i$ are each independently H, $(C_1$-$C_6)$alkyl, aryl, heteroaryl, aryl$(C_1$-$C_6)$ alkyl or heteroaryl$(C_1$-$C_6)$ alkyl; or $R^h$ and $R^i$ together with the nitrogen to which they are attached form a morpholino, piperazino, pyrrolidino or piperidino; and
wherein $R^n$ and $R^p$ may be the same or different and are chosen from hydrogen, alkyl, arylalkyl, heteroarylalkyl, cycloalkyl, substituted cycloalkyl, aryl, heteroaryl and heterocyclic;
or a salt or prodrug thereof, which is a compound of formula In:

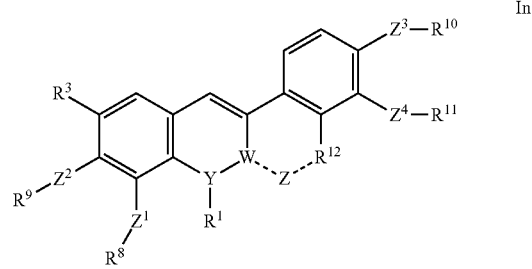

or a salt thereof.

7. A compound of formula I:

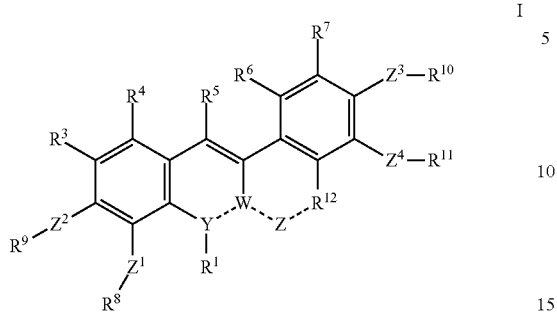

wherein:
the dashed line between Y and W represents a single or double bond;
when Y is —$CR^2$—, Z is —$(CR^{13}{}_2)_2$— or —$CR^{14}$=$CR^{14}$— and $R^{12}$ is a bond; W is N or $(NR^a)^+ X^-$;
when Y is —C=, Z is —$(CR^{13}{}_2)_2$— or —$CR^{14}$=$CR^{14}$— and $R^{12}$ is a bond; W is $N^+ X^-$; or
$X^-$ is a pharmaceutically suitable counterion;
$Z^1, Z^2, Z^3$ and $Z^4$ are each independently O, S or $NR^e$; or $R^8$—$Z^1$—, $R^9$—$Z^2$—, $R^{10}$—$Z^3$—, and $R^{11}$—$Z^4$— can each independently be H, optionally substituted aryl or optionally substituted heteroaryl;
$R^1$ is H, $(C_1-C_6)$alkyl, $(C_1-C_6)$alkoxy, $(C_1-C_6)$alkylthio, aryloxy or arylthio; and $R^2$ is H or $(C_1-C_6)$alkyl, wherein any $(C_1-C_6)$alkyl, $(C_1-C_6)$alkoxy, and $(C_1-C_6)$alkylthio of $R^1$ and $R^2$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^1$ and $R^2$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;
at least one of $R^3, R^4, R^5, R^6$ and $R^7$ is aryl, heteroaryl, aryl$(C_1-C_6)$alkyl, heteroaryl$(C_1-C_6)$alkyl, aryl$(C_1-C_6)$alkanoyl or heteroaryl$(C_1-C_6)$alkanoyl and the remainder of $R^3, R^4, R^5, R^6$ and $R^7$ are independently H, halo, nitro, sulfo, —$S(O)_2NR^nR^p$, —$N(R^n)S(O)_2R^p$, —$NR^hR^i$ optionally substituted alkyl, optionally substituted arylalkyl, optionally substituted heteroarylalkyl, optionally substituted aryl, or optionally substituted heteroaryl; or $R^3$ is —$Z^{13}R^{13'}$ wherein $Z^{13}$ is O, S or $NR^e$ and $R^{13'}$ is $(C_1-C_6)$alkyl, substituted $(C_1-C_6)$alkyl, $(C_1-C_6)$alkanoyl or —C(=O)$NR^fR^g$ or $R^{13'}$ and $R^9$ together with the atoms to which they are attached form a 5 to 7 membered ring; or $R^6$ and $R^7$ together with the atoms to which they are attached form a 5 to 6 membered heterocycle wherein the heterocycle is optionally fused with an optionally substituted aryl;
$R^8$ and $R^9$ are each independently, $(C_1-C_6)$alkyl, $(C_1-C_6)$alkanoyl or —C(=O)$NR^fR^g$ or $R^8$ and $R^9$ together with the atoms to which they are attached form a 5 to 7 membered ring; or $R^8$—$Z^1$— and $R^9$—$Z^2$— can each independently be H;
$R^{10}$ and $R^{11}$ are each independently, $(C_1-C_6)$alkyl, $(C_1-C_6)$alkanoyl or —C(=O)$NR^fR^g$ or $R^{10}$ and $R^{11}$ together with the atoms to which they are attached form a 5 to 7 membered ring; or $R^{10}$—$Z^3$—, and $R^{11}$—$Z^4$— can each independently be H;
each $R^{13}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{13}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^{13}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;
each $R^{14}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{14}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$, and wherein any aryloxy, or arylthio of $R^{14}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;
$R^a$ is $(C_1-C_6)$alkyl wherein $(C_1-C_6)$alkyl is optionally substituted with one or more groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^hR^i$;
each $R^e$ is independently H or $(C_1-C_6)$alkyl wherein $(C_1-C_6)$alkyl is optionally substituted with one or more halo;
$R^f$ and $R^g$ are each independently H, $(C_1-C_6)$alkyl, aryl, heteroaryl, aryl$(C_1-C_6)$ alkyl or heteroaryl$(C_1-C_6)$ alkyl; or $R^f$ and $R^g$ together with the nitrogen to which they are attached form a morpholino, piperazino, pyrrolidino or piperidino;
$R^h$ and $R^i$ are each independently H, $(C_1-C_6)$alkyl, aryl, heteroaryl, aryl$(C_1-C_6)$ alkyl or heteroaryl$(C_1-C_6)$ alkyl; or $R^h$ and $R^i$ together with the nitrogen to which they are attached form a morpholino, piperazino, pyrrolidino or piperidino; and
wherein $R^n$ and $R^p$ may be the same or different and are chosen from hydrogen, alkyl, arylalkyl, heteroarylalkyl, cycloalkyl, substituted cycloalkyl, aryl, heteroaryl and heterocyclic;
or a salt or prodrug thereof, which is a compound of formula Ip:

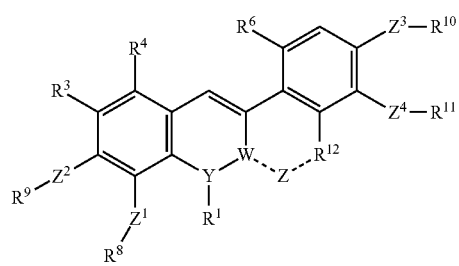
or a salt thereof.
8. A compound which is selected from:
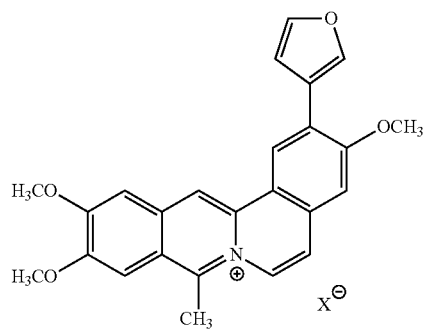
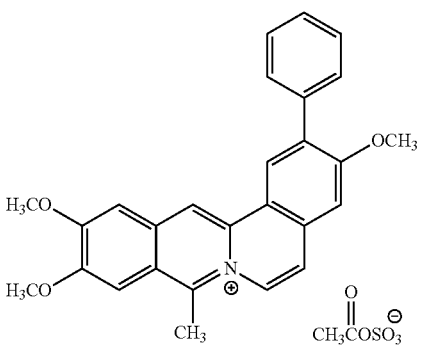
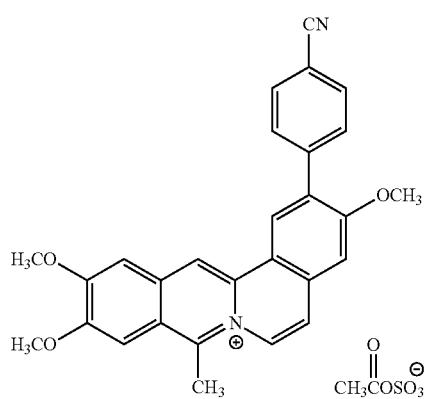
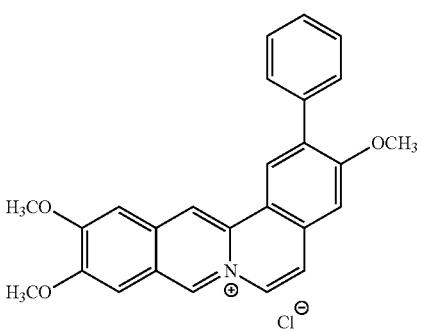
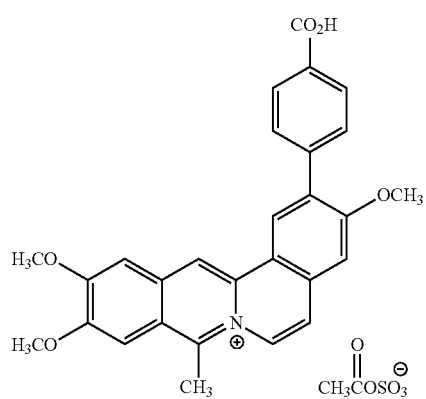
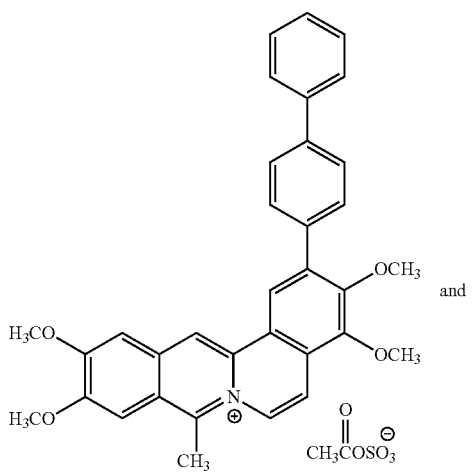
and -continued
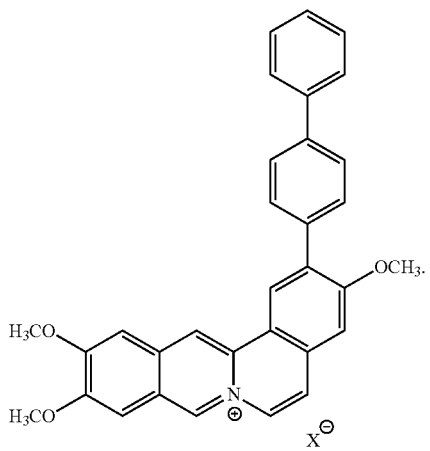
9. A compound which is selected from:
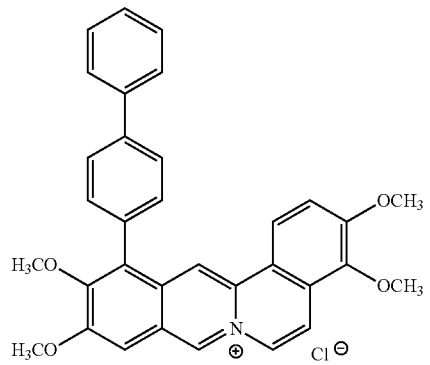
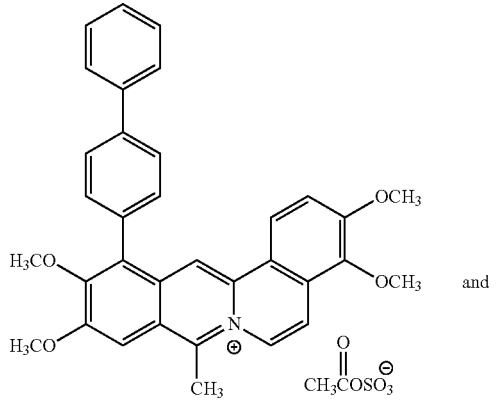
and
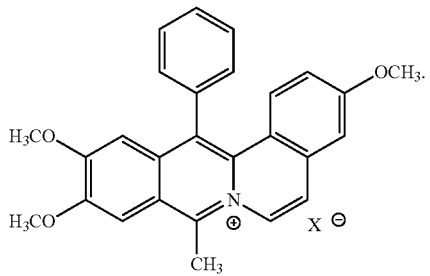
10. A compound which is selected from:
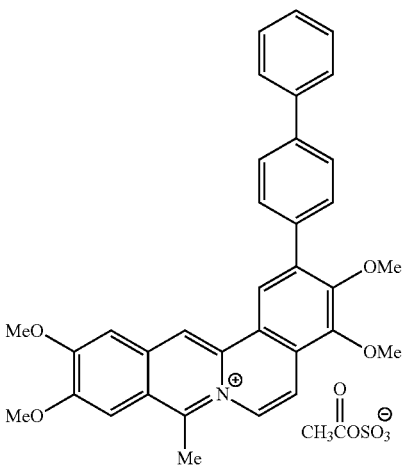
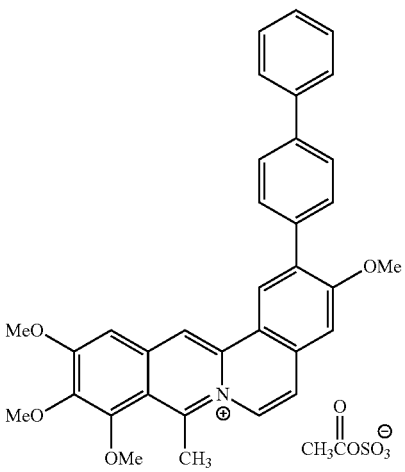
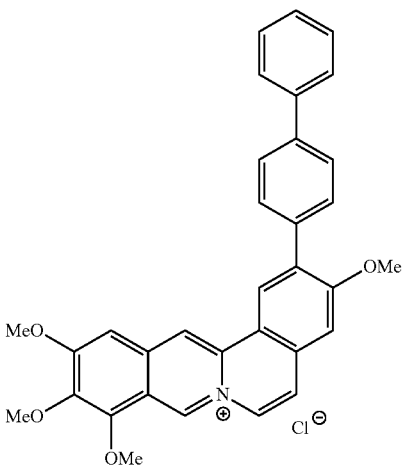

141
-continued
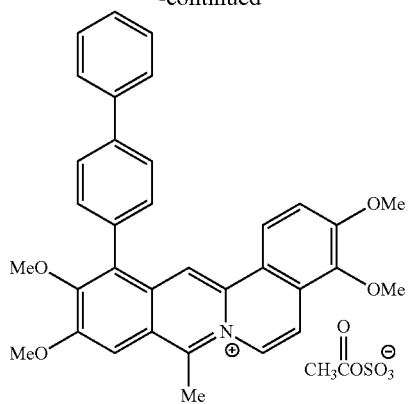
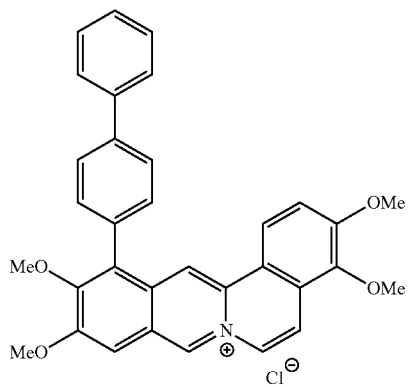
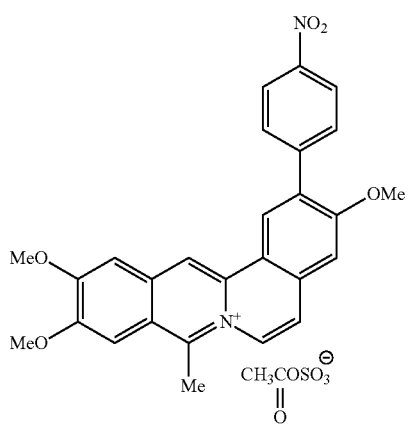
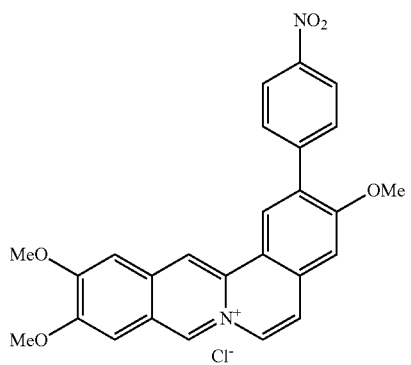
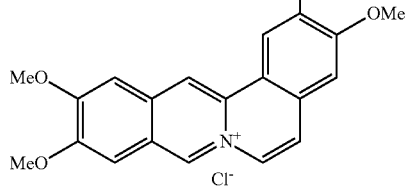
142
-continued
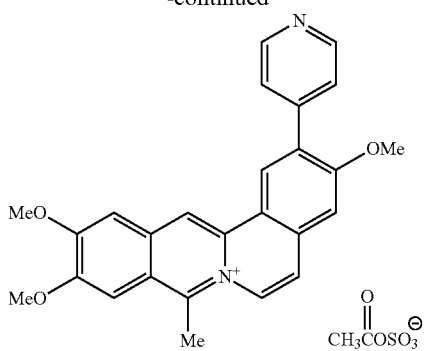
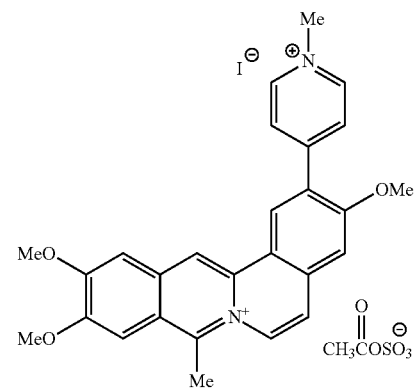
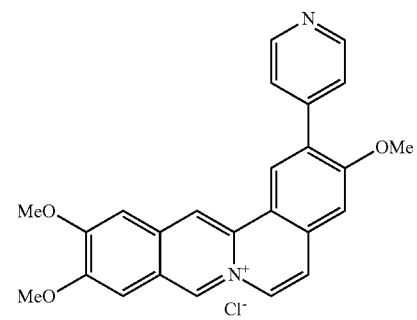
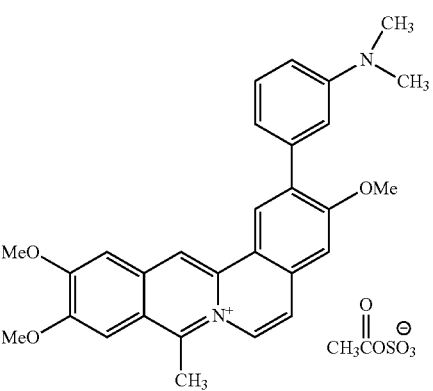

143
-continued
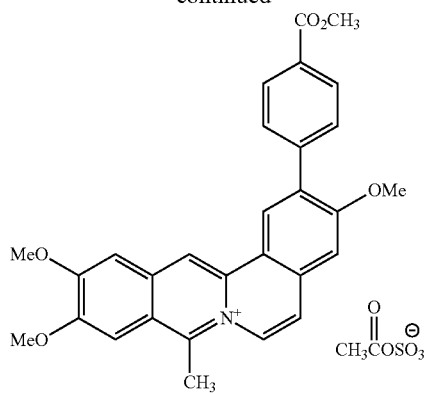
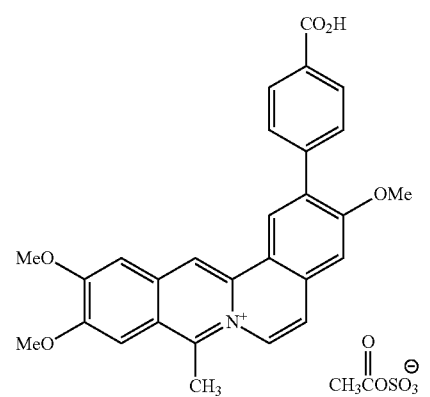
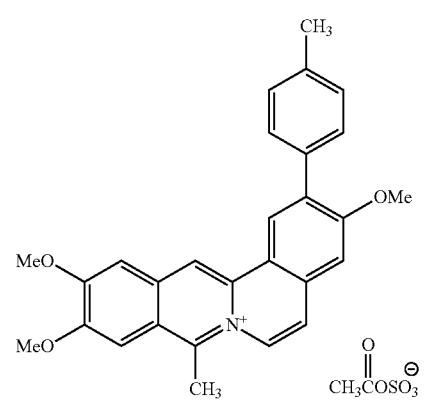
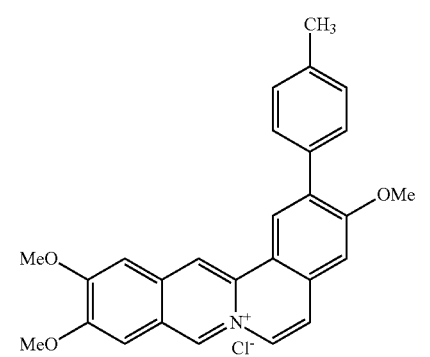
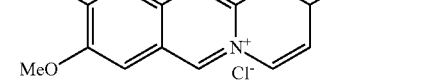
144
-continued
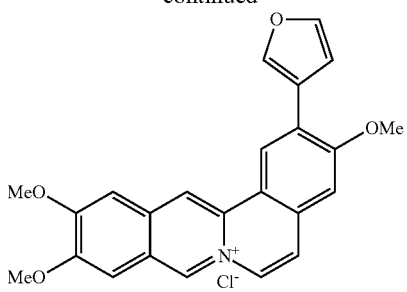
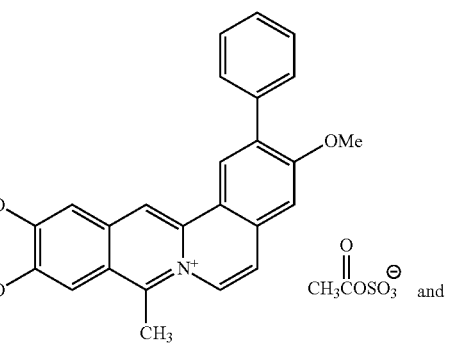 and
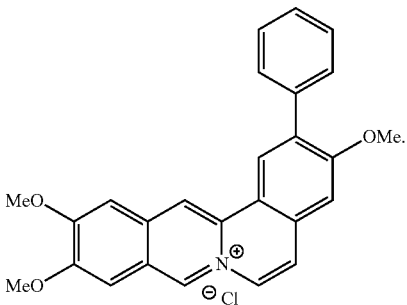
11. A compound selected from:
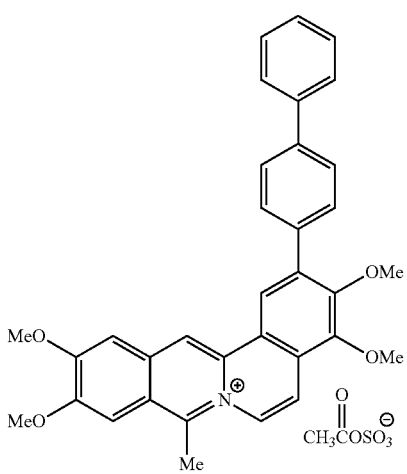

145
-continued
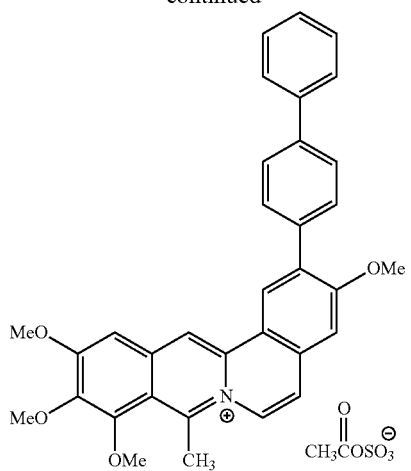
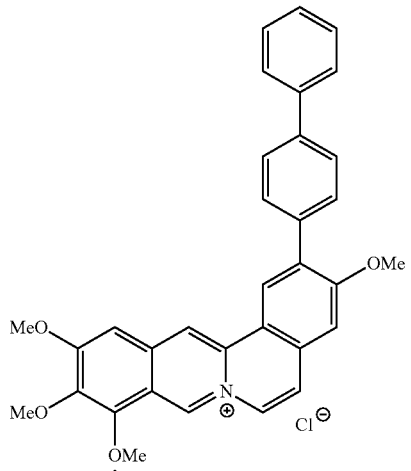
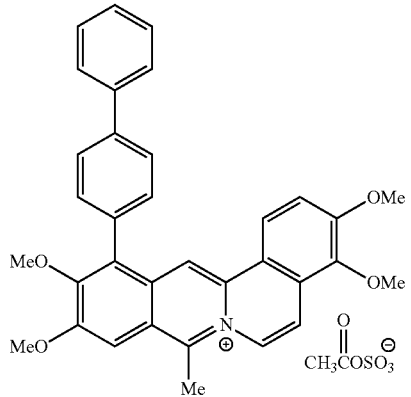
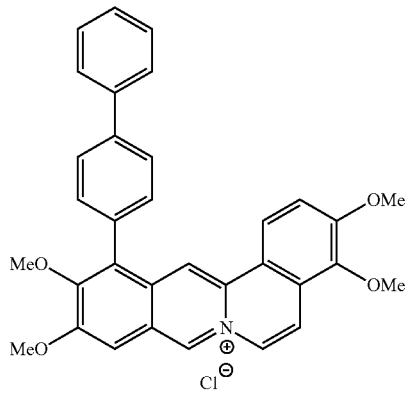
146
-continued
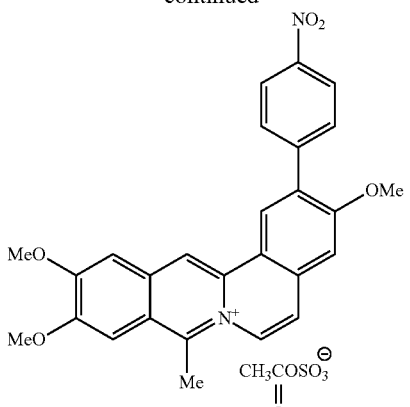
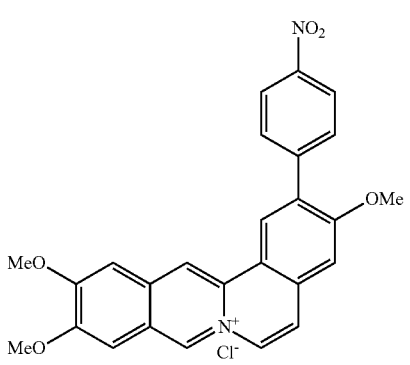
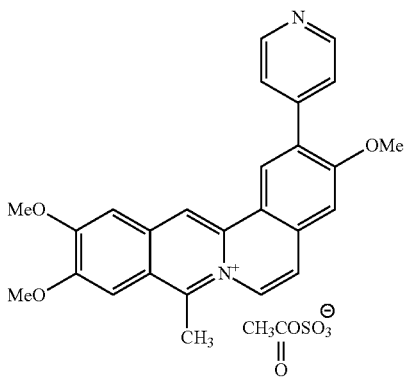
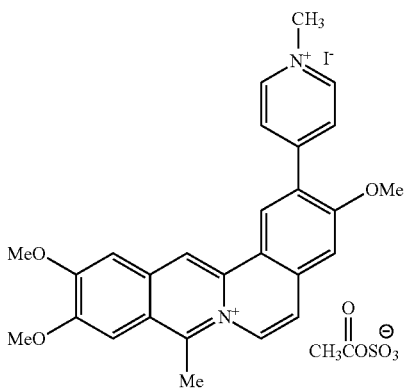

147
-continued
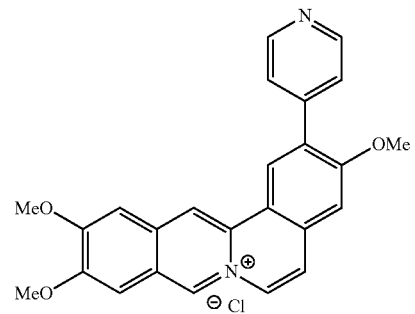
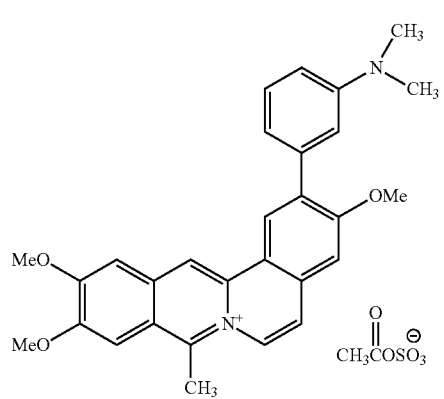
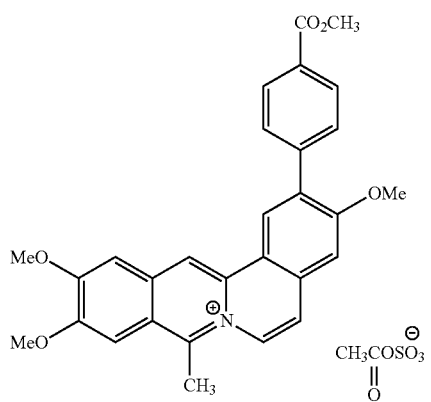
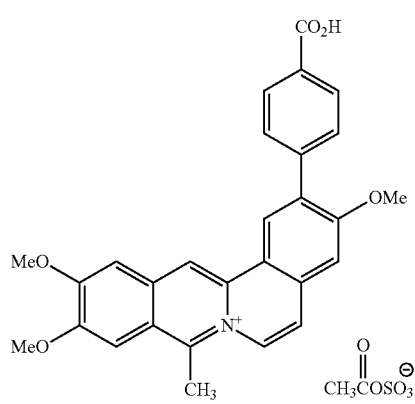
148
-continued
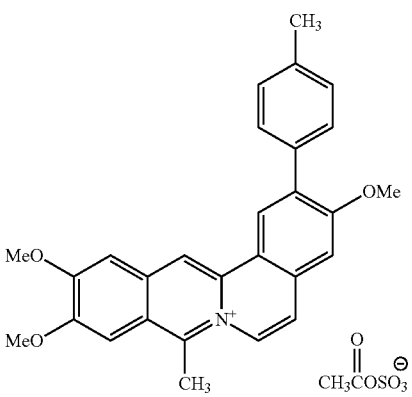
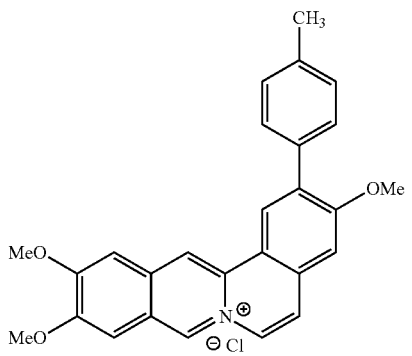
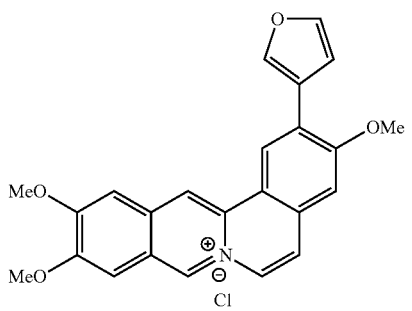
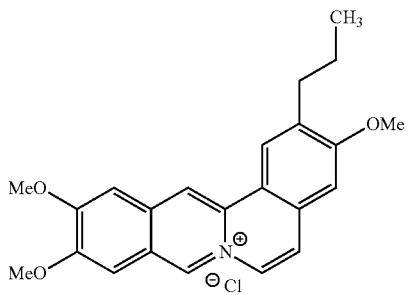
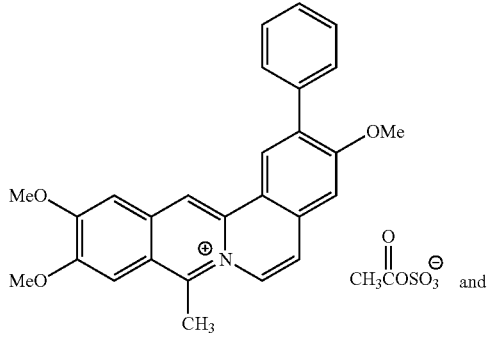
and

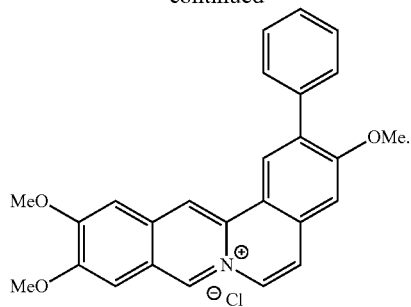
12. A composition comprising a compound as described in claim 11 and a pharmaceutically acceptable vehicle.
* * * * *